(12) United States Patent
Kakuta et al.

(10) Patent No.: US 9,878,104 B2
(45) Date of Patent: Jan. 30, 2018

(54) METERED QUANTITY SYRINGE-TYPE DISPENSER

(71) Applicant: YOSHINO KOGYOSHO CO., LTD., Koto-ku, Tokyo (JP)

(72) Inventors: Yoshiyuki Kakuta, Tokyo (JP); Toru Toma, Tokyo (JP); Shinya Hoshino, Tokyo (JP)

(73) Assignee: YOSHINO KOGYOSHO CO., LTD., Tokyo (JP)

( * ) Notice: Subject to any disclaimer, the term of this patent is extended or adjusted under 35 U.S.C. 154(b) by 699 days.

(21) Appl. No.: 14/387,481

(22) PCT Filed: Mar. 29, 2013

(86) PCT No.: PCT/JP2013/002204
§ 371 (c)(1),
(2) Date: Sep. 23, 2014

(87) PCT Pub. No.: WO2013/145789
PCT Pub. Date: Oct. 3, 2013

(65) Prior Publication Data
US 2015/0075520 A1   Mar. 19, 2015

(30) Foreign Application Priority Data

Mar. 30, 2012   (JP) ................................. 2012-082385
Apr. 27, 2012   (JP) ................................. 2012-103300
(Continued)

(51) Int. Cl.
*A61M 5/315*     (2006.01)
*A61M 11/00*     (2006.01)
(Continued)

(52) U.S. Cl.
CPC ........ *A61M 5/31595* (2013.01); *A61M 11/00* (2013.01); *A61M 11/007* (2014.02);
(Continued)

(58) Field of Classification Search
CPC ................ A61M 11/08; A61M 11/007; A61M 5/31526; A61M 5/31595; A61M 15/0028;
(Continued)

(56) References Cited

U.S. PATENT DOCUMENTS 4,391,272 A    7/1983   Staempfli
4,950,163 A    8/1990   Zimble
(Continued)

FOREIGN PATENT DOCUMENTS

CA    2329707 A1    11/1999
GB    2163490 A     2/1986
(Continued)

OTHER PUBLICATIONS

Oct. 26, 2015 Search Report issued in European Patent Application No. 13767559.1.
(Continued)

*Primary Examiner* — Bhisma Mehta
*Assistant Examiner* — James D Ponton
(74) *Attorney, Agent, or Firm* — Oliff PLC

(57) ABSTRACT

Provided is a metered quantity syringe-type dispenser that is capable of multistage pushing. The metered quantity syringe-type dispenser includes a syringe; a plunger configured to be pushed into the syringe; an elastic deforming portion configured to be deformed in response to the pushing of the plunger; and a stopper portion configured to be locked with respect to the syringe and to be released from the locking by restoring force of the elastic deforming portion.

15 Claims, 50 Drawing Sheets

(30) Foreign Application Priority Data

| May 30, 2012 | (JP) | ................................. | 2012-123748 |
|---|---|---|---|
| May 31, 2012 | (JP) | ................................. | 2012-124312 |
| May 31, 2012 | (JP) | ................................. | 2012-125165 |
| Jul. 31, 2012 | (JP) | ................................. | 2012-170558 |
| Jul. 31, 2012 | (JP) | ................................. | 2012-170559 |
| Sep. 28, 2012 | (JP) | ................................. | 2012-218330 |
| Sep. 28, 2012 | (JP) | ................................. | 2012-218607 |

(51) Int. Cl.
   *A61M 15/08* (2006.01)
   *B05B 11/02* (2006.01)
   *A61M 11/08* (2006.01)
   *A61M 15/00* (2006.01)

(52) U.S. Cl.
   CPC .......... *A61M 11/08* (2013.01); *A61M 15/009* (2013.01); *A61M 15/0028* (2013.01); *A61M 15/08* (2013.01); *B05B 11/025* (2013.01); *A61M 2005/31508* (2013.01); *A61M 2210/0618* (2013.01)

(58) Field of Classification Search
   CPC ................ A61M 15/009; A61M 15/08; A61M 2005/31508; A61M 5/3271; A61M 5/3272; B05B 11/025
   See application file for complete search history.

(56) References Cited

U.S. PATENT DOCUMENTS 7,967,010 B2 * 6/2011 Vedrine ............... A61M 5/2429
                                                    128/200.14

2007/0145077 A1   6/2007  Harrold

FOREIGN PATENT DOCUMENTS

| JP | A-54-129793 | 10/1979 |
|---|---|---|
| JP | A-7-213612 | 8/1995 |
| JP | A-2002-515268 | 5/2002 |
| JP | A-2008-200316 | 9/2008 |
| JP | A-2012-139330 | 7/2012 |
| JP | A-2013-31563 | 2/2013 |
| JP | A-2013-31599 | 2/2013 |
| WO | 99/55402 A1 | 11/1999 |

OTHER PUBLICATIONS

Jun. 19, 2015 Office Action issued in Australian Patent Application No. 2013238598.

Sep. 4, 2015 Office Action issued in Canadian Patent Application No. 2,869,155.

Jun. 25, 2013 Written Opinion issued in International Patent Application No. PCT/JP2013/002204.

Jun. 25, 2013 International Search Report issued in International Patent Application No. PCT/JP2013/002204.

Sep. 9, 2016 Office Action issued in Chinese Patent Application No. 201380027240.4.

Feb. 3, 2016 Office Action issued in Chinese Patent Application No. 2013800272404.

* cited by examiner

Section X-X

METERED QUANTITY SYRINGE-TYPE DISPENSER

TECHNICAL FIELD

The present invention relates to a metered quantity syringe-type dispenser.

BACKGROUND ART

Examples of a conventional syringe-type dispenser include the one by which a content such as a medicinal fluid is withdrawn by pushing a plunger into a syringe (For example, refer to Patent Literature 1).

CITATION LIST

Patent Literature

PTL 1: JPH07213612A

SUMMARY OF THE INVENTION

Technical Problems

However, in such a conventional syringe-type dispenser, since merely the plunger is pushed into the syringe, it is difficult to fraction the content for ejection.

The present invention is to provide a novel metered quantity syringe-type dispenser that is capable of multistage pushing.

Solution to Problems

One aspect of the present invention provides a metered quantity syringe-type dispenser, including: a syringe; a plunger configured to be pushed into the syringe; an elastic deforming portion configured to be deformed in response to the pushing of the plunger; and a stopper portion configured to be locked with respect to the syringe and to be released from the locking by restoring force of the elastic deforming portion.

Advantageous Effects of Invention

According to the present invention, simply by pushing and releasing the plunger with respect to a content filled in the single syringe, multistage pushing is achieved.

DESCRIPTION OF EMBODIMENTS

The following describes various embodiments of a metered quantity syringe-type dispenser of the present invention in detail with reference to the drawings.

Figure 1:
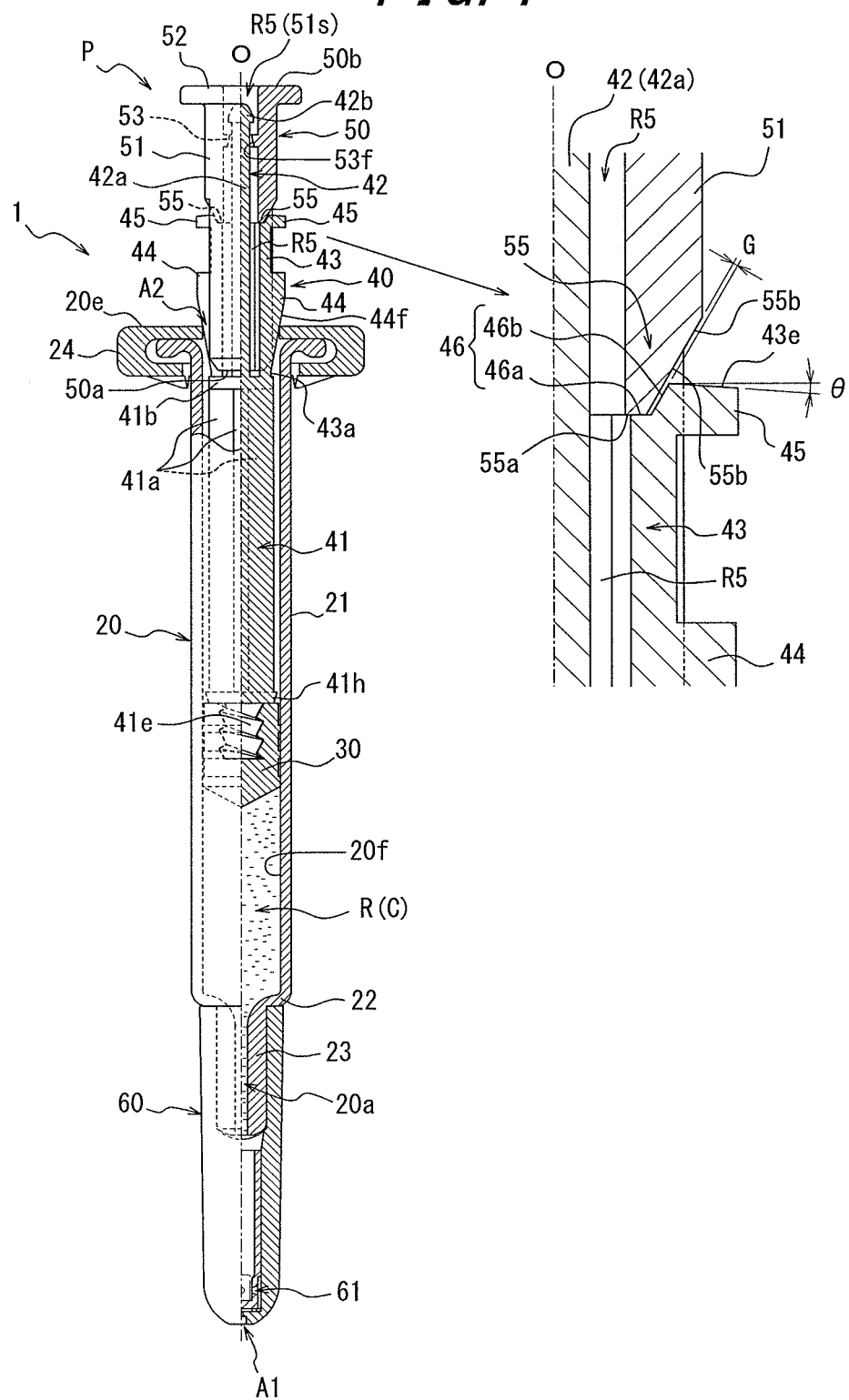
FIG. 1 is a side view taken along a partial section illustrating a nasal spray dispenser that is in an initial state prior to an operation thereof, and a partially enlarged view of the nasal spray dispenser, according to Embodiment 1 of the present invention.

In FIG. 1, reference numeral 1 refers to a synthetic resin nasal spray dispenser according to Embodiment 1 of the present invention. Reference numeral 20 refers to a syringe made of synthetic resin or glass that may be filled with a content (nasal drops) C. The syringe 20 has a hollow trunk portion 21 and a front end portion 23 integrally connected to the trunk portion 21 via a shoulder portion 22. The front end portion 23 is smaller in diameter than the trunk portion 21. In the trunk portion 21, in a rear end portion thereof that is opposite to the front end portion 23, a finger rest 24 is provided as a separate member. The finger rest 24 is provided with an opening A2 through which an inside of the syringe 20 communicates with an outside. Thus, a rear end of the finger rest 24 constitutes a rear end 20e of the syringe 20. The finger rest 24 may also be integrally provided with the trunk portion 21.

Reference numeral P refers to a plunger made of synthetic resin that may be pushed into the syringe 20. The plunger P includes a piston holding member 40 and a plunger operation member 50 disposed in the rear of the piston holding member 40.

The piston holding member 40 includes a main body 41 configured to hold a piston 30. The piston 30 is provided in a front end portion of the main body 41. The main body 41 includes a fixing portion 41h configured to fix the piston 30, elongate four plate portions 41a that are assembled in a manner such that the four plate portions 41a have a cross-shaped cross section, and a disk portion 41b, all of which are integrated. The piston 30 is made of an elastic material such as rubber or the like and is slidably held on an inner circumferential surface 20f of the trunk portion 21 of the syringe.

The piston 30 provided in the main body 41 forms room R between the piston 30 and the syringe 20. The room R is configured to be filled with a content C. The content C is pumped to a through hole 20a formed in the front end portion 23 in response to pushing of the piston 30.

Figure 2:
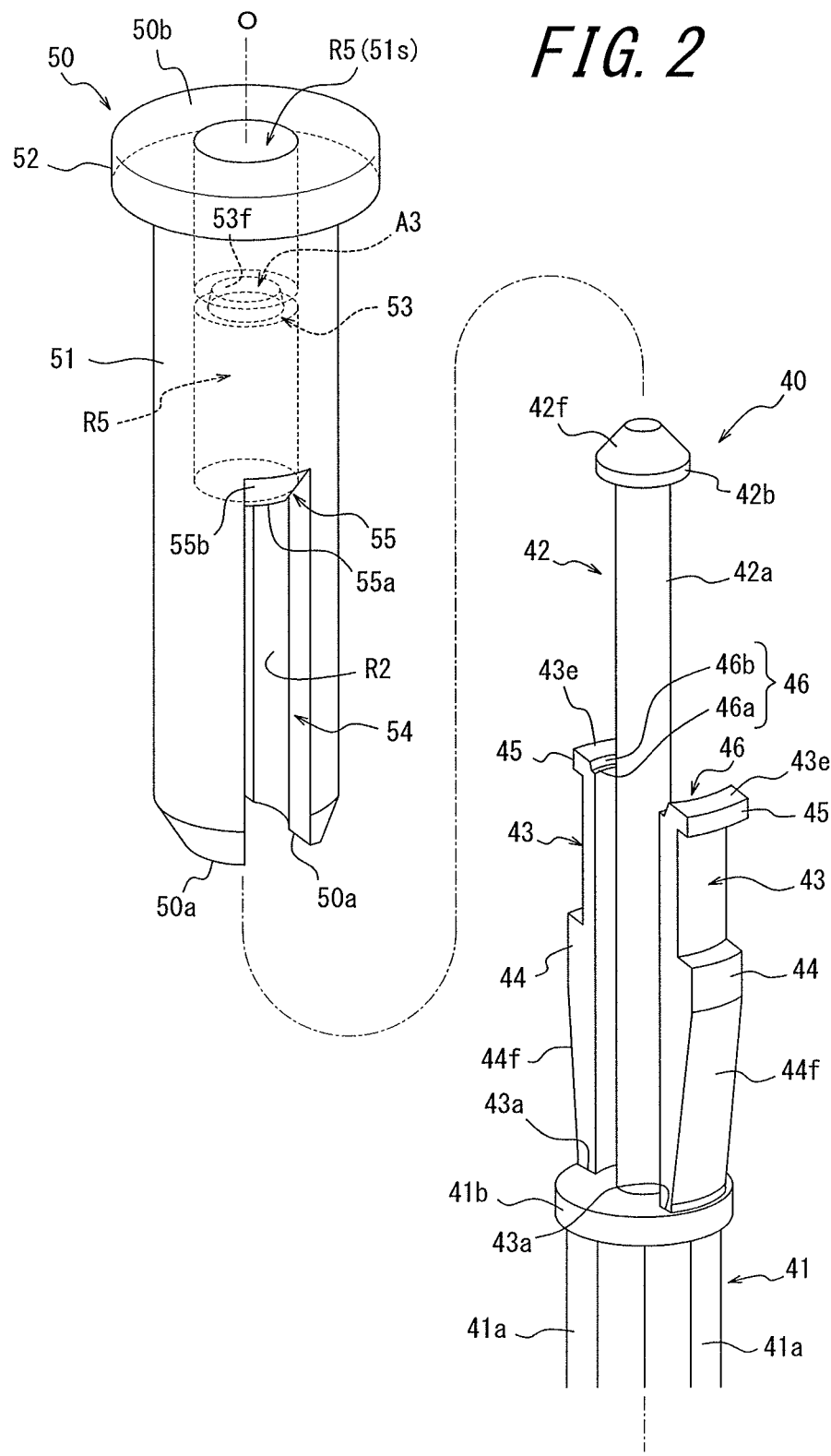
FIG. 2 is an exploded perspective view schematically illustrating a part of a piston holding member and a plunger operation member that are illustrated in FIG. 1.

The main body 41 is also provided with a shaft 42 in an integrated manner. As illustrated in FIG. 2, the shaft 42 includes a shaft body 42a with a diameter smaller than a diameter of the disk portion 41b. The shaft body 42a extends rearward from the disk portion 41b along an axis line (center axis line of the nasal spray dispenser 1). The shaft body 42a is provided, at an end thereof, with a head 42b having a diameter greater than the diameter of the shaft body 42a, in an integrated manner. The head 42b includes an inclined surface 42f that tapers toward a front end of the head 42b.

The main body 41 is provided with two arms 43 integrally formed therewith. The arms 43 are positioned in a manner such that the arms 43 oppose to each other across the shaft 42. The arms 43 each have a plate shape and extend rearward from the disk portion 41b along the axis line O. Each arm 43 may be deformed inward in a radial direction (a direction perpendicular to the axis line O) from a fixed end 43a, when loaded with external force. When the load is released, the arm 43 may also be restored to an initial position (a position illustrated in FIG. 1 in the present embodiment). With the above structure, a free end 43e of the arm 43 may be displaced inward in the radial direction and may be restored to the initial position. In the present embodiment, the arm 43 is formed in a small thickness, and accordingly, the arm 43 is easily deformed and restored.

The arms 43 are each also provided with a slide projection 44 in an integrated manner. As illustrated in FIG. 1, the slide projections 44 are positioned in a manner such that the slide projections 44 face the inner circumferential surface 20f of the syringe 20. Furthermore, as illustrated in FIG. 1, the two slide projections 44 opposing to each other about the axis line O have an interval between outermost diameters thereof in the radial direction that is greater than an inner diameter of the syringe 20 (which is the same as a diameter of the opening A2 provided in the rear end of the syringe in the present embodiment). When the slide projections 44 come into contact with the opening A2 provided in the rear end of the syringe 20, the arms 43 undergo flexure deformation starting from the fixed ends 43a. As a result, the slide projections 44 enter the syringe 20 and slide on the inner circumferential surface 20f of the syringe 20.

In the present embodiment, each slide projection 44 includes an inclined surface 44f that tapers toward the corresponding fixed end 43a. With the above structure, the slide projection 44 may easily enter the syringe 20 though the opening A2 provided in the rear end of the syringe 20.

The arms 43 are also each provided with a protrusion 45 integrally formed therewith. As illustrated in FIG. 1, the protrusions 45 are positioned in a manner such that the protrusions 45 face the inner circumferential surface 20f of the syringe 20. The protrusions 45 are each arranged rearward of the corresponding slide projection 44 at an interval therefrom. Furthermore, the protrusions 45 have an interval between outermost diameters thereof in the radial direction that is greater than the diameter of the opening A2 provided in the rear end of the syringe 20. With the above structure, when coming into contact with the opening A2 provided in the rear end of the syringe 20 to be locked, the protrusions 45 serve as a stopper portion that restricts the piston holding member 40 from entering the syringe 20.

In the present embodiment, as illustrated in FIG. 2, the protrusions 45 are formed integrally on a side of the free ends of the arms 43. That is to say, in the present embodiment, a rear end surface of each protrusion 45 constitutes the free end 43e of the corresponding arm 43. Furthermore, in the present embodiment, as illustrated in an enlarged view of FIG. 1, the free end 43e of the arm 43 is configured by a taper inclined outward (i.e. inclined inward as the free end 43e advances rearward) at an angle θ with respect to a line (a horizontal line) that is perpendicular to the axis line O. For example, the angle θ is set in a manner such that, when the arm 43 is inclined inward, the arm 43 is parallel to the aforementioned horizontal line.

Furthermore, in the present embodiment, as illustrated in the enlarged view of FIG. 1, the protrusion 45 is provided with a step 46. The step 46 is formed on an inner surface side of the arm 43. In the present embodiment, the step 46 includes a flat step bottom surface 46a and a step side surface 46b connected to the step bottom surface 46a. In the present embodiment, the step side surface 46b is formed as a tapered surface inclined outward from the step bottom surface 46a to the free end 43e of the arm 43.

On the other hand, as illustrated in FIG. 2, the plunger operation member 50 includes a main body 51. The main body 51 is provided, at a rear end thereof, in an integrated manner with a plunger operation portion 52 for a user to push in the plunger P. As illustrated in FIG. 2, the main body 51 has a cylindrical shape. In an inside of the plunger operation member 50, inner room R5 is formed to extend throughout between a front end 50a and a rear end 50b of the plunger operation member 50. The shaft 42 of the piston holding member 40 is configured to penetrate through the inner room R5. With the above structure, the shaft 42 prevents movement (unsteadiness) of the plunger operation member 50 about the axis line O.

As illustrated in FIG. 2, the plunger operation member 50 is also provided, in the inner room R5, with an annular projection 53. The annular projection 53 projects from an inside of the main body 51. The annular 53 is also provided with an opening A3 having a diameter smaller than a diameter of the inner room R5. The opening A3 has an inner diameter that is greater than the diameter of the shaft body 42a and smaller than a diameter of the head 42b. As illustrated in FIG. 1, the annular projection 53 lets the shaft body 42a penetrate therethrough, and the annular projection 53 also holds the head 42b by preventing the head 42b from slipping off. That is to say, the head 42b and the annular projection 53 function as a locking portion that holds the piston holding member 40 to the plunger operation member 50 by preventing the piston holding member 40 from slipping off.

In the present embodiment in particular, the annular projection 53 has an inner circumferential surface 53f formed as a tapered surface whose diameter decreases rearward. With the above structure, the head 42b is easily assembled to an inside of the annular projection 53 through the opening A3. Furthermore, since the annular projection 53 is provided in the inner room R5, play space 51s is formed. Owing to the play space 51s, the head 42b may be displaced forward and rearward along the axis line O in a portion of the inner room R5 that is on a rear end side of the annular projection 53. With the above structure, the piston holding member 40 and the plunger operation member 50 may be displaceably coupled to each other along the axis line O.

Figure 3:
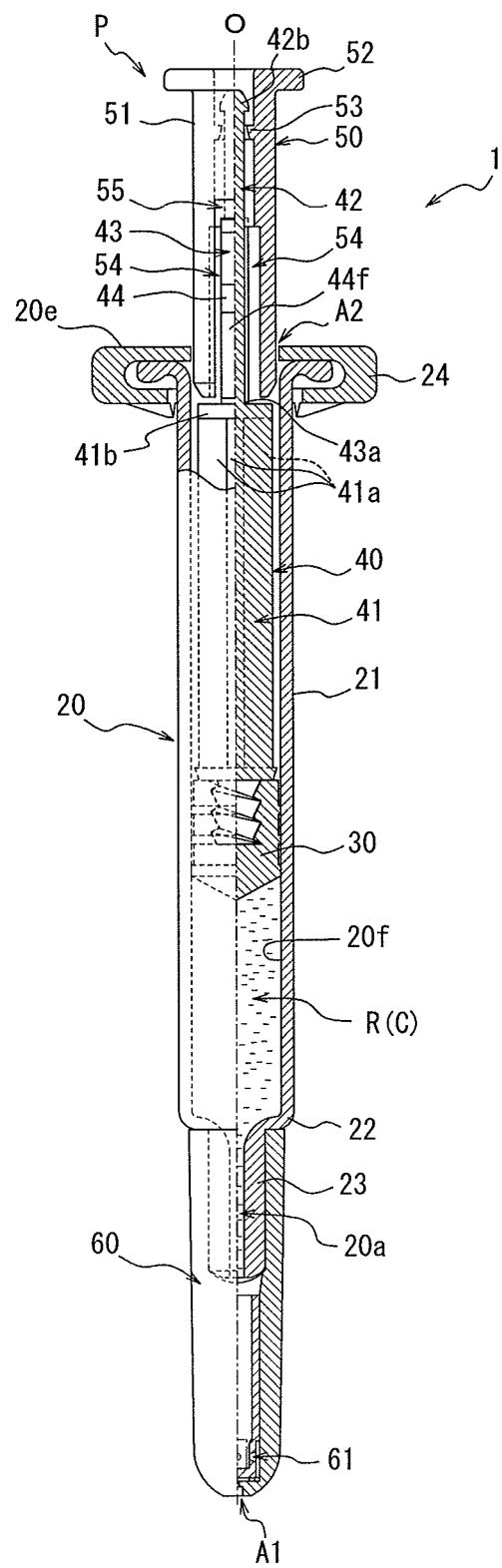
FIG. 3 is another side view corresponding to FIG. 1 as taken along a partial section.

As illustrated in FIG. 2, the main body 51 is provided with a plurality of cutouts 54 communicating with the inner room R5. As illustrated in FIG. 3, the shaft 42 and the arm 43 are operatively arranged in the cutouts 54, and as a result, the movement of the arm 43 is substantially restricted to that along the radial direction. Each cutout 54 includes an abutment end portion 55 that has a flat abutment front end surface 55*a* and an abutment side surface 55*b* connecting to the abutment front end surface 55*a*, as illustrated in the enlarged view of FIG. 1. In the present embodiment, the abutment front end surface 55*a* is formed as a pressing surface that presses the step bottom surface 46*a* of the piston holding member 40, with the step bottom surface 46*a* serving as a pressed surface. By pushing in the plunger operation member 50, the abutment front end surface 55*a* presses the step bottom surface 46*a* of the piston holding member 40, whereby a pushing movement of the plunger P as a whole is achieved.

Furthermore, in the abutment end portion 55 included in the cutout 54, the abutment side surface 55*b* is formed as a tapered surface tapering toward the abutment front end surface 55*a*. In the present embodiment, the abutment side surface 55*b* is the tapered surface inclined at an angle substantially the same as that of the step side surface 46*b*, and a gap G is provided between the abutment side surface 55*b* and the step side surface 46*b*.

Reference numeral 60 refers to a nozzle fitted to the front end portion 23 of the syringe. The nozzle 60 includes a built-in chip 61. The chip 61 is configured to atomize the content C that is pumped through the through hole 20*a* of the syringe 20 before the content C is discharged through an ejection orifice A1. That is to say, the nozzle 60 is capable of ejecting the content C, which has been pumped through the through hole 20*a*, through the ejection orifice A1 in various forms.

Here, a description is given of a method of use of the present embodiment.

Figure 4A:
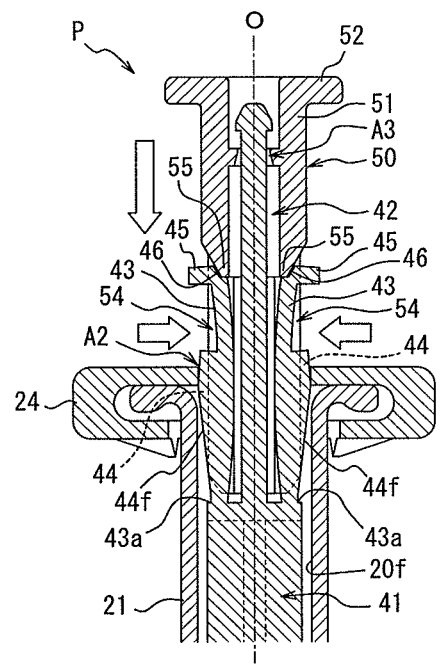
FIG. 4A is an enlarged sectional view illustrating a state where the plunger operation member of FIG. 1 is pushed in for starting a first ejection.

First of all, in the state illustrated in FIG. 1, a user holds the nasal spray dispenser 1 by resting an index finger and a middle finger on the finger rest 24 and by pressing the plunger operation portion 52 with a thumb. After the nozzle 60 of the nasal spray dispenser 1 is inserted into one nostril, the plunger operation member 50 is pushed in. Then, as illustrated in the enlarged view of FIG. 1, the abutment front end surface 55*a* of the plunger operation member 50 is pressed against the step bottom surface 46*a* of the piston holding member 40 that serves as the pressed surface. As a result, the piston holding member 40, together with the plunger operation member 50, is pushed into the syringe 20, as the plunger P. In this regard, each slide projection 44 of the plunger operation member 50 has the inclined surface 44*f* that tapers toward the front end thereof. Accordingly, as illustrated in FIG. 4A, the slide projection 44 may easily enter the syringe 20 though the opening A2 provided in the rear end of the syringe 20.

Figure 4B:
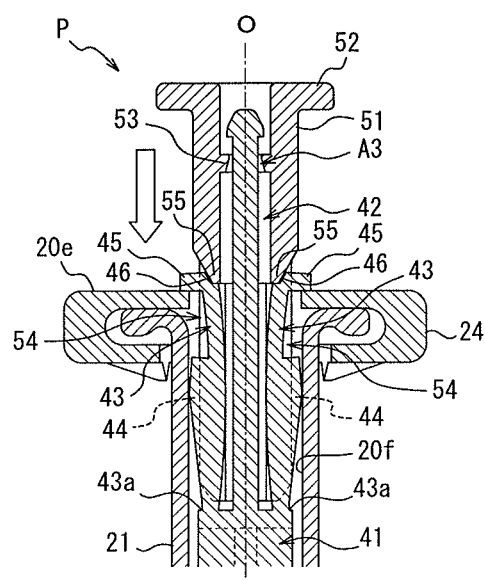
FIG. 4B is an enlarged sectional view illustrating a state where the first ejection is completed in the nasal spray dispenser of FIG. 1.

The piston holding member 40 is also pressed as a result of the abutment front end surface 55*a* coming into contact with the step bottom surface 46*a* of the corresponding arm 43. Accordingly, the step 46 of the arm 43 functions as a restriction portion that restricts inward displacement of the arm 43, and the slide projection 44 of the arm 43 contacts the inner circumferential surface 20*f* of the syringe 20, and therefore, movement of the arm 43 on the side of the free end 43*e* is restrained with respect to the syringe 20. Consequently, as illustrated in FIG. 4B, by the slide projection 44 sliding on the inner circumferential surface 20*f* of the syringe while the arm 43 undergoes flexure deformation starting from the slide projection 44, the pushing of the plunger operation member 50 is allowed. Thus, as illustrated in FIG. 4B, until the protrusion 45 provided in the arm 43 comes into contact with the rear end 20*e* of the syringe 20, a metered quantity of the content C is ejected into the nostril through the ejection orifice A1.

When the protrusion 45 comes into contact with the rear end 20*e* of the syringe 20 to be locked, the plunger operation member 50 may not be pushed anymore. That is to say, the protrusion 45 constitutes the stopper portion by being locked by the rear end 20*e* of the syringe 20. With the above structure, the first ejection is completed while the content C still remains in the room R. The volume of the room R at this time may be appropriately determined in accordance with intended use and may be half the volume of the room R prior to the start of the ejection, for example.

Figure 4C:
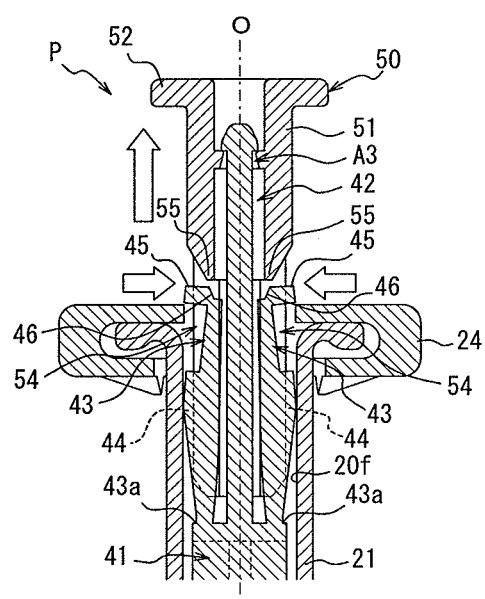
FIG. 4C is an enlarged sectional view illustrating a state where the pushing of the plunger operation member is released for starting a second ejection in the nasal spray dispenser of FIG. 1.

Subsequently, the pushing of the plunger operation member 50 is released. Then, as illustrated in FIG. 4C, restoring force against the aforementioned flexure deformation causes a portion of the arm 43 that is on the side of the free end 43*e* to undergo restoration starting from the slide projection 44. The reason is that, even when the entire arm 43 attempts to restore, a portion of the arm 43 that is on the side of the fixed end 43*a* is still subject to inward deformation starting from the slide projection 44. Accordingly, as illustrated in FIG. 4C, the arm 43 is restored diagonally inward in a manner such that only the side of the free end 43*e* is aligned with the side of the fixed end 43*a* that has undergone inward deformation starting from the slide projection 44. Correspondingly, as illustrated in FIG. 4C, the protrusion 45 is displaced diagonally inward in accordance with the side of the free end 43*e* of the arm 43, and the locking state of the protrusion 45 is released.

In the present embodiment in particular, as described with reference to the enlarged view of FIG. 1, when the plunger operation member 50 is pushed in, the abutment side surface 55*b* of the plunger operation member 50 is restricted by the step side surface 46*b* of the piston holding member 40. With the above structure, the plunger operation member 50 may effectively push the piston holding member 40 in the syringe 20. Furthermore, when the pushing of the plunger operation member 50 is released, due to the restoring force of the free end 43*e* of the arm 43, the abutment side surface 55*b* of the plunger operation member 50 is guided by the step side surface 46*b* of the piston holding member 40 to be displaced. As a result, as illustrated in FIG. 4C, the portion of the arm 43 that is on the side of the free end 43*e* is released from the restriction by the plunger operation member 50 while pushing back the plunger operation member 50, and therefore, is easily restored inward.

Figure 5:
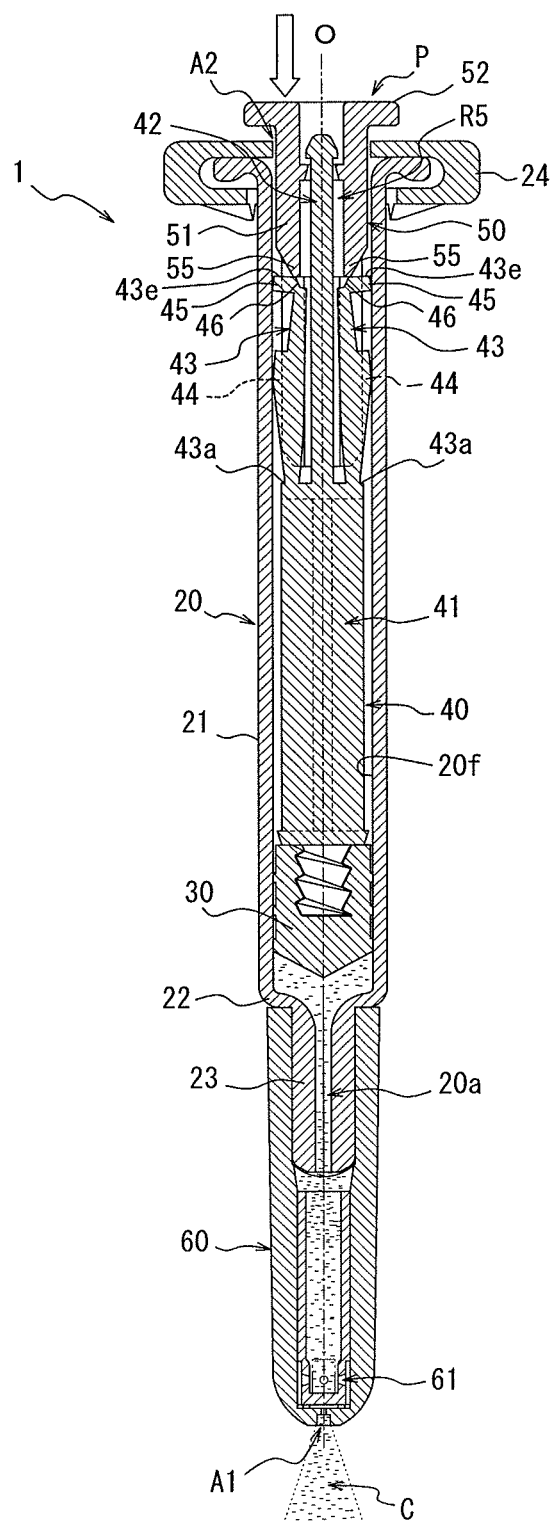
FIG. 5 is a sectional view illustrating a state where the second ejection is completed in the nasal spray dispenser in FIG. 1.

In the present embodiment, as illustrated in FIG. 4C, by pushing in the plunger operation member 50 again after the plunger operation member 50 is pushed back, it is possible to bring the abutment front end surface 55*a* of the plunger operation member 50 into contact with the free end 43*e* of the arm 43 provided in the piston holding member 40, as illustrated in FIG. 5. Accordingly, even after the arm 43 undergoes the restoration starting from the slide projection 44, as illustrated in FIG. 5, the piston holding member 40 may be pushed into the syringe 20 by means of the plunger operation member 50. That is to say, in the present embodiment, after the pushing of the plunger operation member 50 is released, by inserting the nozzle 60 into another nostril and pushing the plunger operation member 50 again, the content C remaining in the room R1 is ejected into the nostril as the second ejection.

Furthermore, in the present embodiment, as described above, since the free end 43e of the arm 43 is tapered at the angle θ, even when the portion of the arm 43 that is on the side of the free end 43e undergoes restoration starting from the slide projection 44, the free end 43e may contact the abutment front end surface 55a of the plunger operation member 50 substantially parallelly. As a result, the piston holding member 40 is pushed smoothly. Value of θ may be appropriately changed depending on a size of the nasal spray dispenser 1 or the like. That is to say, the free end 43e of the arm 43 may be formed as a flat surface parallel to the horizontal line in the initial state as illustrated in FIG. 1.

As described above, according to the present embodiment, the content C may be fractioned for ejection. Furthermore, in the present embodiment, the second ejection is possible when the pushing of the plunger operation member 50 is released, and therefore, it is not necessary to pass the dispenser from one hand to the other at the time of the second ejection. Thus, the user is able to fraction the content C by one-hand operation.

Besides, since the plunger operation member 50 is provided with the inner room R5 for accommodating the shaft 42 and with the cutouts 54 in which the arms 43 are operatively fitted, the present embodiment reduces unsteadiness that occurs when the piston holding member 40 and the plunger operation member 50 are assembled. Thus, according to the present embodiment, the content C may be fractioned for ejection while favorable operability is maintained.

Figure 6:
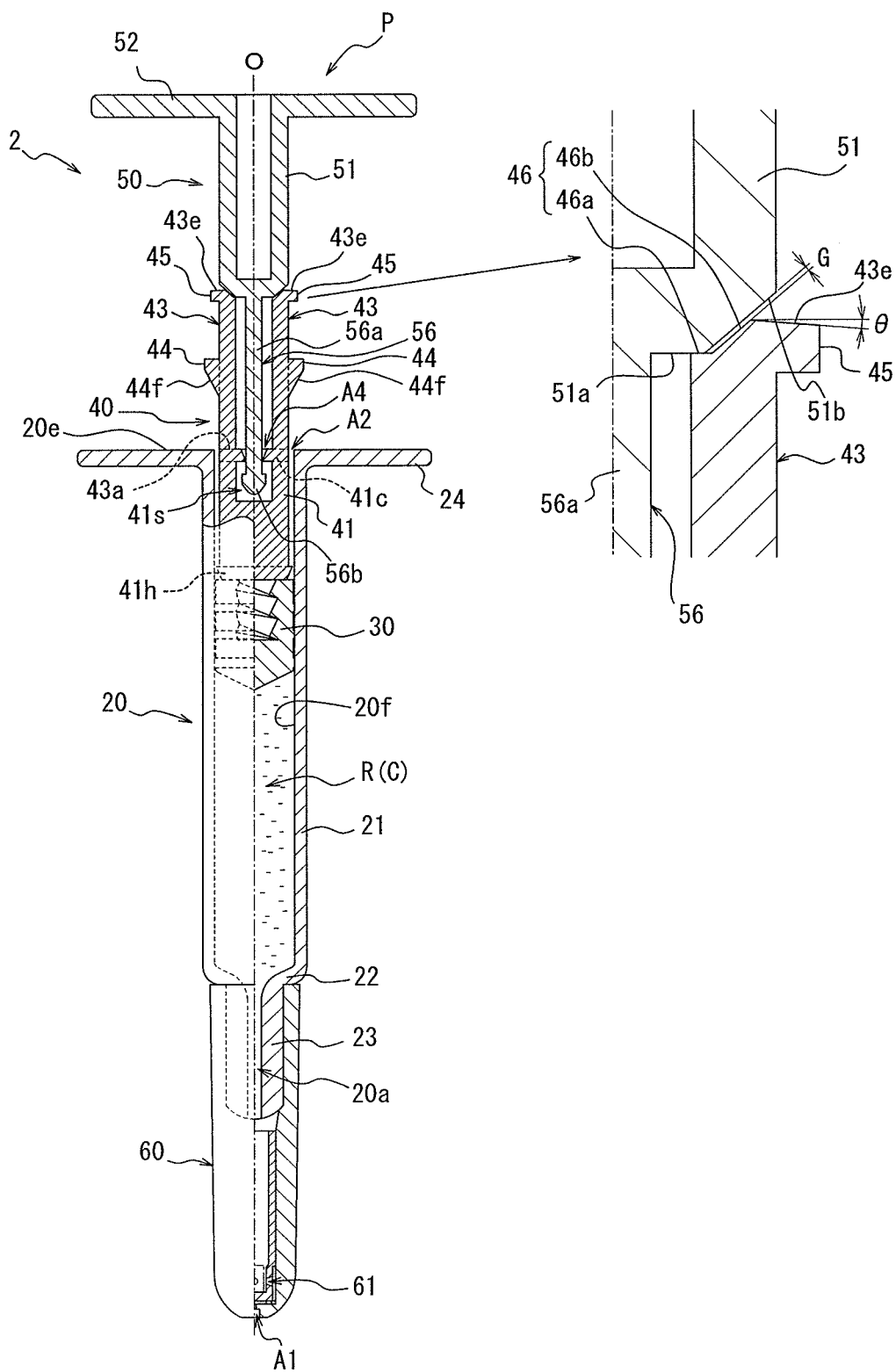
FIG. 6 is a side view taken along a partial section illustrating a nasal spray dispenser that is in an initial state prior to an operation thereof, and a partially enlarged view of the nasal spray dispenser, according to Embodiment 2 of the present invention.
Figure 7:
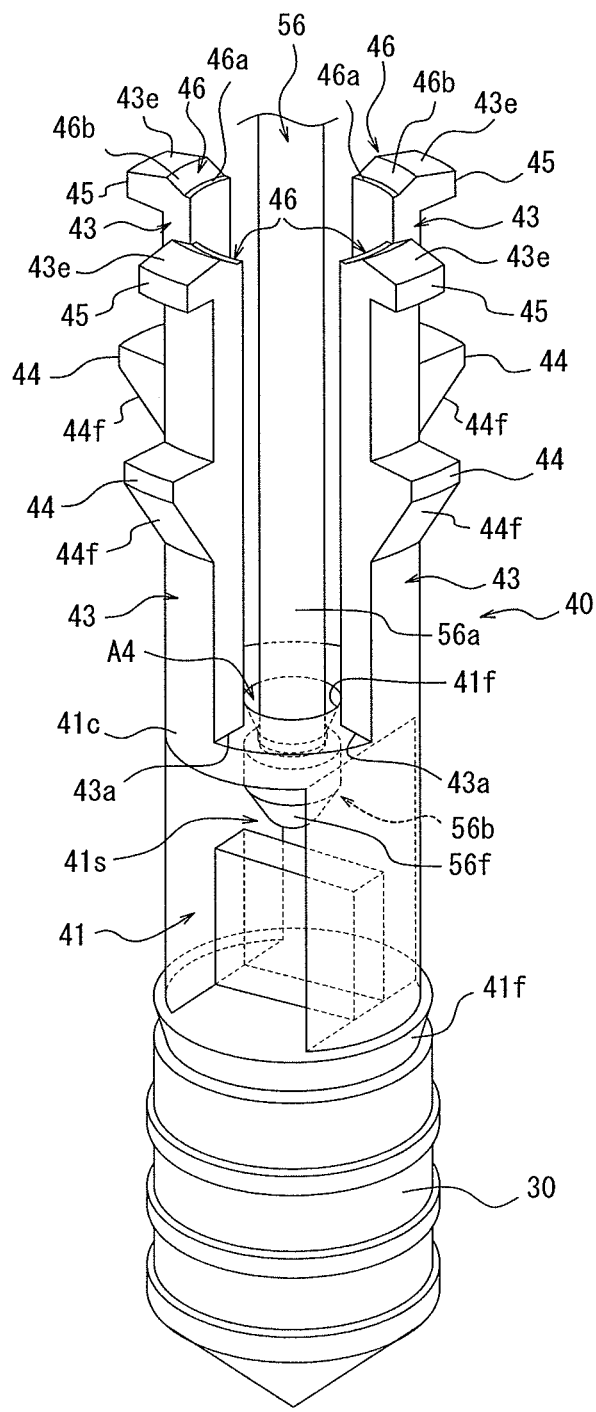
FIG. 7 is an exploded perspective view schematically illustrating a coupling portion of a piston holding member and a plunger operation member that are illustrated in FIG. 6.

Next, FIGS. 6 and 7 illustrate a nasal spray dispenser according to Embodiment 2 of the present invention. In FIG. 6, reference numeral 2 refers to a synthetic resin nasal spray dispenser according to Embodiment 2 of the present invention. In the following, features substantially the same as those of Embodiment 1 are denoted by the same reference numerals. In the present embodiment, the syringe 20 is, although similar, different from that in Embodiment 1 in that the finger rest 24 is integrally formed with the trunk portion 21.

Reference numeral P refers to a plunger configured to be accommodated in the syringe 20. The plunger 20 includes the piston holding member 40 and the plunger operation member 50 disposed in the rear of the piston holding member 40.

The piston holding member 40 includes the piston 30 at the front end portion of the piston holding member 40 that is accommodated in the syringe 20. The piston 30 is made of an elastic material such as rubber or the like and is slidably held on the inner circumferential surface 20f of the trunk portion 21 of the syringe.

Between the syringe 20 and the piston 30, the room R is formed. The room R is configured to be filled with the content C. The content C filled in the room R is pumped to the through hole 20a formed in the front end portion 23 in response to pushing of the plunger P.

The piston holding member 40 is also provided with four arms 43 integrally formed therewith and extending rearward. Each arm 43 is provided with the slide projection 44 and the protrusion 45. The slide projection 44 and the protrusion 45 are arranged in the stated order at a rearward interval along the axis line O. The slide projection 44 includes the inclined surface 44f that tapers toward the front end thereof. With the above structure, the slide projection 44 may enter the syringe 20 though the opening A2 provided in the rear end of the syringe 20 and slide on the inner circumferential surface 20f of the syringe 20, thereby allowing the pushing of the plunger P. Furthermore, the protrusion 45 is locked by the rear end 20e of the syringe 20 so as to restrict the pushing of the plunger P.

In the present embodiment, as illustrated in FIG. 7, the main body 41 of the piston holding member 40 is provided with the four arms 43 integrally formed therewith. Each arm 43 is coupled to the main body 41 via a ring portion 41c. As illustrated in FIG. 7, as the main body 41, for example, the one with an H-shaped cross section that includes two opposing side walls and a horizontal wall bridged between the side walls may be adopted. With the above structure, the portion of the arm 43 that is on the side of the free end 43e may undergo flexure deformation in a manner such that the portion may be deformed and restored, with an end of the arm 43 coupled to the ring portion 41c serving as the fixed end 43a.

Furthermore, in the present embodiment, the protrusion 45 of the arm 43 is formed at the free end 43e of the arm 43 in an integrated manner. Accordingly, in the present embodiment, a rear end surface of the protrusion 45 constitutes the free end 43e of the arm 43. Moreover, in the present embodiment, as illustrated in an enlarged view of FIG. 6, the free end 43e of the arm 43 is tapered and inclined outward (i.e. inclined inward as the free end 43e advances rearward) at an angle θ. Value of θ may be appropriately changed depending on the size of the nasal spray dispenser or the like.

Besides, in the present embodiment, as illustrated in the enlarged view of FIG. 6, the free end 43e of the arm 43 is provided with the step 46. The step 46 also constitutes the free end 43e of the arm 43 and is formed on a side of an inner circumferential surface of the arm 43. In the present embodiment, the step bottom surface 46a of the step 46 is configured to contact an end surface 51a of the main body 51 of the plunger operation member 50 and is formed as the pressed surface that is pressed by the plunger operation member 50. The step side surface 46b connected to the step bottom surface 46a is also formed as the tapered surface that extends outward as the tapered surface advances rearward.

On the other hand, the plunger operation member 50 includes the cylindrical main body 51. As illustrated in the enlarged view of FIG. 6, the end surface (which is referred to below as a "main body end surface") 51a of the main body 51 is formed as the pressing surface that presses the step bottom surface 46a, with the step bottom surface 46a of the piston holding member 40 serving as the pressed surface. By pushing in the plunger operation member 50, the main body end surface 51a presses the step bottom surface 46a of the piston holding member 40, whereby a pushing movement of the plunger P as a whole is achieved. The main body 51 also includes an outer edge 51b of the main body end surface 51a that is formed as a tapered surface corresponding to the step side surface 46b. In the present embodiment, the outer edge 51b is the tapered surface inclined at an angle substantially the same as that of the step side surface 46b, and the gap G is provided between the outer edge 51b and the step side surface 46b.

The plunger operation member 50 also includes a shaft 56 that is connected to the main body 51 in an integrated manner. The shaft 56 includes a shaft body 56a having a diameter smaller than a diameter of the main body end surface 51a. The shaft body 56a extends from the main body end surface 51a toward the front end along the axis line O. The shaft body 56a is provided, at the front end thereof, with a head 56b having a diameter greater than the diameter of the shaft body 56a, in an integrated manner. On the other hand, in the piston holding member 40, space 41s is formed between the main body 41 and the ring portion 41c. As illustrated in FIG. 7, for example, the space 41s is formed by providing an opening in a portion of the horizontal wall of the main body 41. In the space 41s, the head 56b may be accommodated through a through hole A4 formed in the ring portion 41c. The through hole A4 has an inner diameter that is greater than the diameter of the shaft body 56a and smaller than the diameter of the head 56b. As illustrated in FIG. 7, the through hole A4 lets the shaft body 56a penetrate therethrough and also holds the head 56b by preventing the head 56b from slipping off. The head 56b and the inner circumferential surface 41f of the ring portion 41c function as a locking portion that holds the piston holding member 40 to the plunger operation member 50 by preventing the piston holding member 40 from slipping off.

In the present embodiment in particular, as illustrated in FIG. 7, the head 56b includes an inclined surface 56f that tapers toward a front end of the head 56b. The through hole A4 is configured by forming the inner circumferential surface 41f of the ring portion 41c to be an annular tapered surface. The inner circumferential surface 41f has a diameter decreasing toward the front end (the piston 30). With the above structure, the head 56b may be easily assembled to an end surface of the ring portion 41c that is on a side of the piston (i.e. an end surface of the ring portion 41c near the piston 30).

Furthermore, the space 41s forms play that allows the head 56b to be displaced forward and rearward along the axis line O. With the above structure, similarly to Embodiment 1, the piston holding member 40 and the plunger operation member 50 may be displaceably coupled to each other along the axis line O.

In FIG. 6, reference numeral 60 refers to a nozzle fitted to the front end portion 23 of the syringe. The nozzle 60 includes the built-in chip 61 and is capable of ejecting the content C, which has been pumped through the through hole 20a, through the ejection orifice A1.

Here, a description is given of a method of use of the present embodiment.

First of all, in the state illustrated in FIG. 6, the user inserts the nozzle 60 into one nostril, and subsequently, the user pushes in the plunger operation member 50. Then, as illustrated in the enlarged view of FIG. 6, the main body end surface 51a of the plunger operation member 50 presses the step bottom surface 46a of the plunger holding member 40, and accordingly, the piston holding member 40 is pushed in conjunction with the plunger operation member 50. In this regard, since the slide projection 44 of the plunger operation member 50 has the inclined surface 44f that tapers toward the front end thereof, the slide projection 44 may easily enter the syringe 20 though the opening A2 provided in the rear end of the syringe 20.

The main body end surface 51a of the plunger operation member 50 also comes into contact with the step bottom surface 46a of the arm 43 so as to press the step bottom surface 46a. Accordingly, similarly to Embodiment 1, movement of the free end 43e of the arm 43 is restrained with respect to the syringe 20. Consequently, as illustrated in FIG. 4A according to Embodiment 1, by the slide projection 44 of the arm 43 undergoing flexure deformation starting from the slide projection 44 and sliding on the inner circumferential surface 20f of the syringe 20, the pushing of the plunger P is allowed. Thus, as illustrated in FIG. 4B according to Embodiment 1, until the protrusion 45 provided in the arm 43 comes into contact with the rear end 20e of the syringe 20, a metered quantity of the content C is ejected into the nostril through the ejection orifice A1.

When the protrusion 45 provided in the arm 43 comes into contact with the rear end 20e of the syringe 20, the plunger P may not be pushed anymore. Then, the first ejection is completed while the content C still remains in the room R. The volume of the room R at this time may be appropriately determined in accordance with intended use and may be half the volume of the room R prior to the first ejection, for example.

Subsequently, the pushing of the plunger operation member 50 is released. Then, as illustrated in FIG. 4C according to Embodiment 1, restoring force against the aforementioned flexure deformation causes a portion of the arm 43 that is on the side of the free end 43e to undergo restoration starting from the slide projection 44. At this time, the portion of the arm 43 that is on the side of the fixed end 43a is still subject to inward deformation starting from the slide projection 44. Accordingly, as illustrated in FIG. 4C according to Embodiment 1, the portion of the arm 43 that is on the side of the free end 43e is restored diagonally inward to be aligned with the side of the fixed end 43a which has undergone inward deformation starting from the slide projection 44. Correspondingly, as illustrated in FIG. 4C according to Embodiment 1, the protrusion 45 of the arm 43 is displaced diagonally inward in accordance with the side of the free end 43e of the arm 43, and the locking state of the protrusion 45 of the arm 43 is released.

In the present embodiment in particular, as illustrated in the enlarged view of FIG. 6, since the free end 43e of the arm 43 includes the step 46, and the step bottom surface 46a of the step 46 is formed as the pressed surface that is pressed by the plunger operation member 50 and as the tapered surface that releases the portion of the arm 43 that is on the free end 43e, the plunger operation member 50 may be pushed and returned smoothly. Furthermore, in the present embodiment, since the plunger operation member 50 includes the outer edge 51b having the tapered shape corresponding to the piston holding member 40, the plunger operation member 50 may be pushed and returned even more smoothly.

With the above structure, after the pushing of the plunger operation member 50 is released, by pushing in the plunger operation member 50 again, the second ejection is achieved. In the present embodiment, by pushing in the plunger operation member 50 after the plunger operation member 50 is pushed back, the main body end surface 51a of the plunger operation member 50 may come into contact with the free end 43e (a portion of the free end 43e that is located further outward of the step 46 in the radial direction) of the arm 43. Accordingly, after the arm 43 undergoes the restoration starting from the slide projection 44, the piston holding member 40 may be pushed in.

In the present embodiment in particular, since the rear end surface of the free end 43e of the arm 43 is tapered, even when the portion of the arm 43 that is on the side of the free end 43e undergoes restoration starting from the slide projection 44, the free end 43e may contact the main body end surface 51a of the plunger operation member 50 substantially parallelly. As a result, the piston holding member 40 may be pushed smoothly.

Accordingly, after the pushing of the plunger operation member 50 is released and the plunger operation member 50 is pushed back, by inserting the nozzle 60 into the other nostril and pushing in the plunger operation member 50, the content C remaining in the room R1 is ejected into the nostril through the ejection orifice A1 as illustrated in FIG. 5 according to Embodiment 1.

Thus, according to the present embodiment, by the operation similar to that in Embodiment 1, the content C is fractioned for ejection. Furthermore, in the present embodiment, similarly to Embodiment 1, the second ejection is possible when the pushing of the plunger operation member 50 is released, and therefore, it is not necessary to pass the dispenser from one hand to the other at the time of the second ejection. Thus, the user is able to fraction the content C by one-hand operation.

Figure 8:
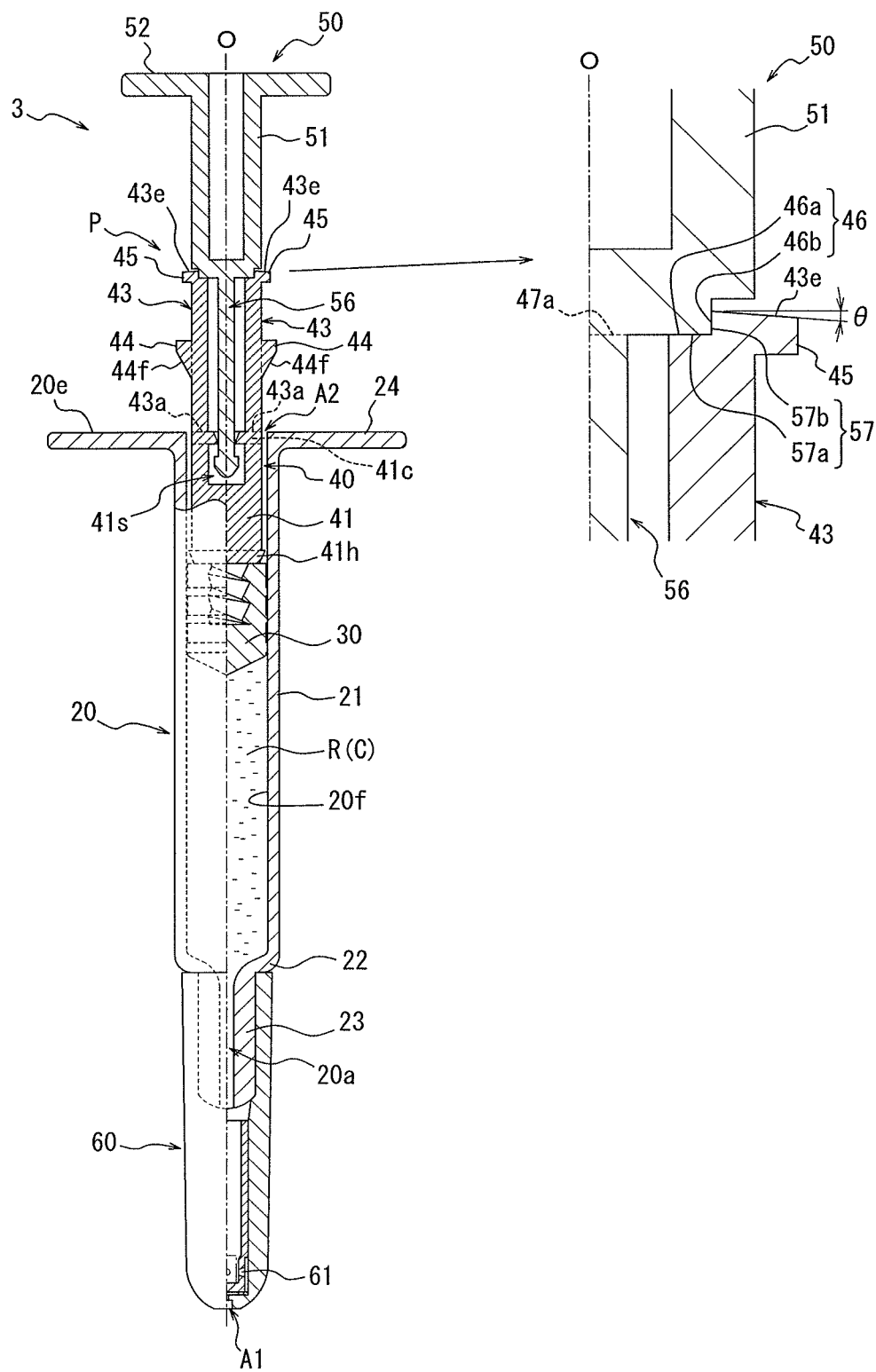
FIG. 8 is a side view taken along a partial section illustrating a nasal spray dispenser that is in an initial state prior to an operation thereof, and a partially enlarged view of the nasal spray dispenser, according to Embodiment 3 of the present invention.

FIGS. 8-12 illustrate a nasal spray dispenser according to Embodiment 3 of the present invention. In FIG. 8, reference numeral 3 refers to a synthetic resin nasal spray dispenser according to Embodiment 3 of the present invention. In the following, configurations substantially the same as those of other embodiments are denoted by the same reference numerals.

Figure 9:
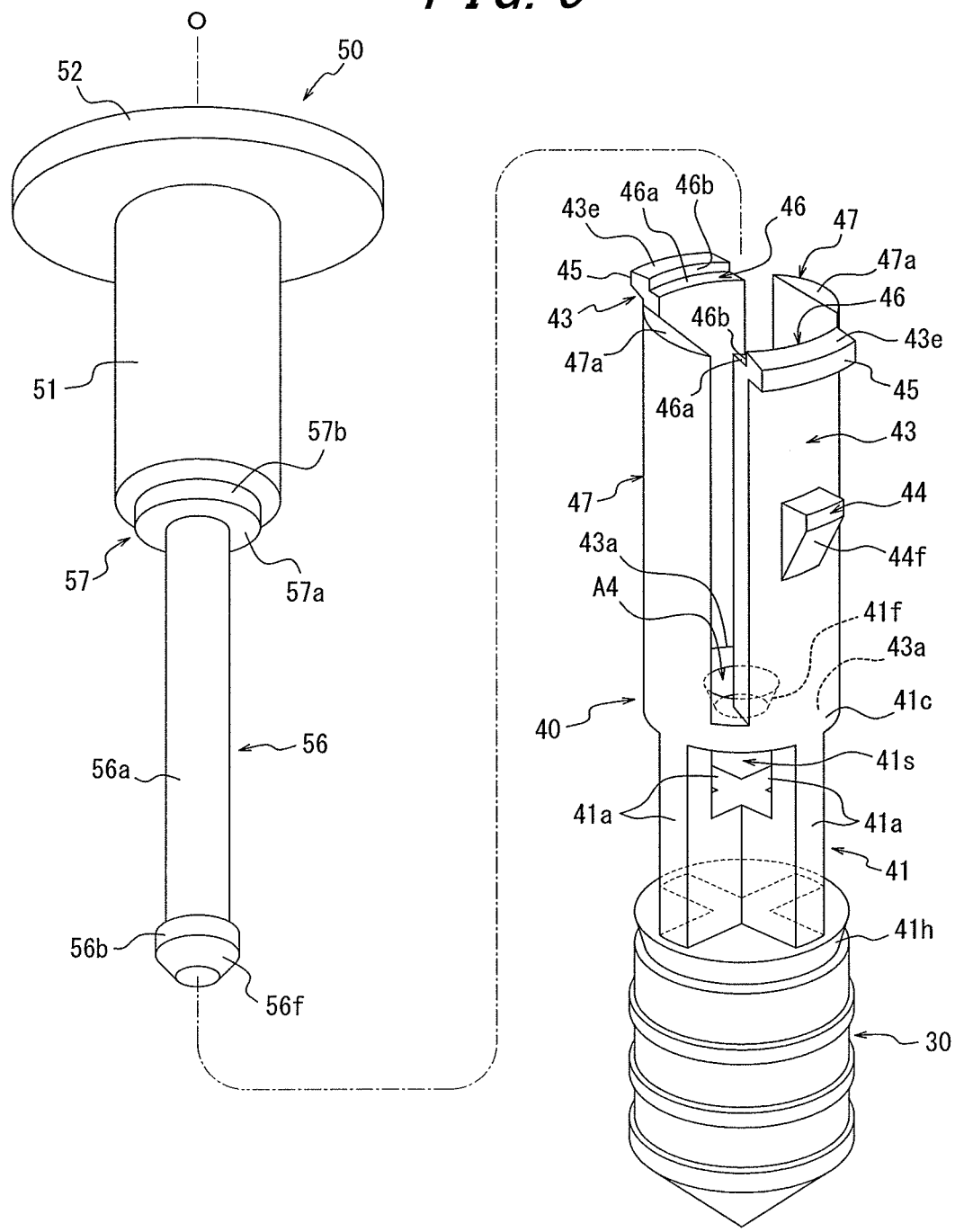
FIG. 9 is a perspective view schematically illustrating a piston holding member of FIG. 8 from a side on which pressure is received and a plunger operation member of FIG. 8 from a side on which pressure is applied.

The present embodiment is a modified example of Embodiment 2. However, in the present embodiment, as illustrated in FIG. 9, the main body 41 of the piston holding member 40 includes the four plate portions 41a and the ring portion 41c in an integrated manner. Furthermore, in the present embodiment, the space 41s is formed by cutting the plate portions 41a. The space 41s communicates with outside through the through hole A4 provided in the ring portion 41c.

The main body 41 of the piston holding member 40 is also provided with two arms 43 integrally formed therewith. The arms 43 are positioned in a manner such that the arms 43 oppose to each other across the through hole A4. Furthermore, as illustrated in FIG. 9, the main body 41 is provided in an integrated manner with two support portions 47 that are formed in a greater thickness than the arms 43, for example. The support portions 47 are positioned in a manner such that the support portions 47 oppose to each other across the through hole A4. The support portions 47 each have an end surface (which is referred to below as a "support portion end surface") 47a that constitutes a flat surface whose length measured from the ring portion 41c corresponds to the step bottom surface 46a provided in the arm 43.

On the other hand, as illustrated in FIG. 9, the plunger operation member 50 includes the main body 51 having a cylindrical shape whose front end portion is closed. In the present embodiment, the front end portion the main body 51 is in the form of a cylindrical convex portion 57. The convex portion 57 includes a flat convex portion end surface 57a and a convex portion side surface 57b connected to the convex portion end surface 57a. Furthermore, in the present embodiment, as illustrated in an enlarged view of FIG. 8, the step 46 of the piston holding member 40 and the convex portion 57 of the plunger operation member 50 are respectively configured as a concave portion 46 and the convex portion 57 that are releasably fitted to each other.

In the present embodiment, as illustrated in the enlarged vie of FIG. 8, the step bottom surface 46a of the piston holding member 40 and the convex portion end surface 57a of the plunger operation member 50 are formed in parallel along the horizontal line. Furthermore, the step side surface 46b of the piston holding member 40 and the convex portion side surface 57b of the plunger operation member 50 are formed in parallel along the axis line O.

As illustrated in the enlarged view of FIG. 8, the convex portion end surface 57a of the plunger operation member 50 is configured to come into contact with the step bottom surface 46a and the support portion end surface 47a of the piston holding member 40. With the above structure, when the plunger operation member 50 is pushed in, the convex portion end surface 57a presses the step bottom surface 46a and the support portion end surface 47a of the piston holding member 40, both of which serve as the pressed surface, whereby a pushing movement of the plunger P as a whole is achieved. That is to say, the convex portion end surface 57a of the plunger operation member 50 constitutes the pressing surface that restrains the arm 43 and that presses the step bottom surface 46a of the piston holding member 40.

On the other hand, as illustrated in the enlarged view of FIG. 8, the convex portion side surface 57b of the plunger operation member 50 is configured to come into slide contact with the step side surface 46b of the piston holding member 40. With the above structure, when inserted along the step side surface 46b of the piston holding member 40, the convex portion side surface 57b of the plunger operation member 50 prevents inward deformation of the arm 43, and when the plunger operation member 50 is returned, the mutual contact is released. That is to say, the step side surface 46b of the piston holding member 40 and the convex portion side surface 57b of the plunger operation member 50 constitute the aforementioned restriction portion and also constitutes a stopper releasing portion that allows the locking state of the protrusion 45 and the rear end 20e of the syringe 20 to be released by releasing the displacement restriction on the protrusion 45.

Figure 10:
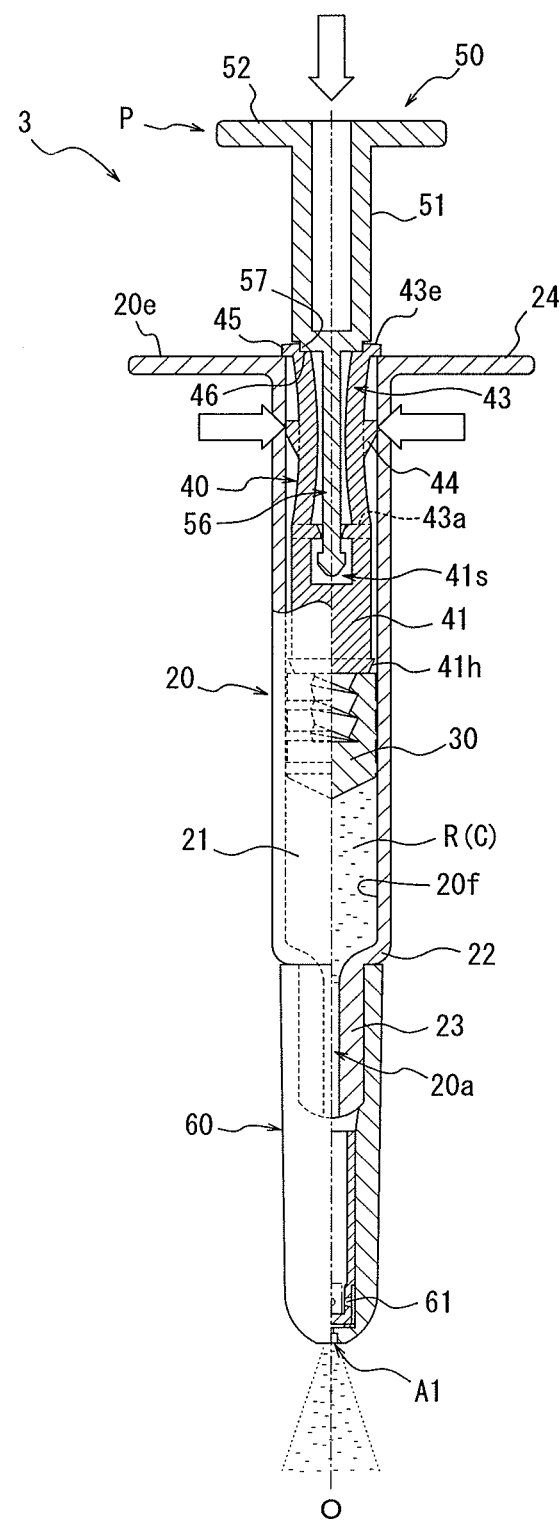
FIG. 10 is a side view taken along a partial section illustrating a state where the plunger operation member of FIG. 8 is pushed in and where a first ejection is completed.

Here, a description is given of a method of use of the present embodiment. Basic operation of the present embodiment is substantially the same as that in Embodiment 2. From the state illustrated in FIG. 8, the user pushes the plunger operation member 50. Then, as illustrated in FIG. 10, until the protrusion 45 provided in the piston holding member 40 comes into contact with the rear end 20e of the syringe 20, the content C is ejected.

Figure 11:
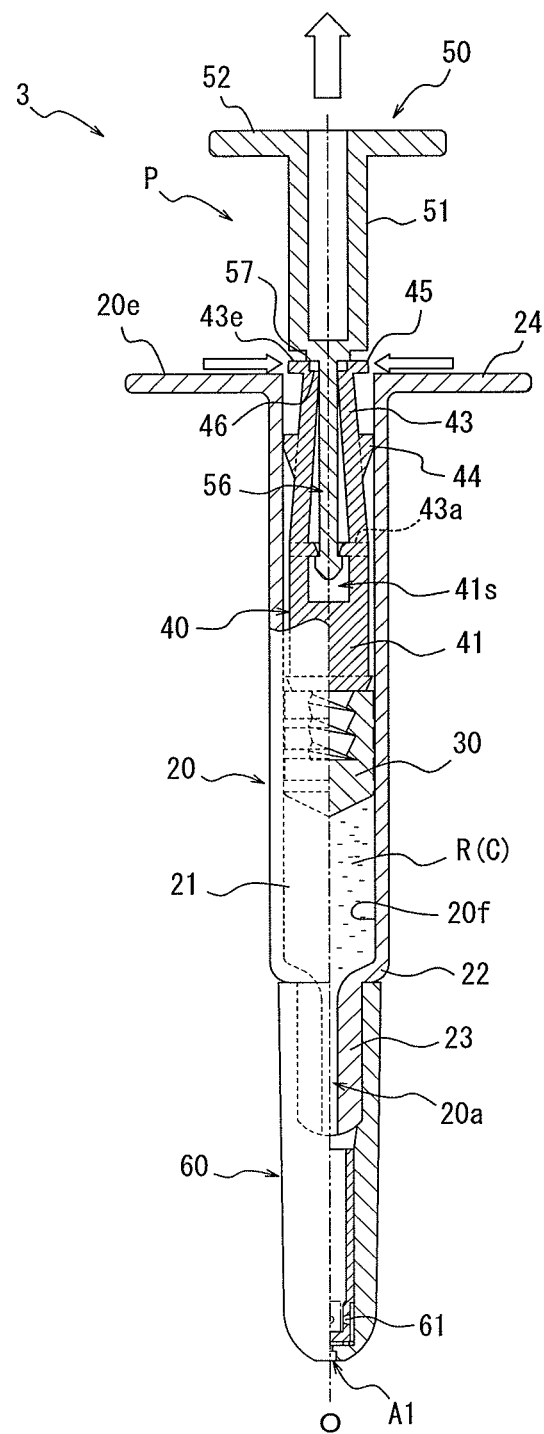
FIG. 11 is a side view taken along a partial section illustrating a state where the plunger operation member is pulled back for a second ejection in the nasal spray dispenser of FIG. 8.

However, at this time, as illustrated in the enlarged view of FIG. 8, the step side surface 46b (which is referred to below as the "stopper releasing portion 46b") of the arm 43 is in contact with the convex portion side surface 57b (which is referred to below as the "stopper releasing portion 57b") of the plunger operation member 50, and therefore, inward deformation of the arm 43 is prevented. Accordingly, even when the pushing of the plunger operation member 50 is released, the locking of the protrusion 45 and the rear end 20e of the syringe 20 is not released. In view of the above, in the present embodiment, after the protrusion 45 of the piston holding member 40 comes into contact with the rear end 20e of the syringe 20, plunger operation member 50 is pulled back from the arm 43. Then, the contact of the stopper releasing portion 46b and the stopper releasing portion 57b is released, and the free end 43e of the arm 43 is released from restraint. As a result, as illustrated in FIG. 11, due to restoring force generated on the side of the free end 43e of the arm 43, the locking state of the protrusion 45 and the rear end 20e of the syringe 20 is released.

Figure 12:
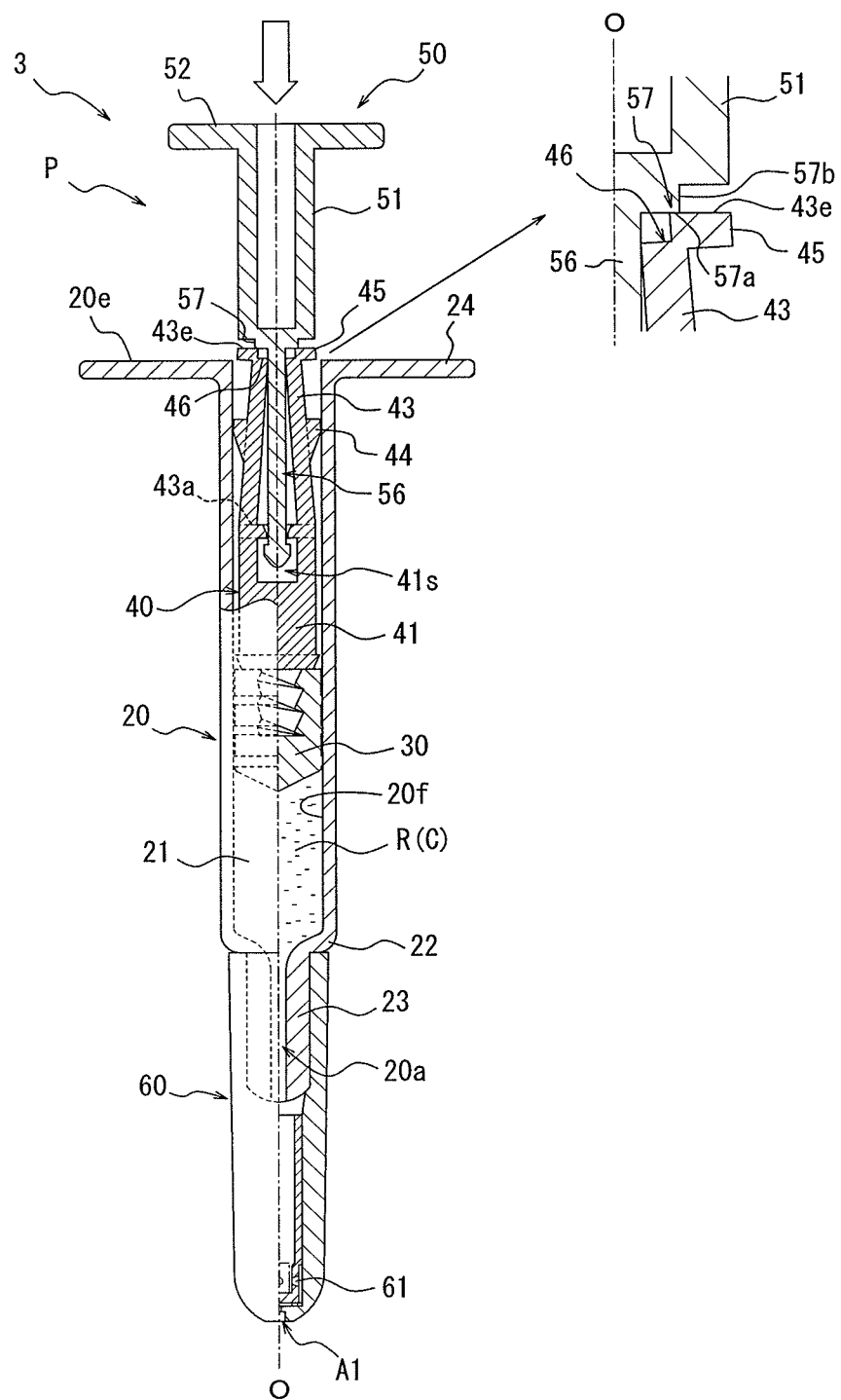
FIG. 12 is a side view taken along a partial section illustrating a state immediately before the pushing of the plunger operation member is started for the second ejection in the nasal spray dispenser of FIG. 8, and a partially enlarged view of the nasal spray dispenser.

As illustrated in FIG. 12, by pushing in the plunger operation member 50 again after the plunger operation member 50 is pushed back, it is possible to bring the convex portion end surface 57a of the plunger operation member 50 into contact with the free end 43e of the arm 43, as illustrated in an enlarged view of FIG. 12. With the above structure, after the plunger operation member 50 is pulled back, by pushing the plunger operation member 50 again, the second ejection is achieved. In the present embodiment, since the free end 43e of the arm 43 is tapered at the angle θ, as illustrated in the enlarged view of FIG. 12, the convex portion end surface 57a of the plunger operation member 50 is allowed to be in contact perpendicularly with the free end 43e of the arm 43.

As described above, according to the present embodiment, inward deformation of the arm 43 is prevented because the inside of the arm 43 contacts the plunger operation member 50. Accordingly, until the plunger operation member 50 is pulled back from the inside of the arm 43, the locking of the protrusion 45 is not released. Therefore, even when the pushing of the plunger operation member 50 is loosened or released during the first ejection, the arm 43 remains capable of being locked with respect to the syringe 20. Accordingly, even when the pushing of the plunger operation member 50 is stopped in the middle of the first ejection, the quantity is precisely metered for the first ejection.

Furthermore, as in the present embodiment, by providing the arm 43 and the plunger operation member 50 respectively with the concave portion (the step 46) and the convex portion (the convex portion 57) that are configured to be releasably fitted to each other, and by configuring the concave portion bottom surface (the step bottom surface 46a) and the convex portion end surface 57a as the concave-convex fitting portion and configuring the concave portion side surface (the step side surface 46b) and the convex portion side surface 57b as the stopper releasing portion, positioning of the plunger P, after the dispenser is used for the first time, is achieved with the simple and plain structure.

Various modifications may be made to the above description. For example, although in the present embodiment the step bottom surface 46a and the convex portion end surface 57a are formed to be flat with respect to the horizontal line, the step bottom surface 46a and the convex portion end surface 57a may be formed otherwise as long as at least the pushing of the piston holding member 40 is achieved. Accordingly, the step bottom surface 46a and the convex portion end surface 57a are not limited to the flat surfaces and may be configured by inclined surfaces.

Figure 13:
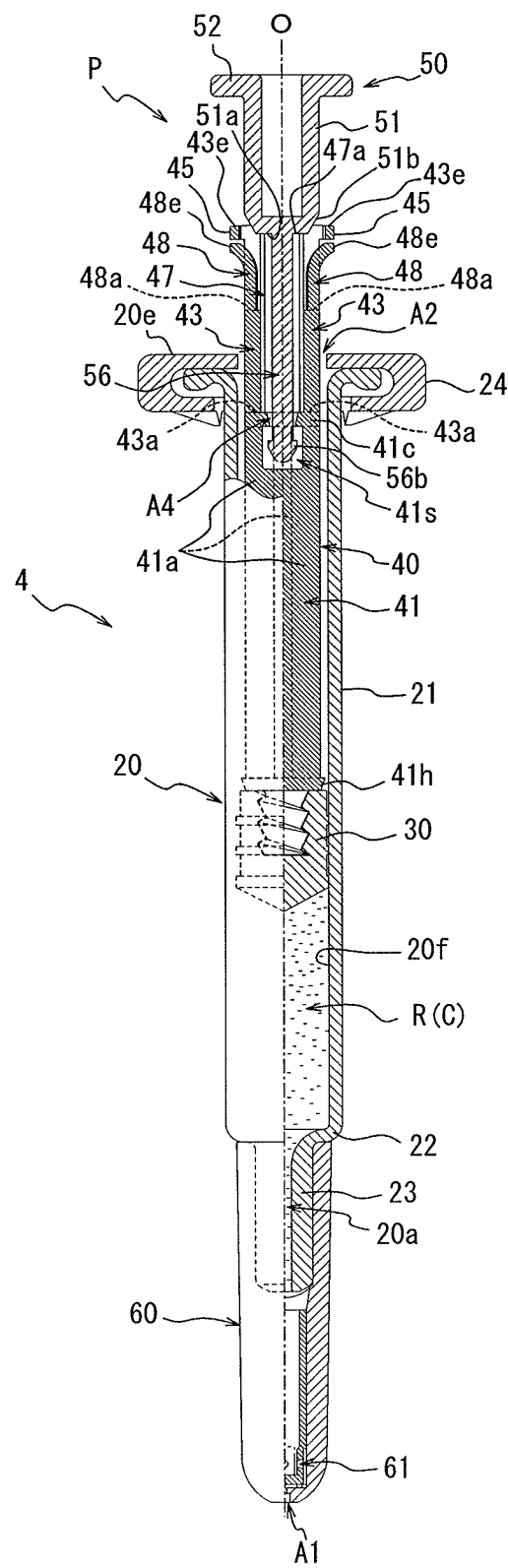
FIG. 13 is a side view taken along a partial section illustrating a nasal spray dispenser that is in an initial state prior to an operation thereof, according to Embodiment 4 of the present invention.

FIGS. 13-16 illustrate a nasal spray dispenser according to Embodiment 4 of the present invention. In the following, configurations substantially the same as those of other embodiments are denoted by the same reference numerals. In FIG. 13, reference numeral 4 refers to a synthetic resin nasal spray dispenser according to Embodiment 4 of the present invention.

Reference numeral P refers to a synthetic resin plunger accommodated in the syringe 20. The plunger P includes the piston holding member 40 and the plunger operation member 50 disposed in the rear of the piston holding member 40.

Figure 14:
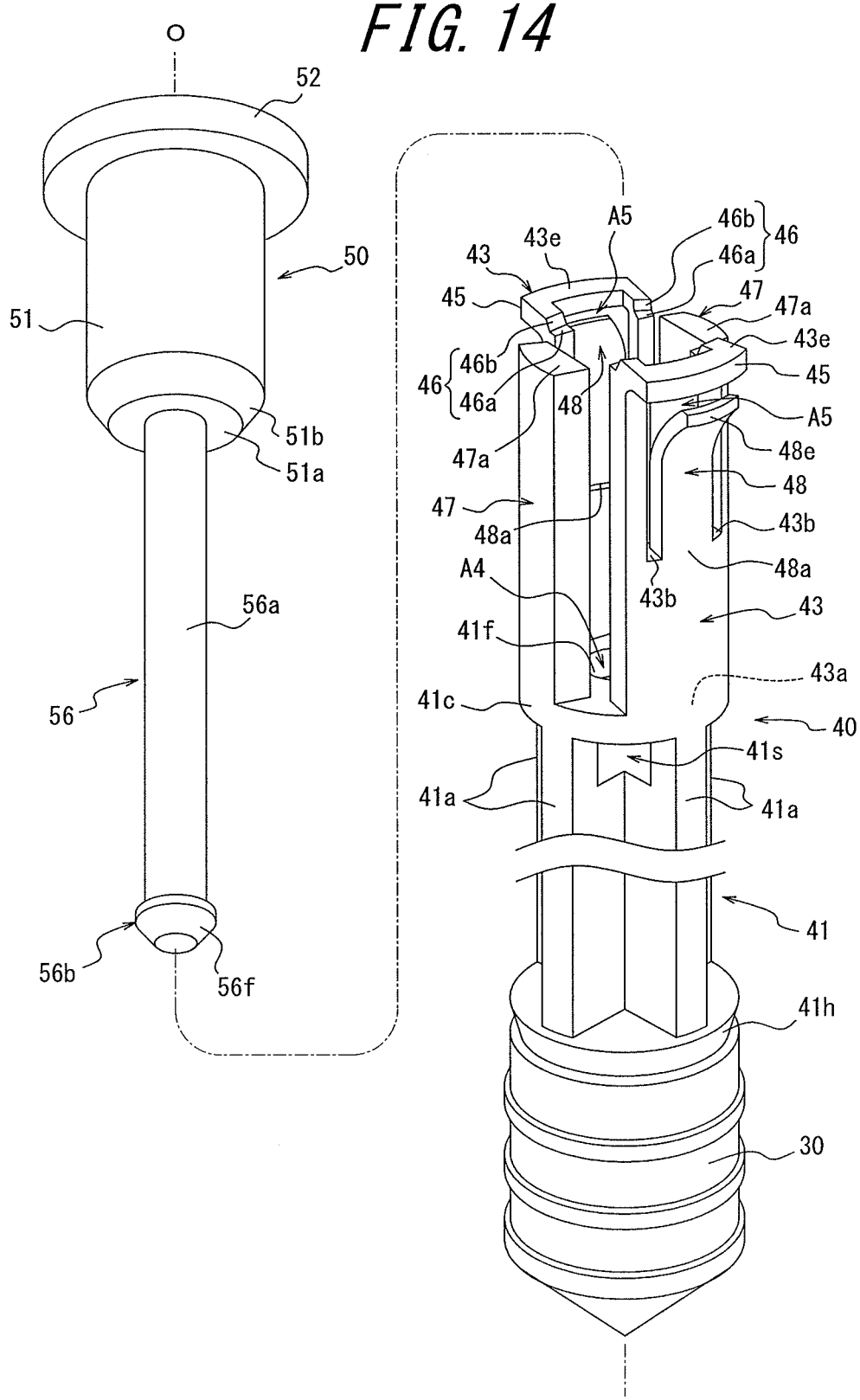
FIG. 14 is a perspective view schematically illustrating a piston holding member of FIG. 13 from a side on which pressure is received and a plunger operation member of FIG. 13 from a side on which pressure is applied.

The piston holding member 40 includes the main body 41 configured to hold the piston 30. The main body 41 includes the elongate four plate portions 41a and the ring portion 41c in an integrated manner. The ring portion 41c is provided with the through hole A4. The through hole A4 communicates with the open space 41s that is formed by cutting the plate portions 41a. As illustrated in FIG. 14, the through hole A4 is formed by a tapered surface constituted by the inner circumferential surface 41f of the ring portion 41c whose diameter decreases towards the front end (the piston 30).

The main body 41 is provided with the two arms 43 integrally formed therewith. The arms 43 are positioned in a manner such that the arms 43 oppose to each other across the through hole A4. As illustrated in FIG. 14, the arms 43 each have a plate shape and extend rearward from the ring portion 41c along the axis line O. Each arm 43 may be deformed inward in the radial direction (the direction perpendicular to the axis line O) from the fixed end 43a, when loaded with external force. The arm 43 may also be restored to the initial position when the load is released. With the above structure, the free end 43e of the arm 43 may be displaced inward in the radial direction and restored to the initial position.

In the present embodiment, in the arm 43 provided in the main body 41 of the piston holding member 40, an elastic tongue piece 48, instead of the slide projection 44, is also provided. As illustrated in FIG. 14, the elastic tongue piece 48 is arranged in an opening A5 formed in the arm 43. The elastic tongue piece 48 has a fixed end 48a formed in an integrated manner from, among edge portions constituting the opening A5, an opening edge portion 43b that is on the side of the fixed end 43a of the arm 43. As illustrated in FIG. 14, the fixed end 48a of the elastic tongue piece 48 constitutes the same surface as an outer surface of the arm 43. In the present embodiment, the arm 43 is formed in a small thickness and therefore, is easily deformed and restored. The elastic tongue piece 48 is formed in a smaller thickness than the arm 43.

The elastic tongue piece 48 is curved outward in the radial direction as the elastic tongue piece 48 advances toward the free end 43e of the arm 43. Accordingly, an end 48e of the elastic tongue piece 43 is oriented outward in the radial direction. As illustrated in FIG. 13, for example, the two ends 48e are arranged to opposed to each other about the axis line O and have an interval between outermost diameters thereof in the radial direction that is greater than the inner diameter of the syringe 20 (which is the same as the diameter of the opening A2 provided in the rear end of the syringe in the present embodiment). When the elastic tongue piece 48 comes into contact with the opening A2 provided in the rear end of the syringe 20, a portion of the elastic tongue piece 48 that is on the side of the end 48e serving as the free end undergoes flexure deformation starting from the fixed end 48a. As a result, the elastic tongue piece 48 enters the syringe 20 and, by means of the end 48e, slides on the inner circumferential surface 20f of the syringe.

In the present embodiment, the elastic tongue piece 48 is curved outward toward the end 48e as illustrated in FIG. 13, for example. With the above structure, the elastic tongue piece 48 may easily enter the syringe 20 though the opening A2 provided in the rear end of the syringe 20.

Furthermore, each arm 43 is also provided, on the side of the free end 43e thereof, with the protrusion 45 in an integrated manner. The rear end surface of the protrusion 45 constitutes the free end 43e of the arm 43. In the present embodiment, the free end 43e of the arm 43 forms a flat surface that is parallel with the horizontal line. However, as in other embodiments, as illustrated in the enlarged view of FIG. 8 according to Embodiment 3, the free end 43e may be tapered and inclined at an angle θ with respect to the horizontal line.

In the present embodiment, the elastic tongue piece 48 is formed in a manner such that a portion of the elastic tongue piece 48 that is on the side of the end 48e (a portion of the elastic tongue piece 48 that is on the side of the free end) is positioned closest to the protrusion 45. Furthermore, in the present embodiment, as illustrated in FIG. 14, the arm is provided, inside thereof, with the step 46. The step 46 is formed on the inner side of the arm 43. In the present embodiment, the step 46 includes the flat step bottom surface 46a and the step side surface 46b connected to the step bottom surface 46a. In the present embodiment, the step side surface 46b is also formed as the tapered surface that is inclined rearward and outward.

The main body 41 of the piston holding member 40 is also provided with the two support portions 47 integrally formed therewith. The support portions 47 are positioned in a manner such that the support portions 43 oppose to each other across through hole A4. The support portion end surfaces 47a each constitute a flat surface whose length measured from the ring portion 41c corresponds to the step bottom surface 46a provided in the arm 43.

On the other hand, the plunger operation member 50 includes the main body 51 that is provided at the rear end thereof in an integrated manner with the plunger operation portion 52 for the user to push in the plunger P. As illustrated in FIG. 14, the main body 51 has a cylindrical shape. The front end portion of the main body 51 forms a pressing portion that presses the piston holding member 40. The pressing portion is constituted by the flat main body end surface 51a and the outer edge 51b of the main body end surface 51a that is connected to the main body end surface 51a. When the plunger operation member 50 is pushed in, the main body end surface 51a presses the step bottom surface 46a and the support portion end surface 47a of the piston holding member 40, whereby the pushing movement of the plunger P as a whole is achieved. The outer edge 51b of the main body end surface 51a is formed as a tapered surface tapered toward the main body end surface 51a. In the present embodiment, the outer edge 51b is the tapered surface inclined at an angle substantially the same as that of the step side surface 46b of the piston holding member 40, and a gap provided between the outer edge 51b and the step side surface 46b.

The main body 51 of the plunger operation member 50 is also provided with the shaft 56 in an integrated manner. The shaft 56 includes the shaft body 56a having a diameter smaller than the diameter of the main body end surface 51a. The shaft body 56a extends forward from the main body end surface 51a along the axis line O. The shaft body 56a is provided, at a front end thereof, with the head 56b having a diameter greater than the diameter of the shaft body 56a, in an integrated manner. As illustrated in FIG. 14, the head 56b includes the inclined surface 56f that tapers toward the front end of the head 56b. The shaft 56 is fitted to and held by the through hole A4 formed in the piston holding member 40. The through hole A4 has an inner diameter that is greater than the diameter of the shaft body 56a and smaller than the diameter of the head 56b. As illustrated in FIG. 13, the through hole A4 lets the shaft body 56a penetrate therethrough and also holds the head 56b by preventing the head 56b from slipping off. The head 56b and the inner circumferential surface 41f of the ring portion 41c hold the piston holding member 40 to the plunger operation member 50 by preventing the piston holding member 40 from slipping off. In the present embodiment in particular, the inner circumferential surface 41f of the ring portion 41c is configured by a tapered surface whose diameter increases rearward. With the above structure, the head 56b may be easily assembled to the end surface of the ring portion 41c that is on the side of the front end (i.e. the end surface of the ring portion 41c near the piston 30). The open space 41s, which is formed by cutting the plate portions 41a, defines play space in which the head 56b is displaceable forward and rearward along the axis line O. With the above structure, the piston holding member 40 and the plunger operation member 50 may be displaceably coupled to each other along the axis line O.

The piston 30 is provided in the front end portion of the main body 41 and accommodated in the syringe 20. The piston 30 is made of an elastic material such as rubber or the like and is slidably held on the inner circumferential surface 20f of the trunk portion 21 of the syringe.

Between the syringe 20 and the piston 30, the room R is formed. The room R is configured to be filled with the content C. The content C filled in the room R is pumped to the through hole 20a formed in the front end portion 23 in response to pushing of the piston 30.

Reference numeral 60 refers to the nozzle fitted to the front end portion 23 of the syringe. The nozzle 60 includes the built-in chip 61 and is capable of ejecting the content C, which has been pumped through the through hole 20a, through the ejection orifice A1.

Figure 15A:
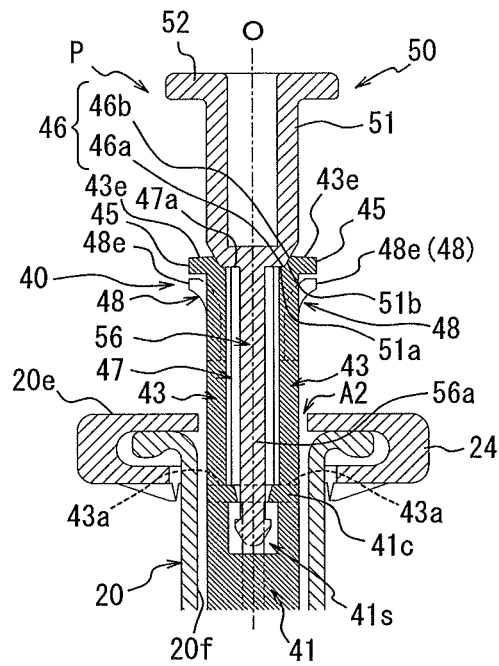
FIG. 15A is an enlarged sectional view taken along another section illustrating a state immediately before the plunger operation member of FIG. 13 is pushed in for starting a first ejection.
Figure 15B:
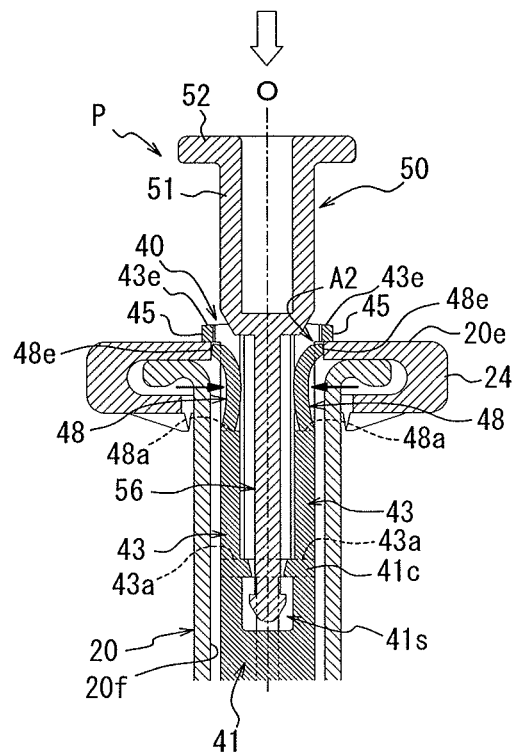
FIG. 15B is an enlarged sectional view illustrating a state where the first ejection is completed in the nasal spray dispenser of FIG. 13 as viewed from one side.

Here, a description is given of a method of use of the present embodiment. Basic operation of the present embodiment is substantially the same as those in other embodiments. From the state illustrated in FIG. 13, the user pushes the plunger operation member 50. Then, as illustrated in FIG. 15A, the main body end surface 51a of the plunger operation member 50 presses the step bottom surface 46a and the support portion end surface 47a of the piston holding member 40. As a result, the piston holding member 40, together with the plunger operation member 50, is pushed into the syringe 20. At this time, the elastic tongue piece 48 of the piston holding member 40 is curved outward as it advances toward the free end 43e of the arm 43, and the end 48e of the elastic tongue piece 48 is oriented outward in the radial direction. Accordingly, as illustrated in FIG. 15B, the elastic tongue piece 48 may enter the syringe 20 through the opening A2 provided in the rear end of the syringe.

Furthermore, since the main body end surface 51a of the plunger operation member 50 presses the step bottom surface 46a of the arm 43 so as to restrain the free end 43e of the arm 43 with respect to the syringe 20, the elastic tongue piece 48, when entering through the opening A2 provided in the rear end of the syringe 20, undergoes flexure deformation starting from the free end 48a connected to the arm 43. Accordingly, an end 48e of the elastic tongue piece 48 is allowed to slide on the inner circumferential surface 20f of the syringe 20. Thus, as illustrated in FIG. 15B, because the plunger P is pushed without being obstructed by the elastic tongue piece 48, until the protrusion 45, following the elastic tongue piece 48, of the arm 43 comes into contact with the rear end 20e of the syringe 20, a metered quantity of the content C is ejected through the ejection orifice A1.

When the protrusion 45 comes into contact with the rear end 20e of the syringe 20, the plunger P may not be pushed in anymore. Then, as in other embodiments, the first ejection is completed while the content C still remains in the room R.

Figure 15C:
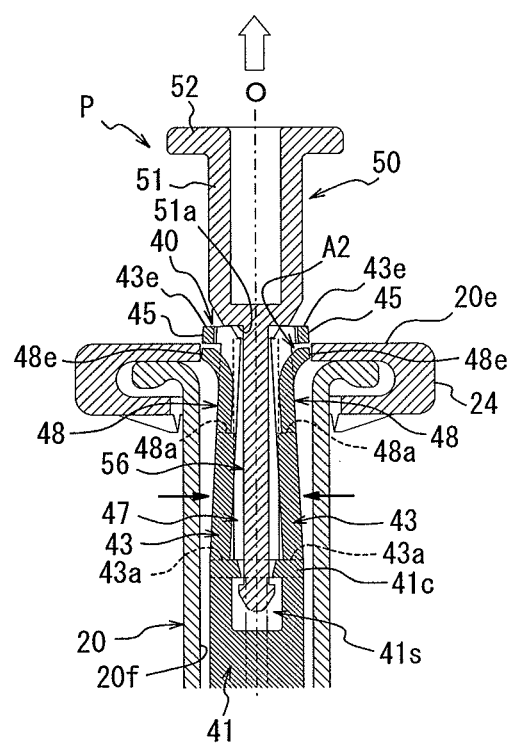
FIG. 15C is an enlarged sectional view illustrating a state where the pushing of the plunger operation member is released for starting a second ejection in the nasal spray dispenser of FIG. 13 as viewed from one side.

Subsequently, when the pushing of the plunger operation member 50 is released, as illustrated in FIG. 15C, the plunger operation member 50 is pushed back. Accordingly, the free end 43e of the arm 43 is released from restraint. As a result, restoring force of the arm 43 based on the elastic tongue piece 48 that is in contact with the inner circumferential surface 20f of the syringe 20 causes the arm 43, except for the elastic tongue piece 48, to be deformed inward. At this time, as illustrated in FIG. 15C, the arm 43a undergoes diagonally inward deformation starting from the fixed end 43a. Correspondingly, as illustrated in FIG. 15C, the locking state of the protrusion 45 is released as a result of the protrusion 45 being displaced diagonally inward in accordance with the side of the free end 43e of the arm 43.

In the present embodiment in particular, as illustrated in FIG. 15A, when the plunger operation member 50 is pushed in, the outer edge 51b of the main body end surface 51a is restricted by the step side surface 46b of the piston holding member 40. With the above structure, the plunger operation member 50 may effectively push the piston holding member 40 inside the syringe 20. When the pushing of the plunger operation member 50 is released, the outer edge 51b of the main body end surface 51a is guided by the step side surface 46b of the piston holding member 40 to be deformed. As a result, the portion of the arm 43 that is on the side of the free end 43e is released from the restriction by the plunger operation member 50 while pushing back the plunger operation member 50, and therefore, the deformation of the arm 43 is easily restored inward.

Figure 16:
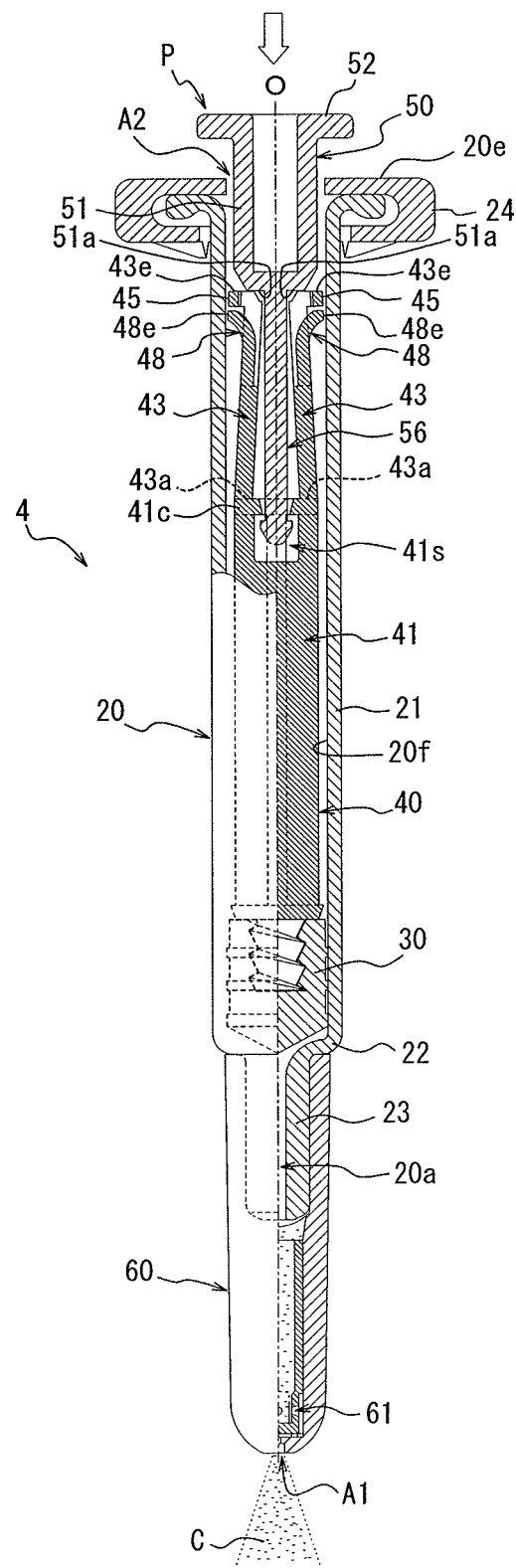
FIG. 16 is a side view taken along a partial section illustrating a state where the second ejection is completed in the nasal spray dispenser of FIG. 13.

As illustrated in FIG. 16, by pushing in the plunger operation member 50 again after the plunger operation member 50 is pushed back, the main body end surface 51a of the plunger operation member 50 may come into contact with the free end 43e of the arm 43. With the above structure, after the pushing of the plunger operation member 50 is released, by pushing in the plunger operation member 50 again, as illustrated in FIG. 16, the second ejection is achieved.

According to the present embodiment in particular, the state where the protrusion 45 provided in the arm 43 is locked with respect to the syringe 20 is released by the restoring force of the arm 43 based on the elastic tongue piece 48 provided in the arm 43. Accordingly, wherever the elastic tongue piece 48 is positioned with respect to the arm 43, by releasing pressure of the plunger operation member 50 to the free end 43e of the arm 43, the state where the arm 43 is locked by the syringe 20 is released. For example, as in the present embodiment, the elastic tongue piece 48 may be arranged in a position closest to the protrusion 45. In the above circumstance, the elastic tongue piece 48 is not deformed until immediately before the arm 43 is locked by the syringe 20 by the protrusion 45, and even when the pushing of the plunger P is loosened or released during the first ejection, the arm 43 remains capable of being locked with respect to the syringe 20. Accordingly, by arranging the elastic tongue piece 48 in the position closest to the protrusion 45, even when the pushing of the plunger P is stopped in the middle of the first ejection, the quantity is precisely metered for the first ejection.

Various modifications may be made to the above description. For example, although, when arranged in the opening A5 formed in the arm 43 as in the present embodiment, the elastic tongue piece 48 may prevent the entire dispenser from being provided with a large diameter, the elastic tongue piece 48 does not need to be arranged in the opening A5 and may also extend from the outer surface of the arm 43.

FIGS. 17-23 illustrate a nasal spray dispenser according to Embodiment 5 of the present invention and a modified example of the nasal spray dispenser. In the following, configurations substantially the same as those of other embodiments are denoted by the same reference numerals.

Figure 17A:
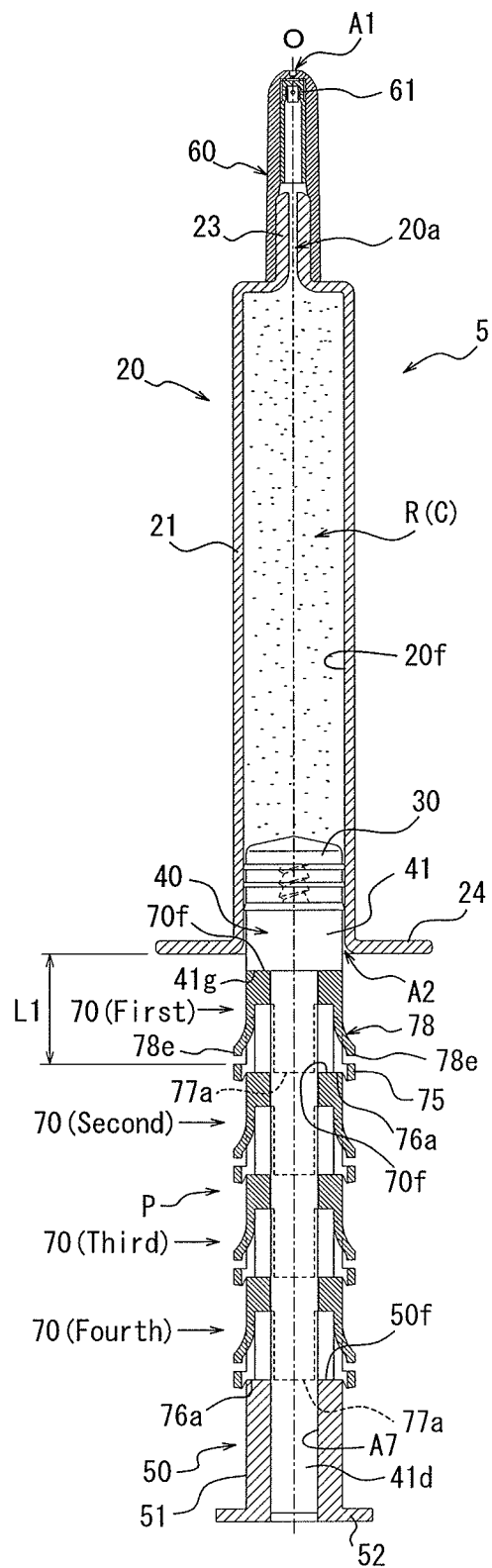
FIG. 17A is a side view taken along a partial section illustrating a cartridge-type nasal spray dispenser that is in an initial state prior to an operation thereof, according to Embodiment 5 of the present invention.

In FIG. 17A, reference numeral 5 refers to a synthetic resin nasal spray dispenser according to Embodiment 5 of the present invention. The present embodiment is an application example of Embodiment 4. The main body 41 of the piston holding member 40 includes a shaft portion 41d integrally formed therewith and extending rearward. In the present embodiment, the shaft portion 41d is in the form of a round bar. However, according to the present invention, the shaft portion 41d may have any cross sectional shape such as a rectangular shape.

Figure 18:
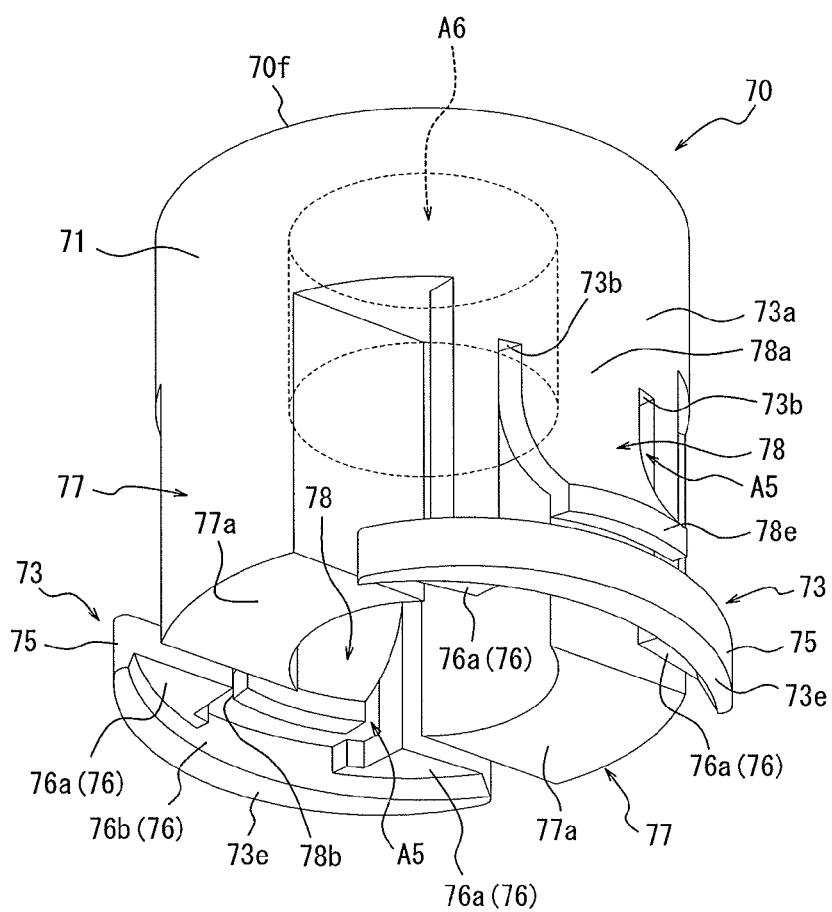
FIG. 18 is a perspective view schematically illustrating an intermediate member of FIG. 17A.
Figure 19:
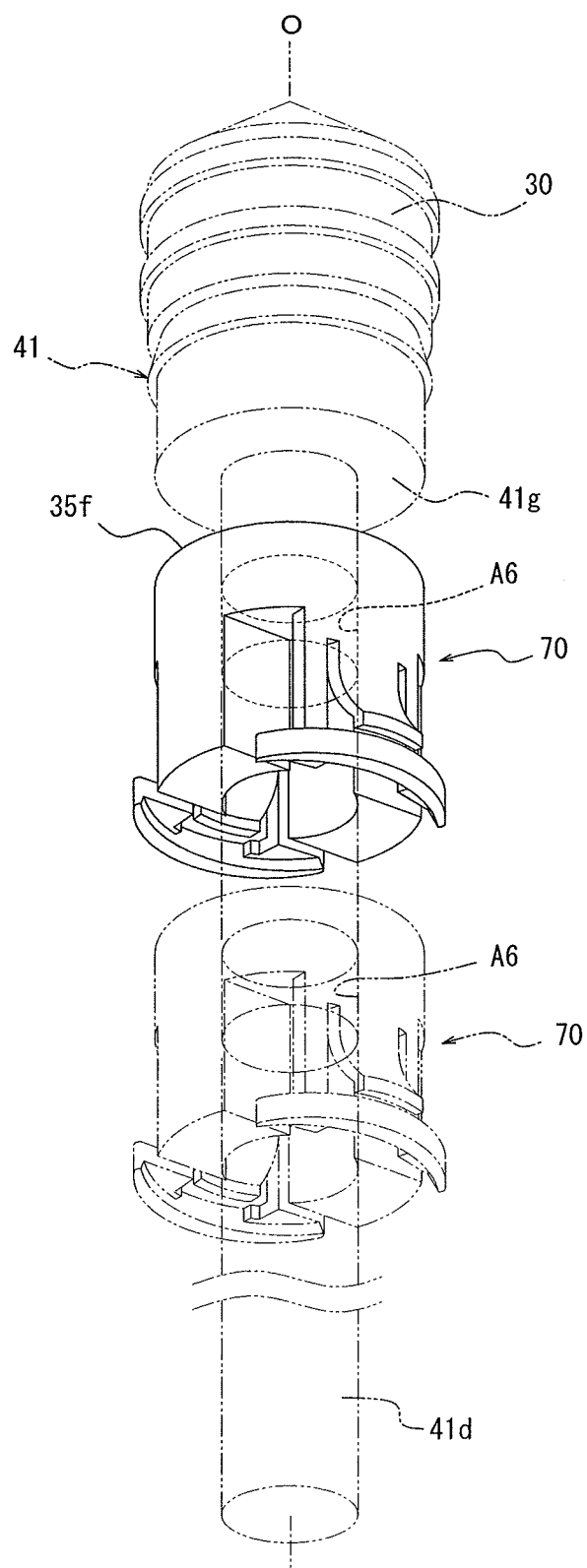
FIG. 19 is a perspective view schematically illustrating the step of assembling the intermediate member of 17A to a piston holding member.
Figure 20:
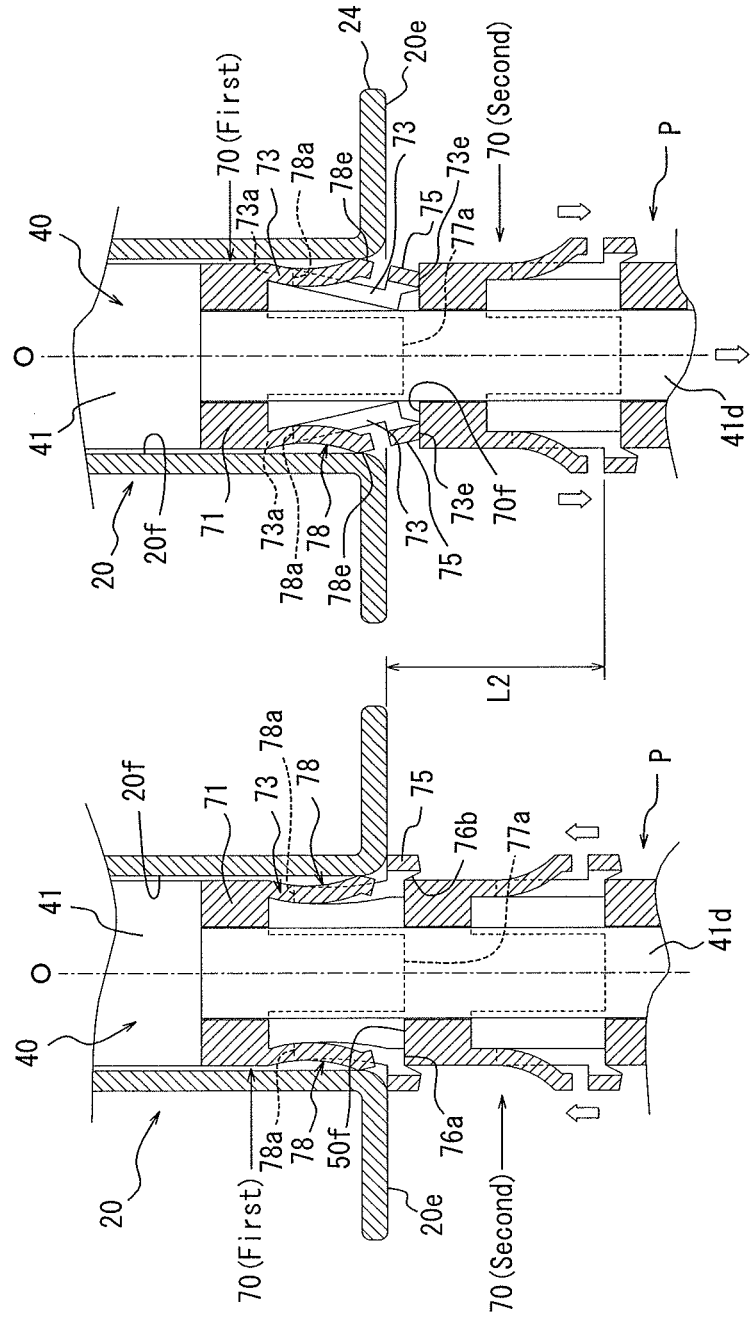
FIG. 20A is a partially enlarged sectional view of 17B.
FIG. 20B is a partially enlarged sectional view illustrating a state where the pushing of a plunger operation member is released for starting a second ejection in the nasal spray dispenser of FIG. 17A.
Figure 21:
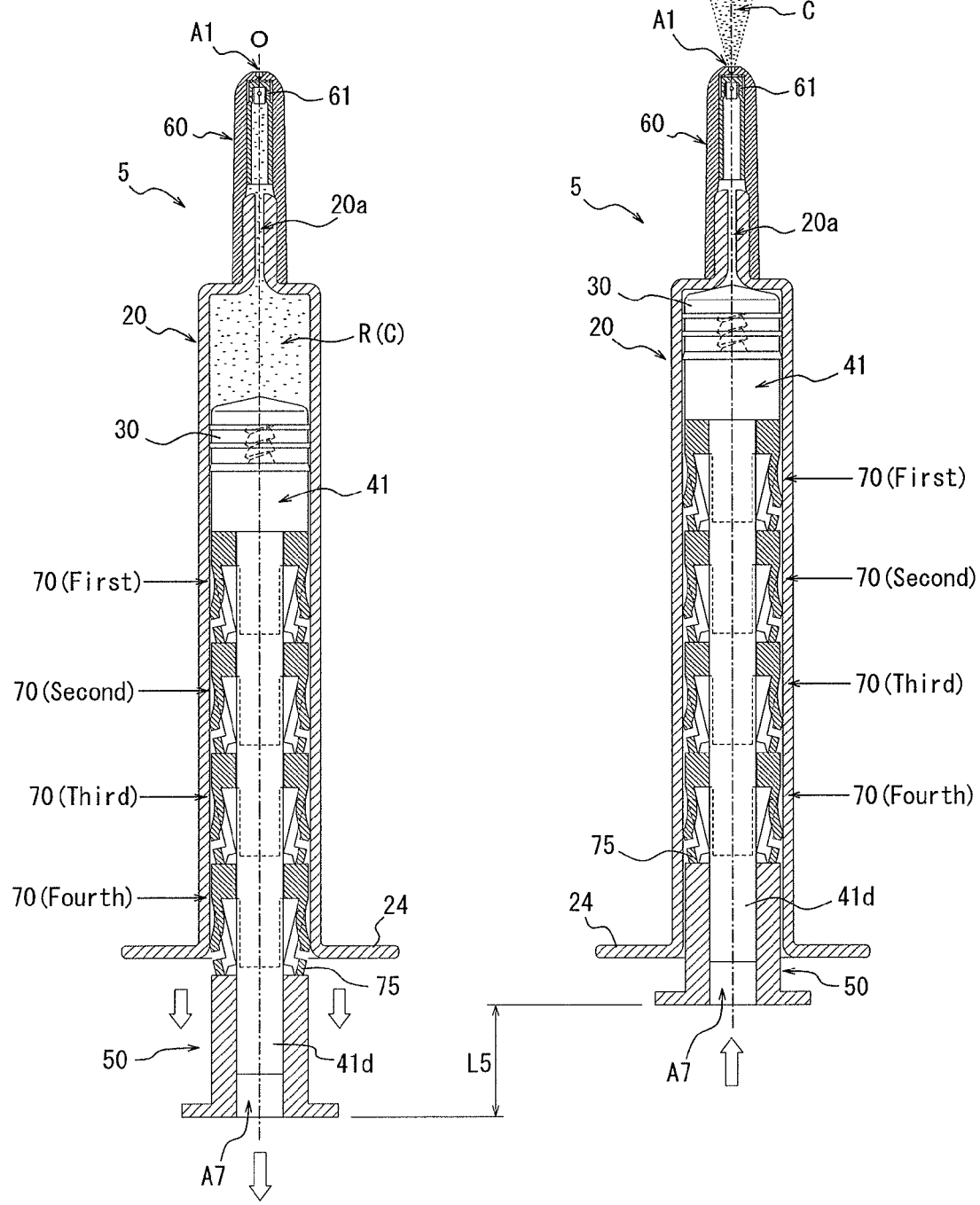
FIG. 21A is a partial side view illustrating a state where the pushing of the plunger operation member is released for starting a fifth ejection in the nasal spray dispenser of FIG. 17A.
FIG. 21B is a partial side view illustrating a state where the fifth ejection is completed.

Reference numeral 70 refers to an intermediate member constituting the plunger P. As illustrated in FIG. 18, the intermediate member 70 includes a cylindrical main body 71. The main body 71 includes, inside thereof, a through hole A6. As illustrated in FIG. 19, the through hole A6 lets the shaft portion 41d slidably penetrate therethrough. In the present embodiment, as illustrated in 17A, four intermediate members 70 are assembled through the shaft portion 41d.

As illustrated in FIG. 18, the intermediate members 70 are each provided with two arms 73 in an integrated manner. The arms 73 are positioned in a manner such that the arms 73 oppose to each other across the through hole A6. Each arm 73 has substantially the same structure as the arm 43 according to Embodiment 4. That is to say, each arm 73 may be deformed inward in the radial direction from a fixed end 73a thereof, when loaded with external force. The arm 73 may also be restored to the initial position (e.g. the position illustrated in FIG. 17A) when the load is released.

The arms 73 are also each provided with an elastic tongue piece 78. The elastic tongue piece 78 has substantially the same structure as the elastic tongue piece 48 according to Embodiment 4. That is to say, the elastic tongue piece 78 is arranged in the opening A5 formed in the arm 73. As illustrated in FIG. 18, the elastic tongue piece 78 has a fixed end 78a formed in an integrated manner from, among edge portions constituting the opening A5, an opening edge portion 73b that is on the side of the fixed end 73a of the arm 73. As illustrated in FIG. 18, the fixed end 78a of the elastic tongue piece 78 constitutes the same surface as the outer surface of the arm 73.

Similarly to the elastic tongue piece 48, the elastic tongue piece 78 is curved outward as the elastic tongue piece 78 advances toward the free end 73e of the arm 73, and an end 78e of the elastic tongue piece 78 is oriented outward in the radial direction. Furthermore, as illustrated in FIG. 17A, the two slide projections 44 opposing to each other about the axis line O have an interval between outermost diameters thereof in the radial direction that is greater than the inner diameter of the syringe 20 (which is the same as the diameter of the opening A2 provided in the rear end of the syringe 20 in the present embodiment). With the above structure, similarly to the elastic tongue piece 48, when the elastic tongue piece 78 comes into contact with the opening A2 provided in the rear end of the syringe 20, a portion of the elastic tongue piece 78 that is on the side of the end 78e serving as the free end undergoes flexure deformation starting from the fixed end 78a. As a result, the elastic tongue piece 78 enters the syringe 20. In the present embodiment, since the elastic tongue piece 78 is curved outward, the elastic tongue piece 78 may easily enter the syringe 20 though the opening A2 provided in the rear end of the syringe 20. Furthermore, with the end 78e, the elastic tongue piece 78 is allowed to slide on the inner circumferential surface 20f of the syringe 20.

The arm 73 is also provided in an integrated manner with a protrusion 75 that is similar to the protrusion 45 according to Embodiment 4. In the present embodiment, the protrusion 75 is formed at the free end 73e of the arm 73 in an integrated manner. Accordingly, in the present embodiment, a rear end surface of the protrusion 75 constitutes the free end 73e of the arm 73. In the present embodiment, the free end 73e of the arm 73 is configured by a taper inclined outward (i.e. inclined inward as the free end 73e advances rearward) at an angle θ with respect to the horizontal line perpendicular to the axis line O. Value of θ may be appropriately changed depending on the size of the nasal spray dispenser or the like. However, according to the present invention, the free end 73e of the arm 73 may also be configured by forming the rear end surface of the protrusion 75 to be a flat surface parallel with the horizontal line when the arm 73 is in the initial state.

Furthermore, in the present embodiment, as illustrated in FIG. 17A, the two protrusions 75 opposing to each other about the axis line O have an interval between outermost diameters thereof in the radial direction that is greater than the inner diameter of the syringe 20 (which is the same as the diameter of the opening A2 provided in the rear end of the syringe 20 in the present embodiment). Moreover, in the present embodiment, as illustrated in FIG. 18, the elastic tongue piece 78 is formed in a manner such that the end 78e (the portion of the elastic tongue piece 78 that is on the side of the free end) is positioned closest to the protrusion 75. Moreover, in the present embodiment, the protrusion 75 is provided with a step 76 that is substantially the same as the step 46 according to Embodiment 4. That is to say, similarly to the step 46 according to Embodiment 4, the step 76 includes a flat step bottom surface 76a and a step side surface 76b connected to the bottom surface 76a.

Furthermore, as illustrated in FIG. 18, the main body 71 of the intermediate member 70 is provided in an integrated manner with two support portions 77 that are substantially the same as the support portions 47 according to Embodiment 4. The support portions 77 are positioned in a manner such that the support portions 77 oppose to each other across the through hole A6. That is to say, a support portion end surface 77a of each support portion 77 constitutes a flat surface whose length measured from the main body 71 corresponds to the step bottom surface 76a provided in the arm 73.

When a first intermediate member 70 is inserted to the shaft portion 41d of the piston holding member 40, as illustrated in FIG. 17A, an end surface 70f of the first intermediate member 70 that is on a side of the main body contacts a rear end surface 41g of the main body 41 of the piston holding member 40. With the above structure, the first intermediate member 70 is positioned relative to the main body 41 in the direction of the axis line O. Subsequently, when a second intermediate member 70 is inserted in the shaft portion 41d, the end surface 70f of the second intermediate member 70 that is on the side of the main body contacts the step bottom surface 76a formed in the arm 73 of the first intermediate member 70 and also contacts the support portion end surface 77a of the first intermediate member 70. With the above structure, the second intermediate member 70 is positioned relative to the main body 41 in the direction of the axis line O by means of the first intermediate member 70. With the assembly similar to the above, a third and a fourth intermediate member 70 is positioned relative to the main body 41 of the piston holding member 40 in the direction of the axis line O.

On the other hand, inside the plunger operation member 50, a through hole A7 is formed. As illustrated in FIG. 17A, the through hole A7 lets the shaft portion 41d slidably penetrate therethrough. Furthermore, similarly to the end surface 70f of the intermediate member 70 that is on the side of the main body, an end surface 50f of the plunger operation member 50 that is on the side of the main body contacts the step bottom surface 76a formed in the arm 73 of the fourth intermediate member 70 and also contacts the support portion end surface 77a of the fourth intermediate member 70. With the above structure, the plunger operation member 50 is positioned relative to the main body 41 of the piston holding member 40 in the direction of the axis line O by means of the four intermediate members 70. In the present embodiment, the plunger operation member 50 is press-fitted in a slidable manner with respect to the shaft portion 41d of the piston holding member 40.

Figure 17B:
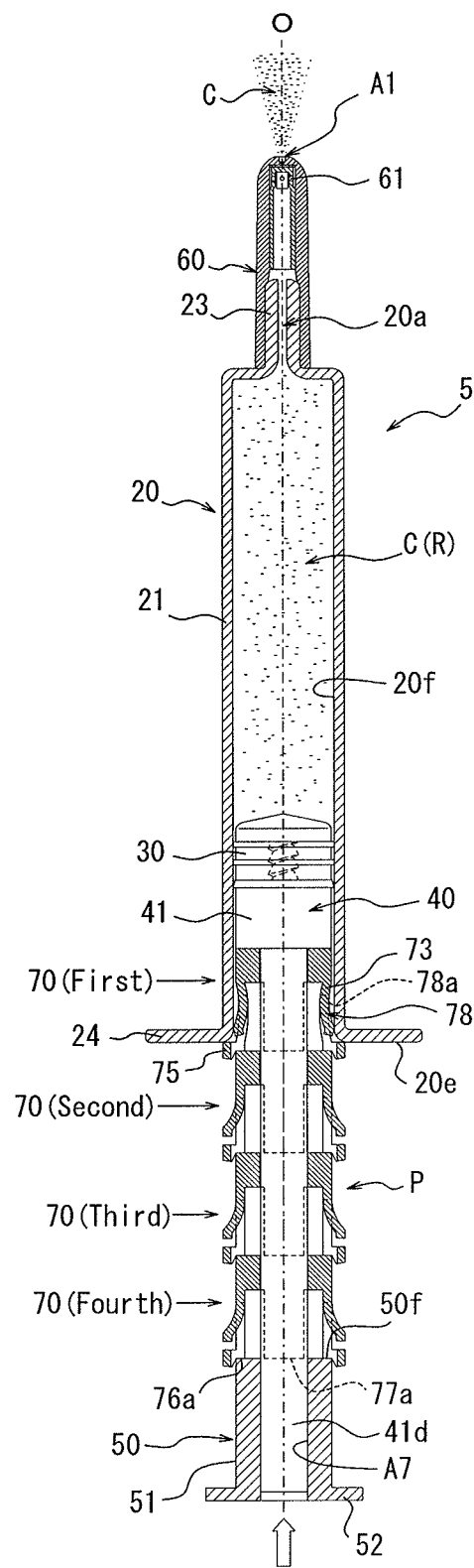
FIG. 17B is a side view taken along one section illustrating a state where a first ejection is completed in the nasal spray dispenser of FIG. 17A.

Here, a description is given of a method of use of the present embodiment. Basic operation of the present embodiment is substantially the same as that in Embodiment 4. From the state illustrated in FIG. 17A, the user pushes the plunger operation member 50. Then, as illustrated in FIG. 17B, the four intermediate members 70 are sandwiched between the piston holding member 40 that is subject to fluid pressure applied by the piston 30 and the plunger operation member 50 that is subject to pressing force applied by the user. As a result, the piston holding member 40, the intermediate members 70, and the plunger operation member 50 are pushed integrally into the syringe 20 as the plunger P. At this time, as illustrated in FIG. 17B, the elastic tongue piece 78 provided in the arm 73 may easily enter the syringe 20 though the opening A2 provided in the rear end of the syringe 20.

Furthermore, when the elastic tongue piece 78 of the first intermediate member 70 enters the syringe 20, as illustrated in FIG. 20A, the elastic tongue piece 78 of the first intermediate member 70 undergoes flexure deformation starting from the fixed end 78a connected to the arm 73. Accordingly, the end 78e of the elastic tongue piece 78 is allowed to slide on the inner circumferential surface 20f of the syringe 20. Thus, as illustrated in FIG. 20A, because the plunger P is pushed without being obstructed by the elastic tongue piece 78, until the protrusion 75, following the elastic tongue piece 78, of the arm 43 comes into contact with the rear end 20e of the syringe 20, a metered quantity of the content C is ejected. (Refer to a stroke L1 illustrated in FIG. 17A.)

As illustrated in FIG. 20A, when the protrusion 75 comes into contact with the rear end 20e of the syringe 20, the plunger operation member 50 may not be pushed in anymore. Then, the first ejection is completed while the content C still remains in the room R. The volume of the syringe 20 at this time may be appropriately determined in accordance with intended use. For example, in the present embodiment, in accordance with a total number of the intermediate members 70 and the plunger operation member 50, a dose of each ejection is set to be one fifth the entire volume prior to the start of the ejection.

Subsequently, when the pushing of the plunger operation member 50 is released, the free end 73e of the arm 73 provided in the first intermediate member 70 is released from restraint. In detail, due to the step side surface 76b in the form of an inclined surface, the second intermediate member 70 is pushed back, and correspondingly, the third and the fourth intermediate member 70 and the plunger operation member 50 slide to be displaced with respect to the shaft portion 41d. As a result, as illustrated in the states from FIG. 20A to FIG. 20B, the arm 73 provided in the first intermediate member 70 undergoes inward deformation starting from the fixed end 78a of the elastic tongue piece 78. Accordingly, the locking state of the protrusion 75 and the rear end 20e of the syringe 20 is released as illustrated in FIG. 20B.

In the present embodiment, when the second intermediate member 70 is pushed back by the first intermediate member 70, as illustrated in FIG. 20B, the end surface 70f of the second intermediate member 70 that is on the side of the main body is allowed to contact the free end 73e of the arm 73 provided in the first intermediate member 70. With the above structure, after the pushing of the plunger operation member 50 is released, by pushing in the plunger operation member 50 again, as illustrated in FIGS. 20A and 20B, the second ejection is achieved for the amount corresponding to a stroke L2.

Furthermore, in the present embodiment, the four intermediate members 70 are assembled with the plunger operation member 50 through the shaft portion 41d of the piston holding member 40 in a manner such that the intermediate members 70 are capable of sliding sequentially. With the above structure, subsequently, a metered quantity is sequentially ejected simply by repeating the similar operation. That is to say, as illustrated in FIG. 21A, after the fourth time pushing is released, by pushing in the plunger operation member 50 again, as illustrated in FIG. 21B, the fifth ejection is achieved for the amount corresponding to a stroke L5. Thus, by repeating the above operation for each intermediate member 70, ejection is achieved a plurality of times corresponding to the total number of the intermediate members 70 and the plunger operation member 50.

Although in the present embodiment the strokes L1-L5 are assigned with the same amount of stroke volume, the stroke volume may be appropriately changed for example by modifying the intermediate members 70.

Figure 22:
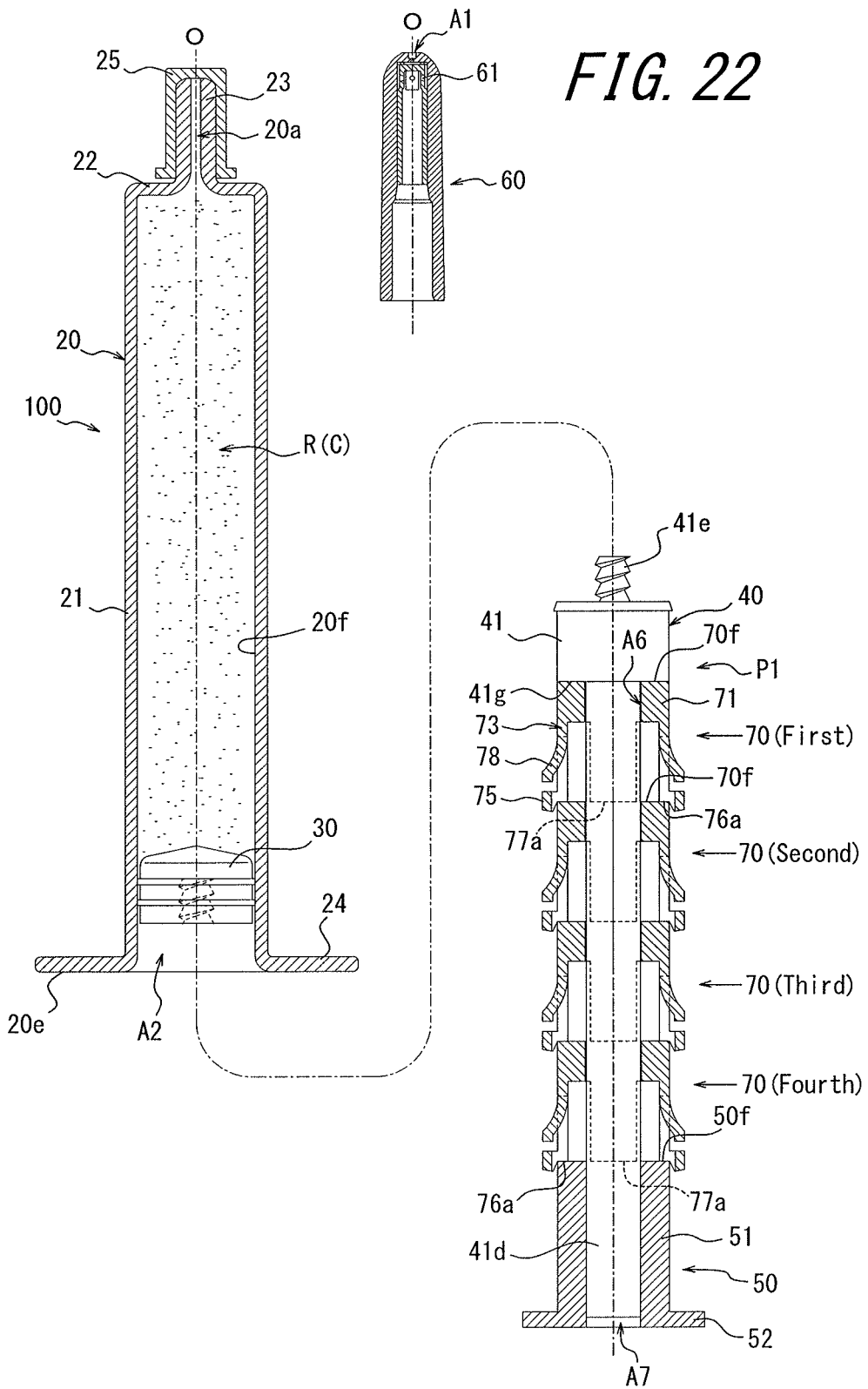
FIG. 22 is a partial side view illustrating a state where the cartridge-type nasal spray dispenser of FIG. 17A is disassembled.

In the present embodiment, as illustrated in FIG. 22, the syringe 20 may function as a cartridge 100 that is filled with the content C. The cartridge 100 is configured by detachably fitting a cap 25 to the front end portion 23 of the syringe 20. The cap 25 seals the through hole 20a formed inside the front end portion 23. In the present embodiment, the piston 30 is arranged in the syringe 20 in advance through the opening A2. With the above structure, the content C filled in the syringe 20 is sealed and held by the cap 25 and the piston 30. In the present embodiment, the main body 41 of the piston holding member 40 includes a holding portion 41e that holds the piston 30. The holding portion 41e is provided, at a front end thereof, with a screw portion. With the above structure, the piston 30 is detachably fitted to the main body 41.

In assembly of a nasal spray dispenser 5, a plunger main body P1 is screwed into the cartridge 100 that is illustrated in FIG. 22. As illustrated in FIG. 22, the plunger main body P1 includes the piston holding member 40, the intermediate members 70, and the plunger operation member 50. With the above structure, the plunger main body P1 is fixed to the piston 30 arranged in the cartridge 100. Subsequently, after the cap 25 is removed from the syringe 20, the nozzle 60 is fitted to the front end portion 23 of the syringe. By doing so, as illustrated in FIG. 17A, the assembly of the nasal spray dispenser 5 is completed.

According to the present embodiment, since the locking of the arm 73 with respect to the syringe 20 is released by the restoring force of the elastic tongue piece 78 provided in the arm 73, wherever the elastic tongue piece 78 is positioned with respect to the arm 73, by releasing pressure to the free end 73e of the arm 43, the locking of the arm 73 is released. Thus, as in the present embodiment, the elastic tongue piece 78 may be arranged in a position closest to the protrusion 75. In the above circumstance, the elastic tongue piece 78 is not deformed until immediately before the arm 73 is locked, and even when the pushing of the plunger P is loosened or released in the middle of ejection of the content C, the arm 73 remains capable of being locked with respect to the syringe 20. Accordingly, by arranging the elastic tongue piece 78 in the position closest to the protrusion 75 as in the present embodiment, even when the pushing of the plunger P is stopped in the middle of the ejection, the quantity is precisely metered for the ejection without the metered content C being affected.

Figure 23:
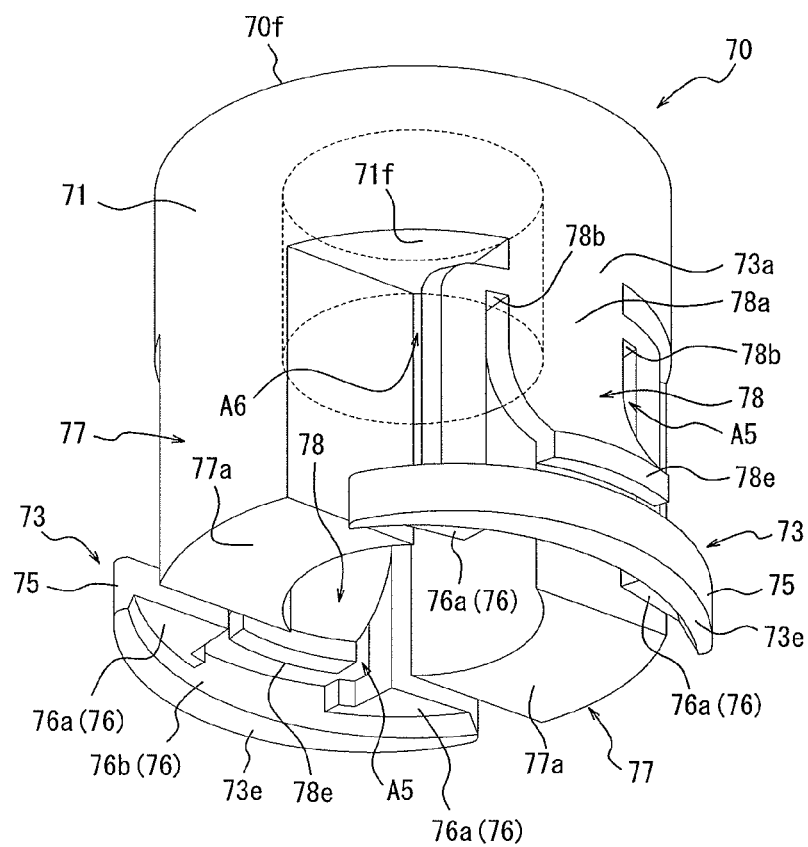
FIG. 23 is a perspective view illustrating an intermediate member from a side on which pressure is received, according to another embodiment of the present invention.

FIG. 23 is a perspective view illustrating an intermediate member 70 as viewed from the rear end, according to another embodiment. In the present embodiment, the fixed end 73a of the arm 73 is configured as a narrow-width portion standing from a rear end surface 71f of the main body 71 in an integrated manner. In the present embodiment, the fixed end 73a of the arm 73 has a width that is substantially the same as a width of the elastic tongue piece 78. That is to say, the arm 73 is configured to have a greater width in a portion of the arm 73 in which the elastic tongue piece 78 is arranged than in the fixed end 73a. In the above circumstance, the arm 73 may undergo deformation starting from the fixed end 73a relatively easily. In FIG. 23, configurations substantially the same as those of other embodiments are denoted by the same reference numerals, and a description thereof is omitted.

The present invention is not limited to the structures described above, and various modifications may be made to the above description. For example, the nasal spray dispenser 5 does not need to be a cartridge-type dispenser and may be configured as a disposable syringe-type dispenser.

FIGS. 24-27 illustrate a nasal spray dispenser according to Embodiment 6 of the present invention. In the following, configurations substantially the same as those of other embodiments are denoted by the same reference numerals.

Figure 24:
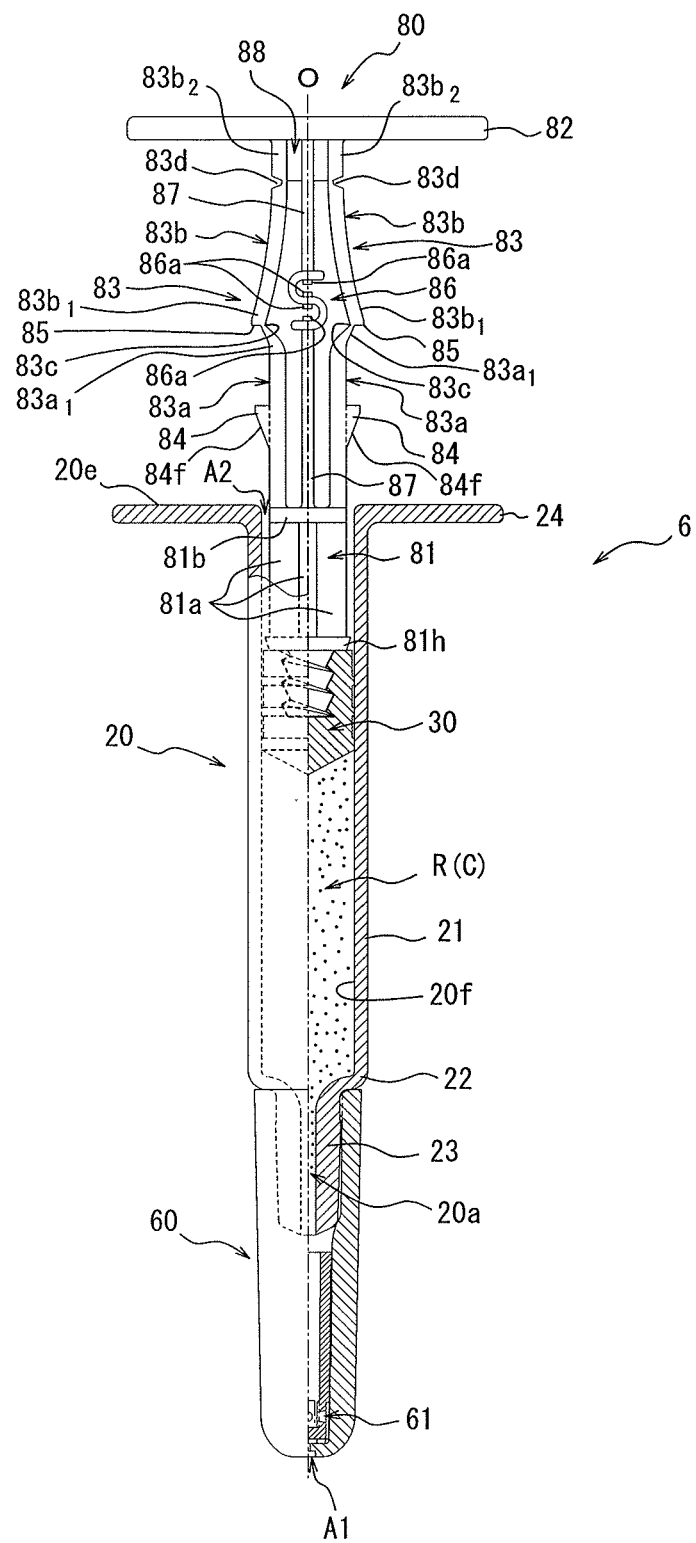
FIG. 24 is a side view taken along a partial section illustrating a nasal spray dispenser that is in an initial state prior to an operation thereof, according to Embodiment 6 of the present invention.

In FIG. 24, reference numeral 6 refers to a synthetic resin nasal spray dispenser according to Embodiment 6 of the present invention. Reference numeral 80 refers to a plunger. The plunger 80 includes a main body 81 configured to hold the piston 30. The main body 81 includes a fixing portion 81h configured to fix the piston 30, four plate portions 81a, and a disk portion 81b, which are formed integrally. Reference numeral 82 refers to a plunger operation portion for the user to push in the plunger 80. In the present embodiment, the plunger operation portion 82 has a disk shape having the same diameter as that of the finger rest 24 of the syringe 20.

Reference numeral 86 refers to an elastic portion arranged between the main body 81 and the plunger operation portion 82. Between the main body 81 and the plunger operation portion 82, a pair of support portions 87 is formed along the axis direction, and elastic portions 86 are disposed between the support portions 87. That is to say, the elastic portions 86 are coupled via the support portion 87 in an integrated manner, between the main body 81 and the plunger operation portion 82. In the present embodiment, each elastic portion 86 has an S-shape. With the above structure, the elastic portion 86 may undergo deformation and restoration depending on load conveyed through the support portion 87. Furthermore, the elastic portions 86 are provided, on contact surfaces thereof facing each other, with contact portions 86a. The contact portions 86a control the magnitude of deformation of the elastic portion 86 by contacting each other.

Reference numeral 83 refers to arm portions that couple the main body 81 and the plunger operation portion 82 in an integrated manner. The arm portions 83 are positioned in a manner such that the arm portions 83 oppose to each other across the elastic portions 86. Each arm portion 83 includes a front end side arm 83a and a rear end side arm 83b. The front end side arm 83a is deformable and restorable and extends rearward from the main body 81. The rear end side arm 83b extends forward from the plunger operation portion 82. The front end side arm 83a and the rear end side arm 83b are coupled in an integrated manner. A coupling portion of the front end side arm 83a and the rear end side arm 83b is provided with a bent portion 83c. The bent portion 83c is formed in a small thickness. The bent portion 83c may push the entire arm portion 83 open outward.

Each front end side arm 83a is also provided with a slide projection 84. As illustrated in FIG. 24, the slide projection 84 is positioned in a manner such that the slide projection 84 faces the inner circumferential surface 20f of the syringe 20. Furthermore, as illustrated in FIG. 24, the two slide projections 44 opposing to each other about the axis line O have an interval between outermost diameters thereof in the radial direction that is greater than the inner diameter of the syringe 20 (which is the same as the diameter of the opening A2 provided in the rear end of the syringe in the present embodiment). When the slide projections 84 come into contact with the opening A2 provided in the rear end of the syringe 20, the arms 83 undergo flexure deformation starting from the slide projections 84. As a result, the slide projections 84 enter the syringe 20 and slide on the inner circumferential surface 20f of the syringe 20.

In the present embodiment, each slide projection 84 includes an inclined surface 84f that tapers toward the main body 81. With the above structure, the slide protrusion 84 may easily enter the syringe 20 though the opening A2 provided in the rear end of the syringe 20.

In the present embodiment, the front end side arm 83a is formed in a substantially flat plate shape extending along the axis line O. The front end side arm 83a is curved outward as a coupling base portion $83a_1$ of the front end side arm 83a that is on a side of the bent portion 83c advances toward the bent portion 83c. The rear end side arm 83b is curved outward as a coupling base portion $83b_1$ of the rear end side arm 83b that is on the side of the bent portion 83c advances toward the bent portion 83c.

The bent portion 83c is provided with the protrusion 85. As illustrated in FIG. 24, the protrusion 85 is positioned in a manner such that the protrusion 85 faces the inner circumferential surface 20f of the syringe 20. Furthermore, the two protrusions 85 have an interval between outermost diameters thereof in the radial direction that is greater than the inner diameter of the syringe 20 (which is the same as the diameter of the opening A2 provided in the rear end of the syringe in the present embodiment). With the above structure, when in contact with the rear end 20e of the syringe 20, the protrusion 85 is locked by the rear end 20e. In the present embodiment, the protrusion 85 includes a contact surface with the rear end 20e of the syringe 20. As illustrated in FIG. 24, the contact surface is a flat surface formed further outward of the bent portion 83c.

In the present embodiment, the rear end side arm 83b of the rear end side arm 83b that is on the side of the plunger operation portion 82 is formed in an integrated manner with the plunger operation portion 82 and the support portions 87 via a coupling portion 88. Furthermore, the coupling base portion $83b_2$ of the rear end side arm 83b is provided with a groove portion 83d. The groove portion 83d makes the rear end side arm 83b easy to open outward. In the present embodiment, the groove portion 83d is a portion with a small thickness that is formed in an outer circumferential surface of the coupling base portion $83b_2$.

Here, a description is given of a method of use of the present embodiment. Basic operation of the present embodiment is substantially the same as those in other embodiments. From the state illustrated in FIG. 24, the user pushes the plunger operation member 82. Then, in the arm portion 83, the slide protrusion 84 provided in the front end side arm 83a enters the syringe 20 though the opening A2 provided in the rear end of the syringe 20 and slides on the inner circumferential surface 20f of the syringe 20. At this time, the bent portion 83c of the arm portion 83 is hardly deformed due to elastic force of the elastic portion 86 urged via the support portion 87. Accordingly, even when the plunger 80 is pushed in by means of the plunger operation portion 82, bending of the entire arm portion 83 is prevented.

Figure 25:
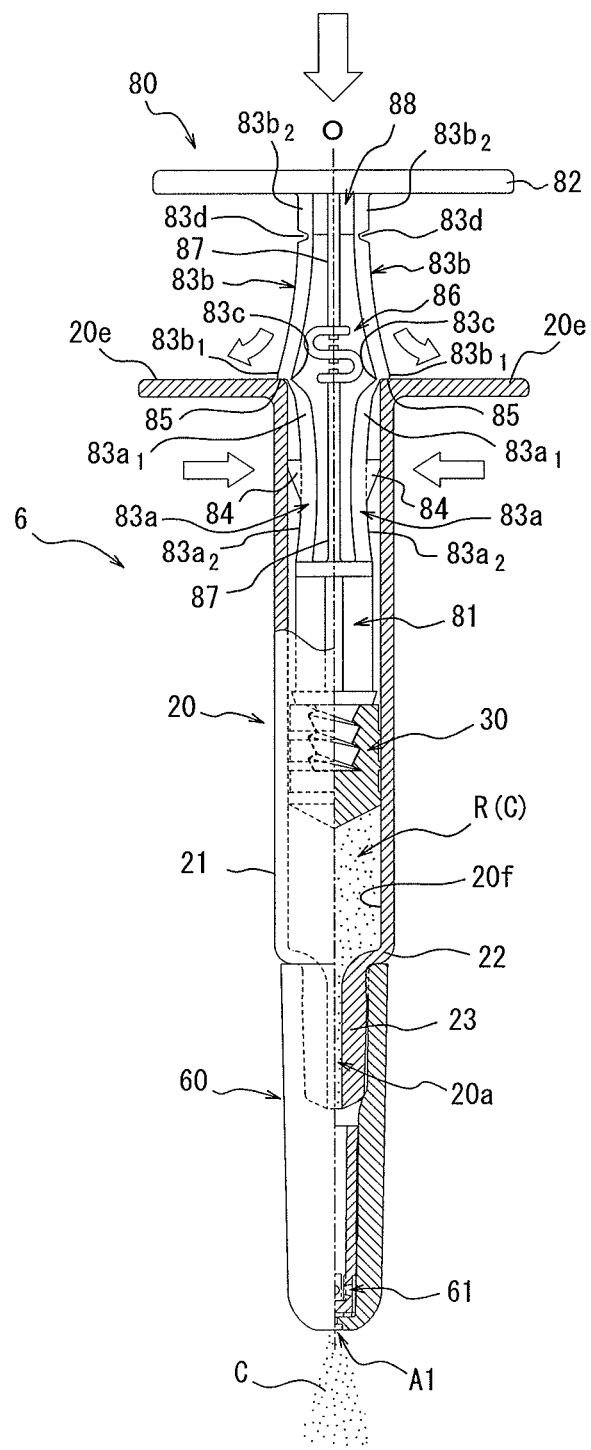
FIG. 25 is a side view taken along one section illustrating a state where a first ejection is completed in the nasal spray dispenser of FIG. 24.

By the arm portion 83 thus sliding on the inner circumferential surface 20f of the syringe 20 without undergoing bending starting from the bent portion 83c, as illustrated in FIG. 25, the front end side arm 83a undergoes inward flexure deformation starting from the slide projection 84. As a result, the plunger 80 may be pushed into the syringe 20 without being obstructed by the slide projection 84. The pushing may be continued until the protrusion 85 provided in the arm portion 83 comes into contact with the rear end 20e of the syringe 20 to be locked as illustrated in FIG. 25. Thus, until the protrusion 85 is locked by the rear end 20e of the syringe 20, a metered quantity of the content C is ejected through the ejection orifice A1.

When the protrusion 85 provided in the arm portion 83 is locked by the rear end 20e of the syringe 20, the plunger P may not be pushed in anymore. Then, as illustrated in FIG. 25, the first ejection is completed while the content C still remains in the room R. The volume of first ejection may be appropriately determined as in other embodiments and may be half the total volume of ejection, for example.

Figure 26:
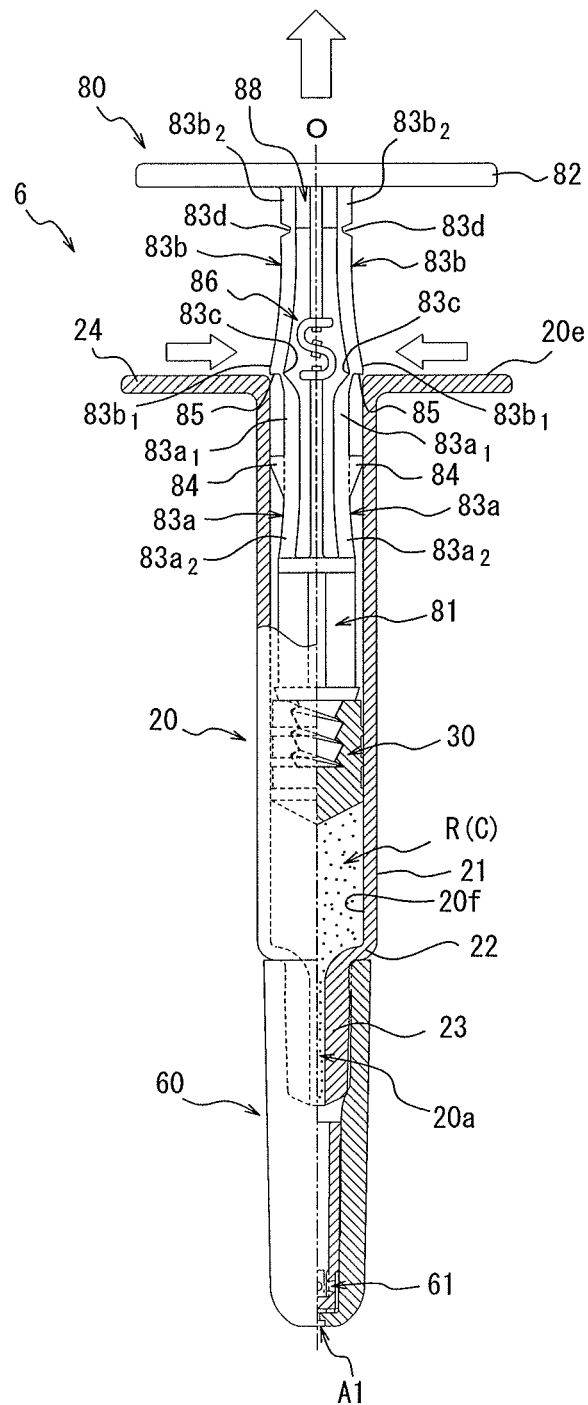
FIG. 26 is a side view taken along a partial section illustrating a state where the pushing of a plunger is released for starting a second ejection in the nasal spray dispenser of FIG. 24.

Subsequently, when the pushing of the plunger operation portion 82 is released, restoring force of the elastic portion 86 restores the arm portion 83 to the initial state in which the arm 83 is not loaded with pressing force applied by the plunger operation portion 82. At this time, a portion $83a_2$ of the front end side arm 83a that is on the side of the main body is still subject to inward deformation starting from the slide projection 84. As a result, the coupling base portion $83a_1$ of the front end side arm 83a is restored diagonally inward in a manner such that the coupling base portion $83a_1$ is aligned with the portion $83a_2$ of the front end side arm 83a that is on the side of the main body and that has undergone inward deformation starting from the slide projection 84. Correspondingly, the protrusion 85, which connects to the bent portion 83c, is displaced diagonally inward in conjunction with the bent portion 83c in accordance with the coupling base portion $83a_1$, and as illustrated in FIG. 26, the locking state of the protrusion 85 is released.

Figure 27:
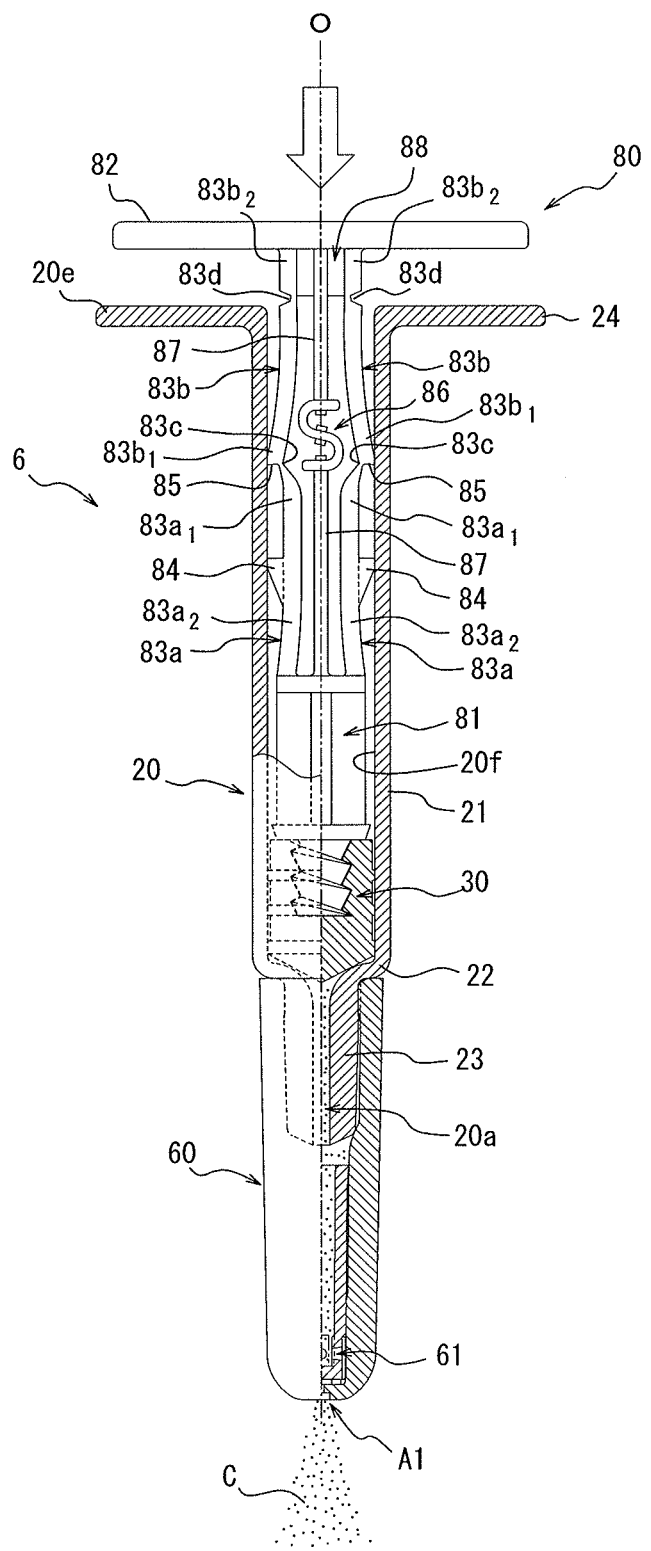
FIG. 27 is a side view taken along a partial section illustrating a state where the second ejection is completed in the nasal spray dispenser of FIG. 24.

Accordingly, after the pushing of the plunger operation member 82 is released and the arm portion 83 is restored to the initial state, by inserting the plunger operation portion 82 again, as illustrated in FIG. 27, the content C remaining in the room R is ejected through the ejection orifice A1 as the second ejection.

FIGS. 28-33 illustrate a nasal spray dispenser according to Embodiment 7 of the present invention. In the following, configurations substantially the same as those of other embodiments are denoted by the same reference numerals.

Figure 28A:
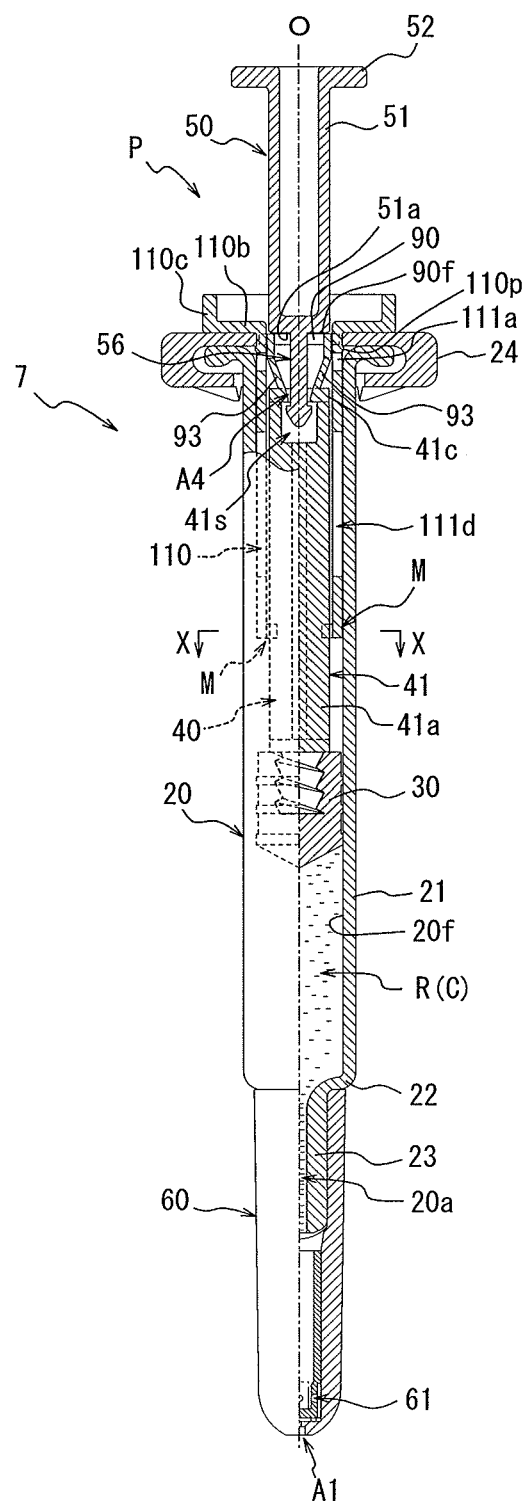
FIG. 28A is a side view taken along a partial section illustrating a nasal spray dispenser that is in an initial state prior to an operation thereof, according to Embodiment 7 of the present invention.
Figure 29:
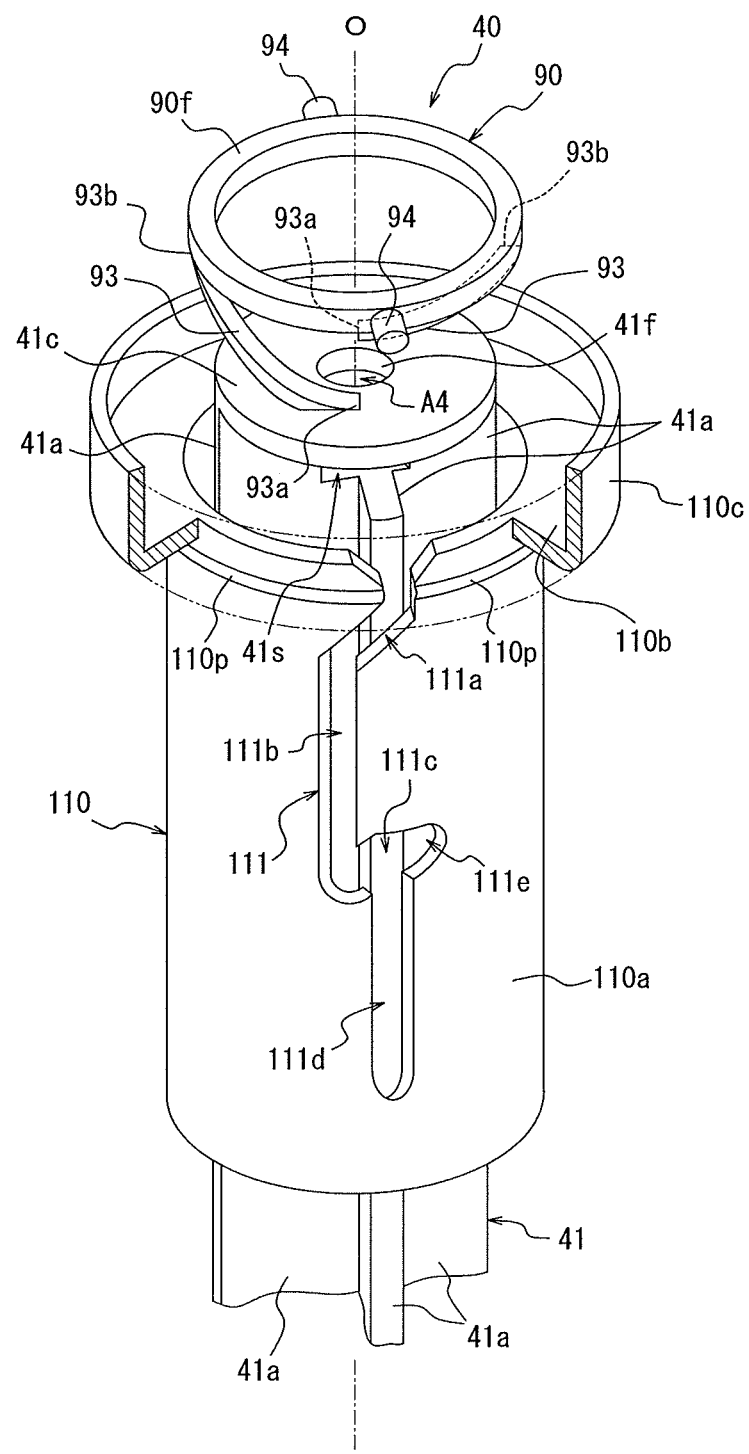
FIG. 29 is a perspective view schematically illustrating a piston holding member of FIG. 28A in a state where the piston holding member is accommodated in a sleeve member.
Figure 30:
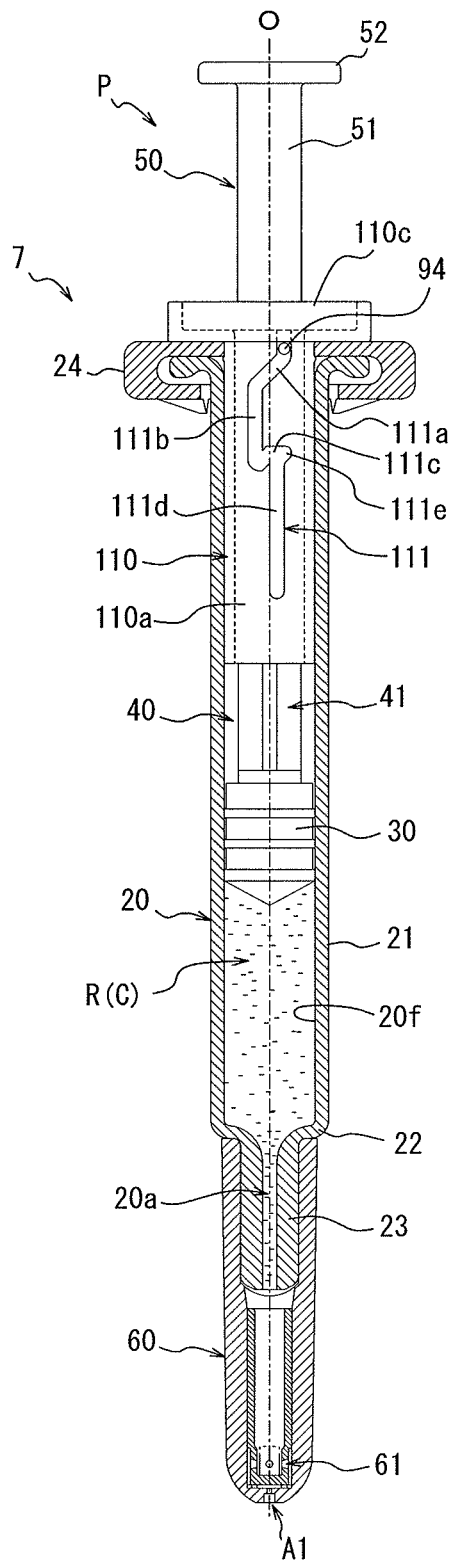
FIG. 30 is another side view taken along a partial section illustrating an initial state prior to an operation of FIG. 28A.

In FIG. 28A, reference numeral 7 refers to a synthetic resin nasal spray dispenser according to Embodiment 7 of the present invention. The plunger P includes the piston holding member 40 and the plunger operation member 50. The piston holding member 40 includes the main body 41. As illustrated in FIG. 29, the ring portion 41c of the main body 41 is provided with a pressed portion 90, with a gap provided between the ring portion 41c and the pressed portion 90 in the direction of the axis line O. The pressed portion 90 includes a pressed surface 90f configured to receive the plunger operation member 50 and is provided in the ring portion 41c in an integrated manner via a plurality of torsion spring portions 93. The torsion spring portions 93 create torsion deformation around the axis line O in response to pressing force received from the pressed portion 90. The torsion deformation also creates restoring force in the torsion spring portions 93 when the pressing force applied by the pressed portion 90 is released. With the above structure, when the pressing force applied by the pressed portion 90 is released, the pressed portion 90 is returned to the initial position (the position illustrated in FIG. 28A in the present embodiment) before the pressed portion 90 is pressed.

In the present embodiment, the torsion spring portions 93 each have a semi-helical spring shape standing from the ring portion 41c around the axis line O. The torsion spring portions 93 are positioned in a manner such that the torsion spring portions 93 oppose to each other across the through hole A4. For example, in the present embodiment, the torsion spring portion 93 includes a fixed end 93a with respect to the ring portion 41c and a fixed end 93b with respect to the pressed portion 90. A line connecting the fixed end 93a and the fixed end 93b forms an angle of 45 degrees with respect to the axis line O.

In the present embodiment, as illustrated in FIG. 29, the pressed portion 90 is in the form of a hollow ring. The pressed surface 90f of the pressed portion 90 is a flat surface. The pressed portion 90 has a side surface provided with lateral protrusions 94 in an integrated manner. The protrusions 94 are arranged in a manner such that the protrusions 94 oppose to each other across the through hole A4. Furthermore, in the present embodiment, the protrusions 94 are positioned to be aligned with the fixed end 93a of the torsion spring portion 93 on an axis line in the radial direction.

Reference numeral 110 refers to a sleeve member including a trunk portion 110a arranged inside the syringe 20. The sleeve member 110 includes, at one end of the trunk portion 110a, a flat annular overhanging portion 110b in an integrated manner. The overhanging portion 110b extends around the axis line O. On an outer edge of the overhanging portion 110b, a circumferential wall 110c extending in a direction away from the trunk portion 110a is also provided in an integrated manner. Furthermore, the trunk portion 110a has an outer circumference that is provided with an annular convex portion 110p extending around the axis line O. The convex portion 110p is positioned at a distance from the overhanging portion 110b in the direction of axis line O. With the above structure, when the trunk portion 110a of the sleeve member 110 is inserted into the syringe 20, as illustrated in FIG. 28A, the sleeve member 110 is prevented from slipping off and held between the overhanging portion 110b and the convex portion 110p with respect to an inner edge of the finger rest 24 provided as a member separate from the syringe 20.

Figure 28B:
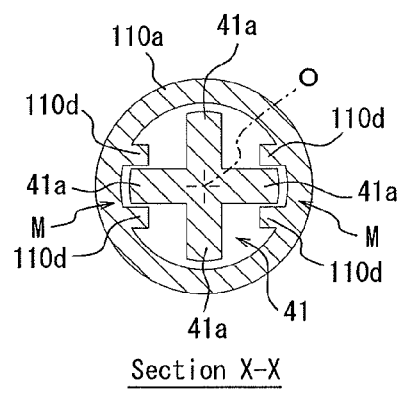
FIG. 28B is a sectional view taken along a line X-X illustrated in FIG. 28A.

Inside the sleeve member 110, the piston holding member 40 is slidably disposed along the axis line O. As illustrated in FIG. 28A, the piston holding member 40 and the sleeve member 110 are provided with a detent means M configured to prevent the piston holding member 40 from rotating about the axis line O. In the present embodiment, as illustrated in FIG. 28B, the detent means M includes the plate portions 41a constituting the main body 41 of the piston holding member 40 and two guiding projections 110d configured to guide the plate portions 41a in the direction of the axis line O. With the above structure, the piston holding member 40 is capable of sliding in the sleeve member 110 along the axis line O without rotating around the axis line O. Although in the present embodiment the detent means M is provided in two positions opposing to each other about the axis line O, it is only necessary to provide the detent means M in correspondence with at least one of the four plate portions 41a.

In addition, as illustrated in FIG. 29, the sleeve member 110 includes a crank 111 configured to guide the protrusions 94 provided in the pressed portion 90. In the present embodiment, the crank 111 is arranged in two positions opposing to each other about the axis line O. Furthermore, as illustrated in FIG. 29, the crank 111 is in the form of a slit extending through the trunk portion 110a. The protrusions 94 of the pressed portion 90 may be displaced along the cranks 111.

In the present embodiment, each crank 111 includes a torsion passage 111a. The torsion passage 111a advances along the axis line O and subsequently, is inclined with respect to the axis line O as it advances in a push-in direction, thereby allowing the piston holding member 40 to be pushed in and providing torsion to the torsion spring portion 93. However, the portion of the torsion passage 111a that advances along the axis line O may be omitted. The torsion passage ill a communicates with a first push-in passage 111b. The first push-in passage 111b extends along the axis line O, and therefore, allows the piston holding member 40 to be pushed in, while the torsion provided to the torsion spring portion 93 is maintained.

The first push-in passage 111b communicates with a return passage 111c. The return passage 111c is inclined toward the torsion passage 111a as the return passage 111c advances toward a pull-out direction (which is opposite to the push-in direction) with respect to the axis line O. With the above structure, the return passage 111c releases the pushing of the piston holding member 40 and releases the torsion provided to the torsion spring portion 93, so that the torsion spring portion 93 is restored.

The return passage 111c communicates with a second push-in passage 111d. The second push-in passage 111d extends from the return passage 111c along the axis line O, and therefore, allows the piston holding member 40 to be pushed in. In the present embodiment, the crank 111 includes a retreating portion 111e provided between the return passage 111c and the second push-in passage 111d. The retreating portion 111e is formed by extending the return passage 111c slightly more with respect to the second push-in passage 111d, and the retreating portion 111e may be releasably hooked by the protrusions 94 of the pressed portion 90.

Figure 31A:
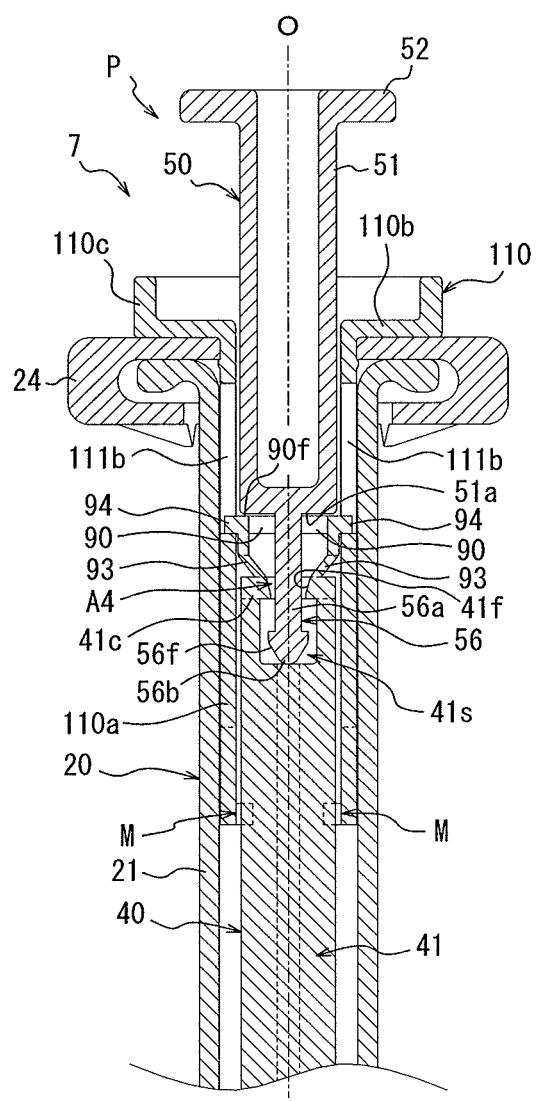
FIG. 31A is an enlarged sectional view illustrating a state where a first ejection is completed in the nasal spray dispenser of FIG. 28A as viewed from one side.

On the other hand, as illustrated in FIG. 31A, the plunger operation member 50 includes the main body 51 that is provided, at the rear end thereof, in an integrated manner with the plunger operation portion 52 for the user to push in the plunger P. The main body 51 has a cylindrical shape. As illustrated in FIG. 31A, the front end portion of the main body 51 forms the main body end surface 51a that presses the piston holding member 40. The main body end surface 51a is formed as a flat pressing surface.

Furthermore, as illustrated in FIG. 31A, the main body 51 is provided with the shaft 56 in an integrated manner. The shaft 56 includes the shaft body 56a having a diameter smaller than the diameter of the main body end surface 51a. The shaft body 56a extends forward from the main body end surface 51a along the axis line O. The shaft body 56a is provided, at the front end thereof, with the head 56b having a diameter greater than the diameter of the shaft body 56a, in an integrated manner. As illustrated in FIG. 31A, the head 56b includes the inclined surface 56f that tapers toward the front end of the head 56b. The shaft 56 is fitted to and held by the through hole A4 formed in the piston holding member 40. The through hole A4 has an inner diameter that is greater than the diameter of the shaft body 56a and smaller than the diameter of the head 56b. As illustrated in FIG. 31A, the through hole A4 lets the shaft body 56a penetrate therethrough and also holds the head 56b by preventing the head 56b from slipping off. The head 56b and the inner circumferential surface 41f of the ring portion 41c hold the piston holding member 40 to the plunger operation member 50 by preventing the piston holding member 40 from slipping off. In the present embodiment in particular, the inner circumferential surface 41f is configured by a tapered surface whose diameter increases rearward. With the above structure, the head 56b may be easily assembled to the end surface of the ring portion 41c that is on the side of the front end (i.e. the end surface of the ring portion 41c near the piston 30). The open space 41s, which is formed by cutting the plate portions 41a, defines play space in which the head 56b is displaceable forward and rearward along the axis line O. With the above structure, the piston holding member 40 and the plunger operation member 50 may be displaceably coupled to each other along the axis line O.

As illustrated in FIG. 28A, the piston 30 is provided in the front end portion of the main body 41 and accommodated in the syringe 20. The piston 30 is made of an elastic material such as rubber or the like and is slidably held on the inner circumferential surface 20f of the trunk portion 21 of the syringe.

Between the syringe 20 and the piston 30, the room R is formed. The room R is configured to be filled with the content C. The content C filled in the room R is pumped to the through hole 20a formed in the front end portion 23 of the syringe in response to pushing of the piston 30. Reference numeral 60 refers to the nozzle fitted to the front end portion 23 of the syringe. The nozzle 60 includes the built-in chip 61 and is capable of ejecting the content C, which has been pumped through the through hole 20a, through the ejection orifice A1.

Figure 31B:
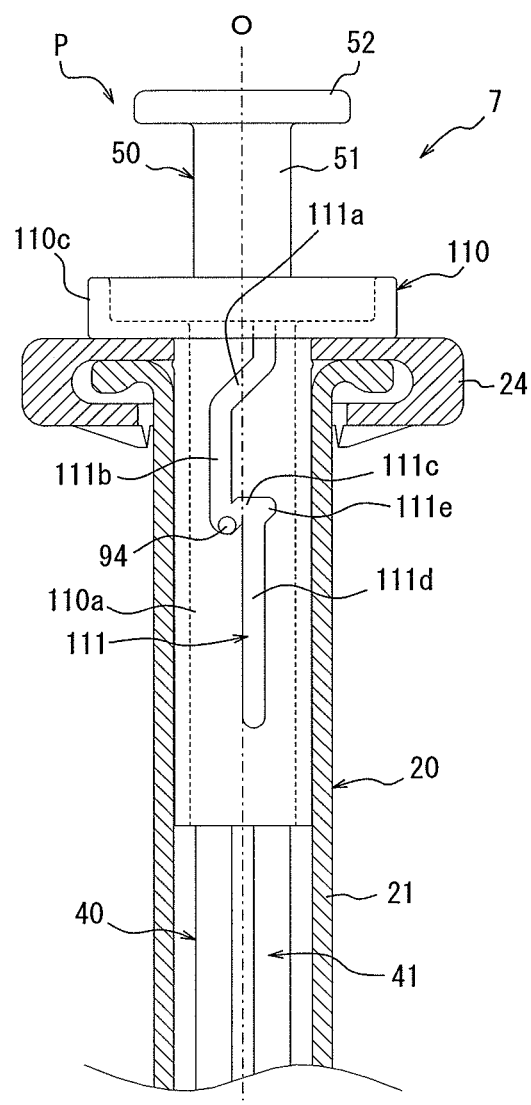
FIG. 31B is a view taken along a partial section illustrating the state of FIG. 31A as viewed from another side.

Here, a description is given of a method of use of the present embodiment. From the state illustrated in FIG. 30 (FIG. 28A), the plunger operation member 50 is pushed in. Then, as illustrated in FIG. 31A, the main body end surface 51a presses the pressed surface 90f of the pressed portion 90 provided in the piston holding member 40. As a result, the piston holding member 40, together with the plunger operation member 50, is pushed into the sleeve member 110. At this time, the protrusions 94 of the pressed portion 90 are displaced along the torsion passage 111a of each crank 111. As a result, as the piston holding member 40 is pushed in, torsion around the axis line O is provided to the torsion spring portion 93. Furthermore, as illustrated in FIG. 31A, when the plunger operation member 50 is pushed in, as illustrated in FIG. 31B, the protrusions 94 of the pressed portion 90 are displaced along the first push-in passage 111b from the torsion passage 111a of the crank 111. As a result, the piston holding member 40 is pushed in further while the torsion provided to the torsion spring portion 93 is maintained. Accordingly, the plunger P is able to eject a metered quantity of the content C through the ejection orifice A1 until the protrusions 94 reach an end of the first push-in passage 111b.

When the protrusions 94 reach an end of the first push-in passage 111b, the plunger operation member 50 may not be pushed in anymore. Then, the first ejection is completed while the content C still remains in the room R. The volume of the room R at this time may be appropriately determined in accordance with intended use and may be half the volume of the room R prior to the start of the ejection, for example.

Figure 32A:
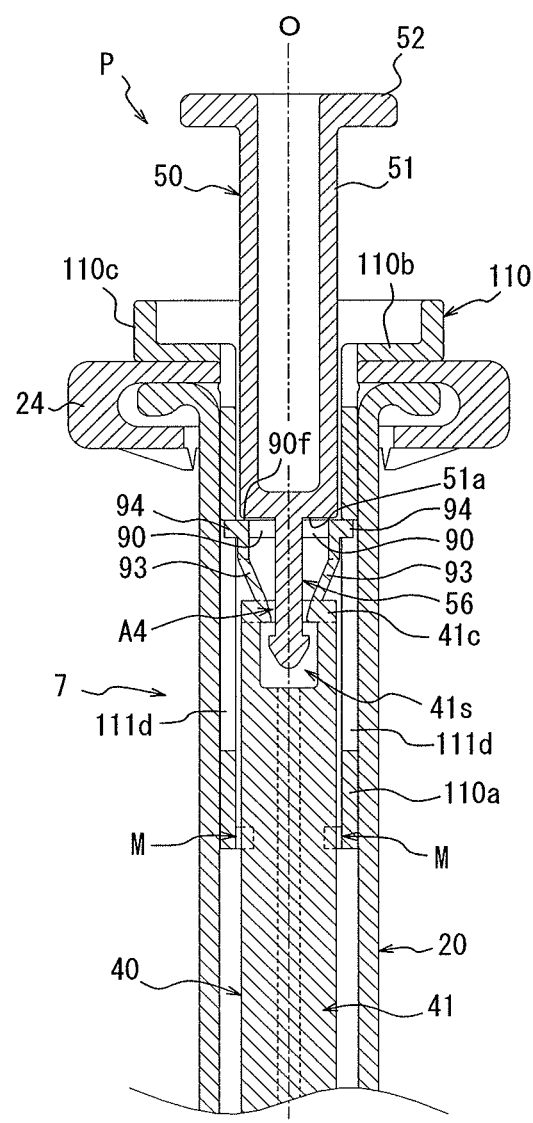
FIG. 32A is an enlarged sectional view illustrating a state where the pushing of a plunger is released for starting a second ejection in the nasal spray dispenser of FIG. 28A as viewed from one side.
Figure 32B:
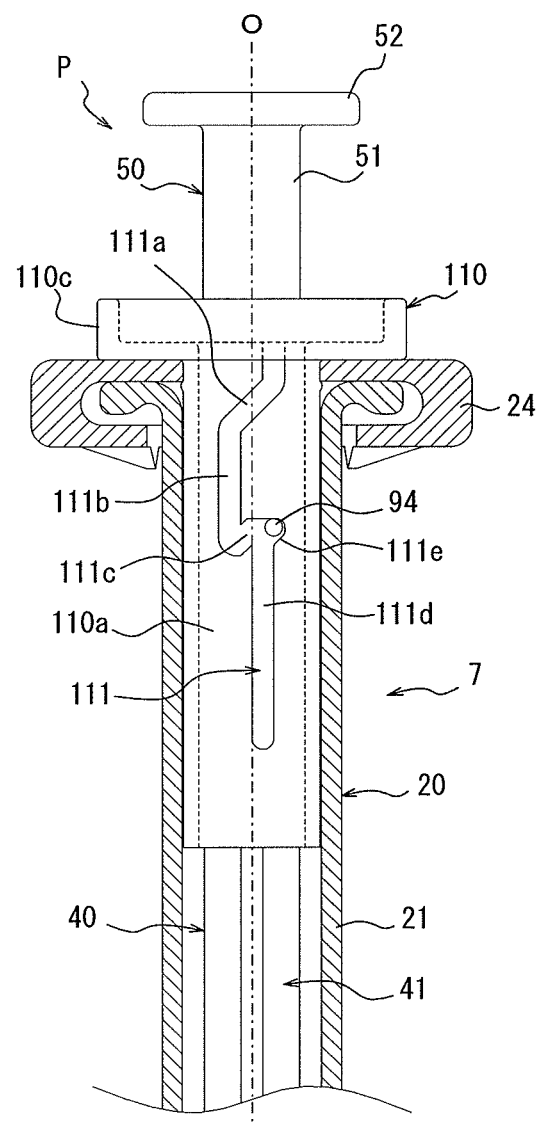
FIG. 32B is a view taken along a partial section illustrating the state of FIG. 32A as viewed from another side.

Subsequently, the pushing of the plunger operation member 50 is released. Then, pressure to the pressed portion 90 is released, and accordingly, the torsion deformation caused in the torsion spring portion 93 is also released. As a result, due to restoring force of the torsion spring portion 93, as illustrated in FIG. 32A, the pressed portion 90 is pushed back away from the main body 41. As a result, as illustrated in FIG. 32B, the protrusions 94 of the pressed portion 90 are displaced from the first push-in passage 111b to the second push-in passage 111d (the retreating portion 111e) along the return passage 111c. Accordingly, the piston holding member 40 may be pushed in again along the second push-in passage 111d of each crank 111.

Figure 33A:
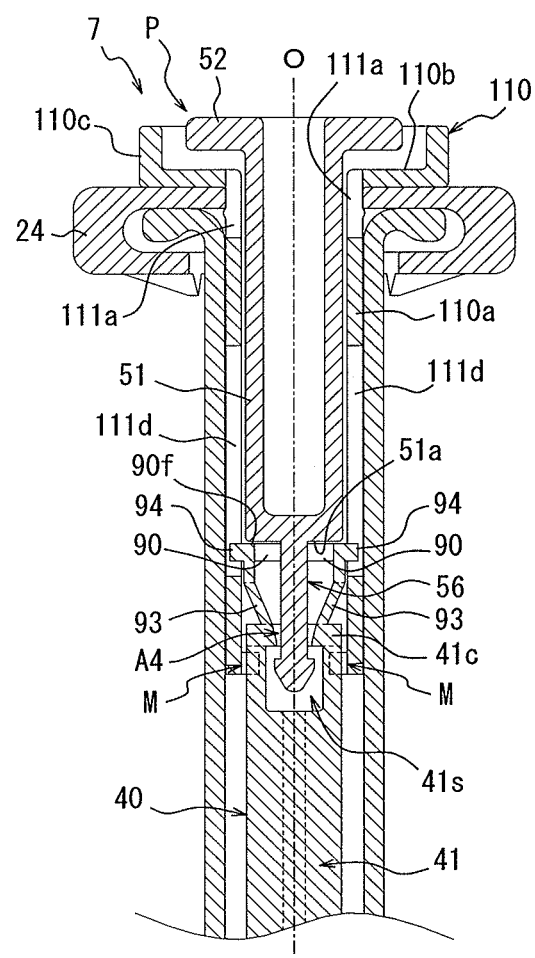
FIG. 33A is an enlarged sectional view illustrating a state where the second ejection is completed in the nasal spray dispenser of FIG. 28A as viewed from one side.
Figure 33B:
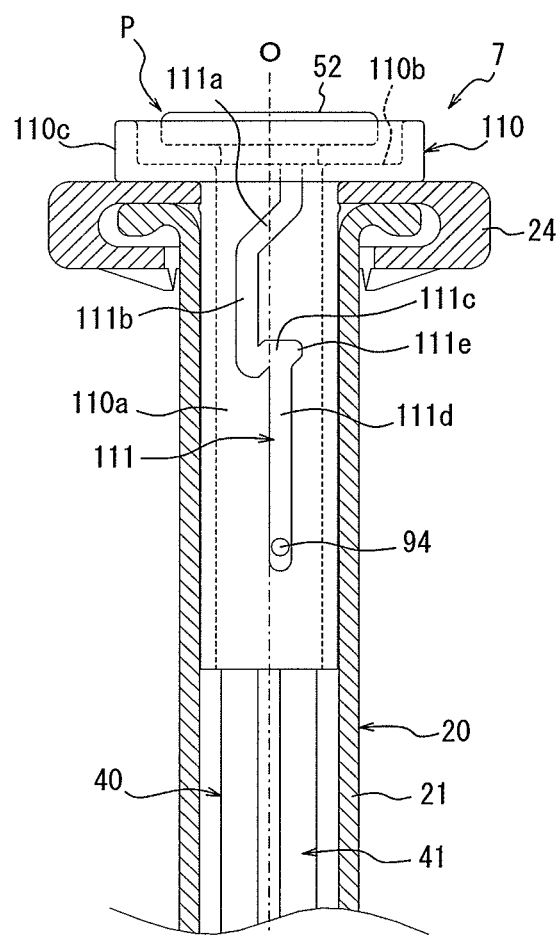
FIG. 33B is a view taken along a partial section illustrating the state of FIG. 33A as viewed from another side.

In the present embodiment, as illustrated in FIG. 32B, the protrusions 94 of the pressed portion 90 are hooked in the retreating portion 111e. Furthermore, the retreating portion 111e is configured to release the protrusions 94 from being hooked when the plunger operation member 50 is pushed in. With the above structure, in the present embodiment, by releasing the pushing of the plunger operation member 50 and subsequently, by pushing in the plunger operation member 50 again more strongly, as illustrated in FIG. 33B, the remaining content C may be ejected through the ejection hole A1 until the protrusions 94 come into contact with the end of the second push-in passage 111d. Thus, in the present embodiment, after the pushing of the plunger operation member 50 is released, by pushing in the plunger operation member 50 again strongly, the second ejection is achieved.

In the present embodiment, the detent around the axis line O of the piston holding member 40 may be also achieved by kinetic friction force generated between the piston 30 and the inner circumferential surface 20f of the syringe around the axis line O. However, by providing the additional detent mans M as in the present embodiment, the piston holding member 40 is operated stably along each crank 111, and therefore, the two-step ejection is reliably achieved.

Various modifications may be made to the above description. For example, although, by arranging the crank 111 in the two positions opposing to each other about the axis line O as in the present embodiment, the piston holding member 40 is operated stably along the cranks 111, it is only necessary to arrange the crank 111 in a single position. Although in the present embodiment the crank 111 is configured by the through hole, according to the present invention, the crank 111 may also be configured by a recessed groove formed in the inner circumferential surface of the trunk portion 110a. Furthermore, by providing the crank 111 with a plurality of bent portions (push-in passages and return passages), ejection may be achieved in three or more steps.

Figure 34:
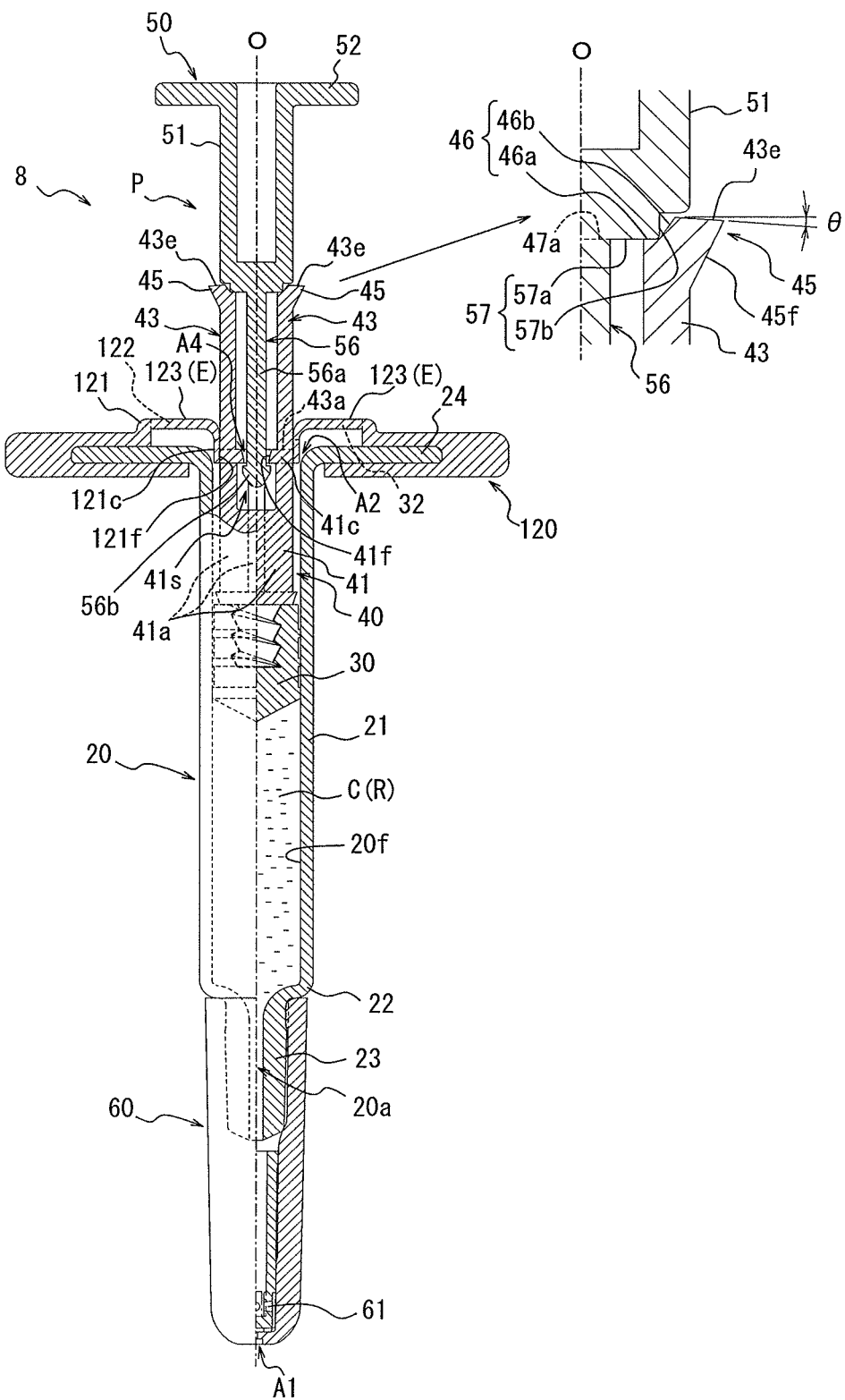
FIG. 34 is a side view taken along a partial section illustrating a nasal spray dispenser that is in an initial state prior to an operation thereof, and a partially enlarged view of the nasal spray dispenser, according to Embodiment 8 of the present invention.

FIGS. 34-38 illustrate a nasal spray dispenser according to Embodiment 8 of the present invention. In the following, configurations substantially the same as those of other embodiments are denoted by the same reference numerals. In FIG. 34, reference numeral 8 refers to a synthetic resin nasal spray dispenser according to Embodiment 8 of the present invention. Reference numeral 120 refers to a finger rest cover fixed to the finger rest 24 of the syringe 20. In the present embodiment, as illustrated in FIG. 35A, the finger rest cover 120 has an appearance in the form of an elliptical disk member. With the above structure, a region 120a provided on both sides in a major axis direction constitutes a region in which fingers rest.

Figure 35A:
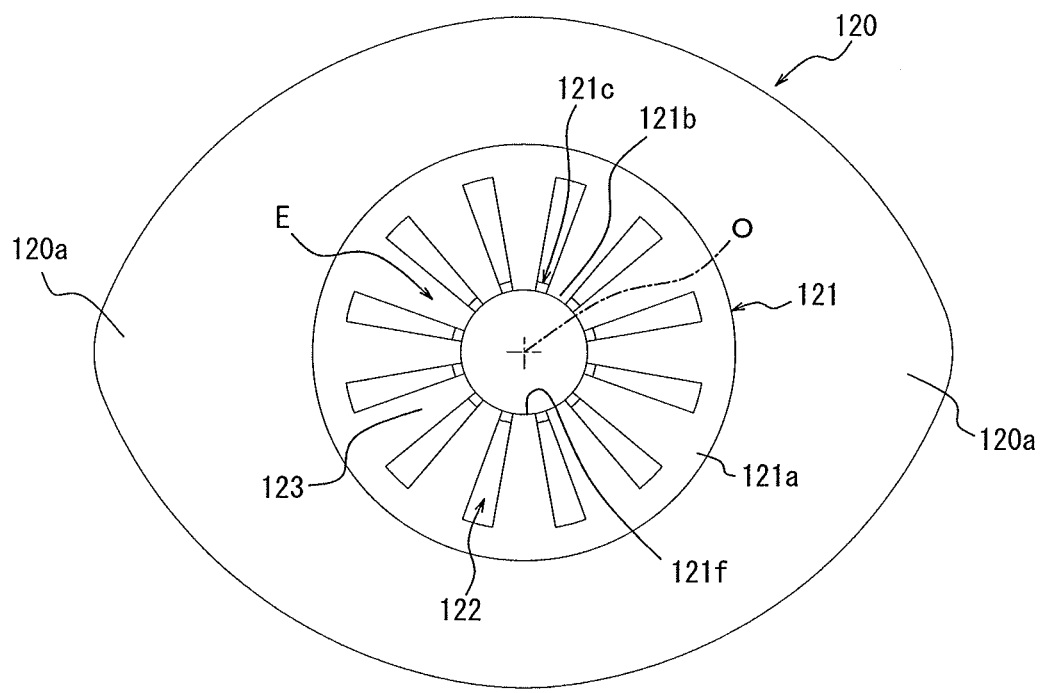
FIG. 35A is a plan view schematically illustrating a finger rest cover of FIG. 34 from a side thereof on which fingers rest.
Figure 35B:
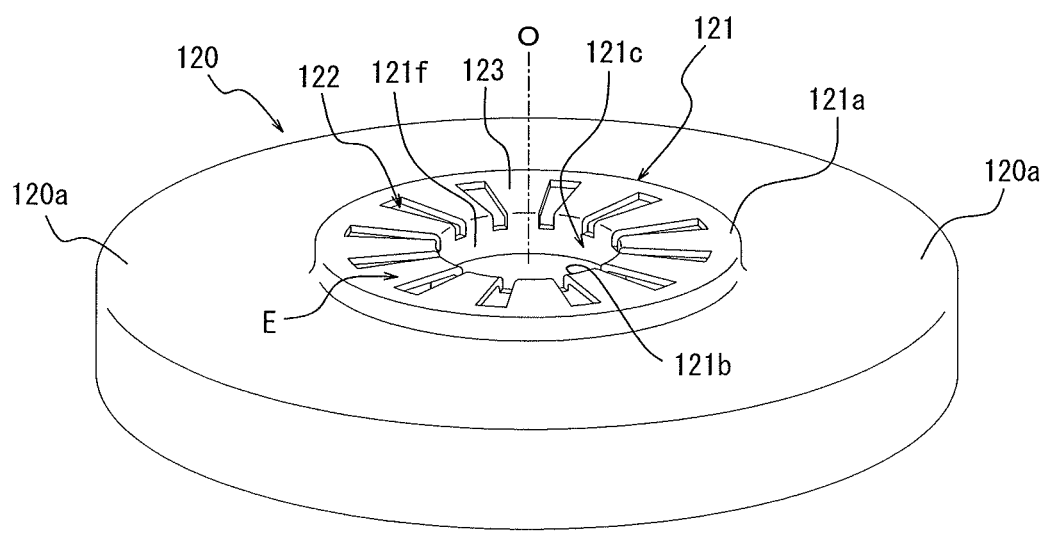
FIG. 35B is a perspective view schematically illustrating the finger rest cover of FIG. 34 from a side thereof on which fingers rest.

The finger rest cover 120 is provided, in middle thereof, with a partition wall 121. As illustrated in FIG. 35B, the partition wall 121 has a hollow circular shape projecting annually. The partition wall 121 includes a tubular body portion 121c extending toward the opening A2 provided in the rear end of the syringe 20. In the present embodiment, the partition wall 121 includes a flat annular portion 121a having a small-thickness that is formed from an outer edge portion of the partition wall 121 toward the middle. Furthermore, the partition wall 121 includes a cone-shaped curved portion 121b formed by an inner edge of the annular portion 121a of the partition wall 121 that has a diameter decreasing toward the opening A2 provided in the rear end of the syringe. The curved portion 121b has a front end portion having a constant diameter, and thus, forms a tubular body portion 121c.

The partition wall 121 also includes an elastic region E formed around the tubular body portion 121c. The elastic region E supports the tubular body portion 121c in a manner such that the tubular body portion 121c may be deformed and restored. In the present embodiment, the partition wall 121 is provided, in the elastic region E, with a plurality of slits 122 arranged at an interval about the axis line O and a plurality of connecting pieces 123 each provided between adjacent slits 122.

In the present embodiment, each slit 122 extends in the radial direction via the corresponding curved portion 121b between the annular portion 121a and an upper edge portion of the tubular body portion 121c. That is to say, each connecting piece 123 extends in the radial direction between the annular portion 121a and the upper edge portion of the tubular body portion 121c. Furthermore, in the present embodiment, as illustrated in FIG. 35A, the slit 122 is formed in a wedge-shape so that a slit width increases as the slit 122 extends outward in the radial direction from the upper end portion of the tubular body portion 121c. The connecting piece 123 is also formed in a wedge shape so that a width thereof increases as the connecting piece 123 extends outward in the radial direction from the upper end portion of the tubular body portion 121c. In FIGS. 35A and 35B, for simplification of the figures, reference numerals 122 and 123 are each assigned exemplarily to a single position alone.

In FIG. 34, reference numeral P refers to a synthetic resin plunger that is accommodated in the syringe 20. The plunger P includes the piston holding member 40 and the plunger operation member 50 disposed in the rear of the piston holding member 40.

The piston holding member 40 includes the main body 41 configured to hold the piston 30. The main body 41 includes the elongate four plate portions 41a and the ring portion 41c in an integrated manner. The four plate portions 41a are formed in a cross shape. The ring portion 41c is provided with the through hole A4. The through hole A4 communicates with the open space 41s that is formed by cutting the plate portions 41a. The through hole A4 is configured by a tapered surface constituted by the inner circumferential surface 41f of the ring portion 41c whose diameter decreases towards the front end (the piston 30).

The main body 41 is provided with the two arms 43 integrally formed therewith. The arms 43 are positioned in a manner such that the arms 43 oppose to each other across the through hole A4. The arms 43 each have a plate shape and extend rearward from the ring portion 41c along the axis line O. Each arm 43 may be deformed inward in the radial direction (the direction perpendicular to the axis line O) from the fixed end 43a, when loaded with external force. The arm 43 may also be restored to the initial position when the load is released. With the above structure, the free end 43e of the arm 43 may be displaced inward in the radial direction and may be restored to the initial position. In the present embodiment, the arm 43 is formed in a small thickness, and accordingly, the arm 43 is easily deformed and restored. In the present embodiment, the arm 43 is not provided with the slide projection 44 as illustrated in FIG. 9 according to Embodiment 3.

As illustrated in FIG. 34, each arm 43 extends through the tubular body portion 121c of the finger rest cover 120. The arm 43 is slidably held by the inner circumferential surface 121f of the tubular body portion 121c. Furthermore, as illustrated in FIG. 34, the protrusions 45 of the two arms 43 opposing to each other about the axis line O have an interval between outermost diameters thereof in the radial direction that is greater than the diameter of the opening provided in a rear end of the tubular body portion 121c (an inner diameter of the tubular body portion 121c). With the above structure, when in contact with the elastic region E of the finger rest cover 120 (the connecting piece 123 in the present embodiment), the protrusion 45 of each arm 43 is locked, and as a result, the pushing of the plunger operation member 50 is stopped. Furthermore, as illustrated in an enlarged view of FIG. 34, the protrusion 45 of each arm 43 includes, in an outer side thereof, an inclined surface 45f that tapers toward the fixed end 43a. With the above structure, when the arm 43 undergoes inward deformation starting from the fixed end 43a, the protrusion 45 of the arm 43 may easily enter by the inner circumferential surface 121f of the tubular body portion 121c and may slide along the inner circumferential surface 121f.

In the present embodiment, the protrusion 45 is formed at the free end 43e of the arm 43 in an integrated manner. Accordingly, in the present embodiment, a rear end surface of the protrusion 45 constitutes the free end 43e of the arm. In the present embodiment, as illustrated in the enlarged view of FIG. 34, the free end 43e of the arm 43 is configured by a taper inclined outward (i.e. inclined inward as the free end 43e advances rearward) at an angle θ with respect to the horizontal line perpendicular to the axis line O. However, the free end 43e of the arm 43 may be formed as a flat surface parallel to the horizontal line. Value of θ may be appropriately changed depending on the size of the nasal spray dispenser or the like. For example, the angle θ is set in a manner such that, when the arm 43 is inclined inward, the arm 43 is parallel to the horizontal line perpendicular to the axis line O.

Furthermore, in the present embodiment, the free end 43e of the arm 43 is provided with the step 46. The step 46 is formed on the inner side of the arm 43. In the present embodiment, as illustrated in FIG. 34, the step 46 includes the flat step bottom surface 46a and the step side surface 46b connected to the step bottom surface 46a. In the present embodiment, the step side surface 46b is also formed as the tapered surface that is inclined rearward and outward from the step bottom surface 64a.

Furthermore, as illustrated in FIG. 9 according to Embodiment 3, the main body 41 of the piston holding member 40 is provided with the two support portions 47 in an integrated manner. The support portions 47 are positioned in a manner such that the support portions 77 oppose to each other across the through hole A4. The support portion end surfaces 47a each constitute a flat surface whose length measured from the ring portion 41c corresponds to the step bottom surface 46a provided in the arm 43.

On the other hand, the plunger operation member 50 includes the main body 51 that is provided, at the rear end thereof, in an integrated manner with the plunger operation portion 52 for the user to push in the plunger P. The main body 51 has a cylindrical shape. The front end portion of the main body 51 is formed as the convex portion 57. The convex portion 57 has a cylindrical shape and includes the flat convex portion end surface 57a and the convex portion side surface 57b connected to the convex portion end surface 57a. As illustrated in the enlarged view of FIG. 34, the convex portion end surface 57a is configured to come into contact with the step bottom surface 46a and the support portion end surface 47a of the piston holding member 40. With the above structure, when the plunger operation member 50 is pushed in, the convex portion end surface 57a presses the step bottom surface 46a and the support portion end surface 47a of the piston holding member 40, whereby the pushing movement of the plunger P as a whole is achieved. That is to say, the step bottom surface 46a and the convex portion end surface 57a constitute the pressing surface that restrains the arm 43 and that presses the piston holding member 40. On the other hand, since the step side surface 46b of the piston holding member 40 is configured by the tapered surface, the convex portion side surface 57b is capable of slidably contacting the step side surface 46b. With the above structure, when the arm 43 undergoes inward deformation, the step side surface 46b of the piston holding member 40, as the guide for the convex portion side surface 57b of the plunger operation member 50, is capable of pushing back the plunger operation member 50 outward along the axis line O. That is to say, the step side surface 46b of the piston holding member 40 and the convex portion side surface 57b of the plunger operation member 50 constitute a guide portion for pushing back the plunger operation member 50 in response to the inward deformation of the arm 43.

The main body 51 of the plunger operation member 50 is also provided with the shaft 56 in an integrated manner. The shaft 56 includes the shaft body 56a having a diameter smaller than the diameter of the convex portion end surface 57a. The shaft body 56a extends from the convex portion end surface 57a toward the front end thereof along the axis line O. The shaft body 56a is provided, at the front end thereof, with the head 56b having a diameter greater than the diameter of the shaft body 56a, in an integrated manner. The head 56b includes the inclined surface 56f that tapers toward the front end thereof. The shaft 56 is fitted to and held by the through hole A4 formed in the piston holding member 40. The through hole A4 has an inner diameter that is greater than the diameter of the shaft body 56a and smaller than the diameter of the head 56b. As illustrated in FIG. 34, the through hole A4 lets the shaft body 56a penetrate therethrough and also holds the head 56b by preventing the head 56b from slipping off. The head 56b and the inner circumferential surface 41f of the ring portion 41c hold the piston holding member 40 to the plunger operation member 50 by preventing the piston holding member 40 from slipping off. In the present embodiment in particular, the inner circumferential surface 41f of the ring portion 41c is formed by a tapered surface whose diameter decreases toward the front end. With the above structure, the head 56b may be easily assembled to the end surface of the ring portion 41c that is on the side of the front end (i.e. the end surface of the ring portion 41c near the piston 30). The open space 41s, which is formed by cutting the plate portions 41a, defines play space in which the head 56b is displaceable forward and rearward along the axis line O. With the above structure, the piston holding member 40 and the plunger operation member 50 may be displaceably coupled to each other along the axis line O.

The piston 30 is provided in the front end portion of the main body 41 and accommodated in the syringe 20. The piston 30 is made of an elastic material such as rubber or the like and is slidably held on the inner circumferential surface 20f of the trunk portion 21 of the syringe.

Between the syringe 20 and the piston 30, the room R is formed. The room R is configured to be filled with the content C. The content C filled in the room R is pumped to the through hole 20a formed in the front end portion 23 in response to pushing of the piston 30.

In FIG. 34, reference numeral 60 refers to a nozzle fitted to the front end portion 23 of the syringe. The nozzle 60 includes the built-in chip 61 and is capable of ejecting the content C, which has been pumped through the through hole 20a, through the ejection orifice A1.

Figure 36:
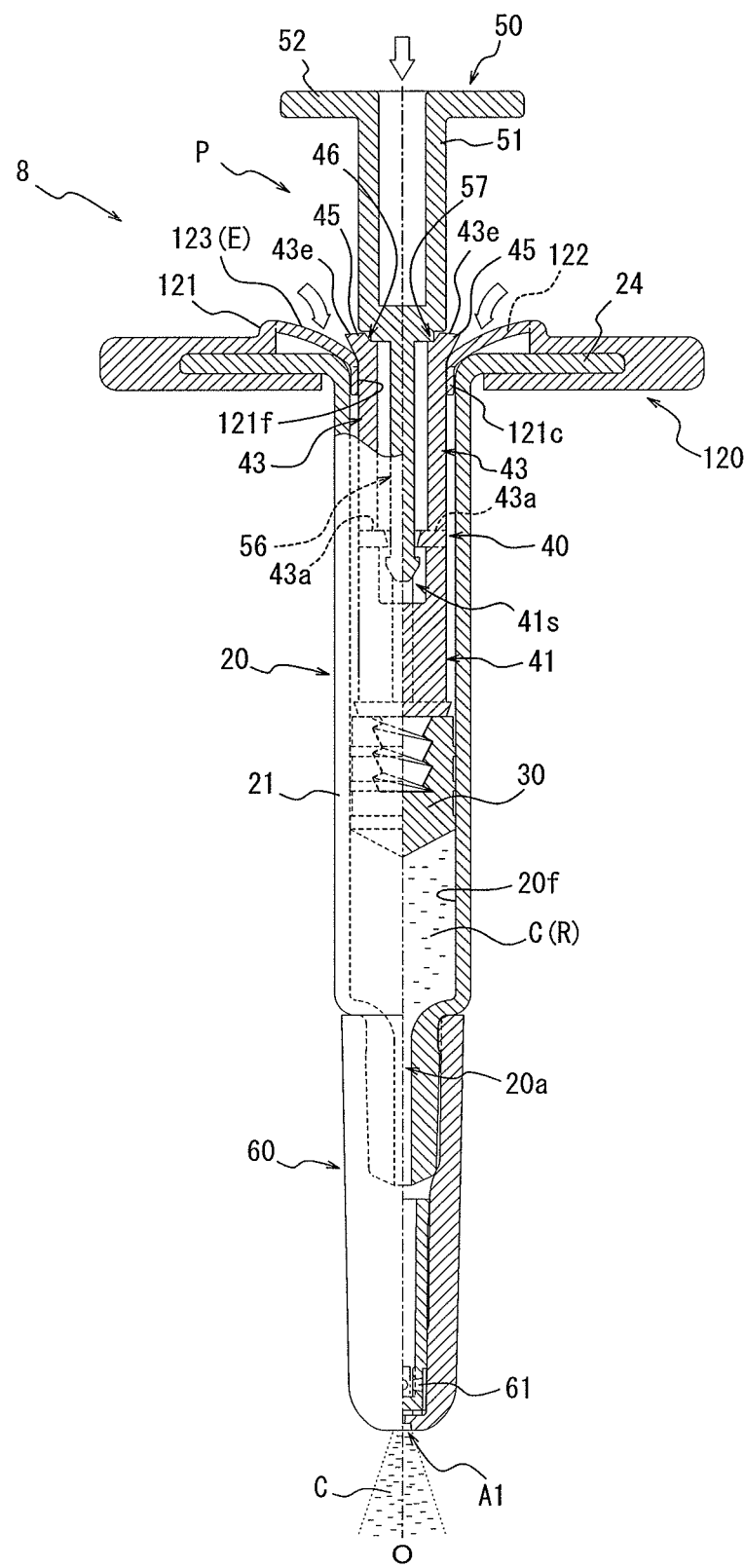
FIG. 36 is a side view taken along a partial section illustrating a state where a first ejection is completed in the nasal spray dispenser in FIG. 34.

Here, a description is given of a method of use of the present embodiment. From the state illustrated in FIG. 34, the plunger operation member 50 is pushed in. Then, the piston holding member 40 passes through the tubular body portion 121c of the finger rest cover 120 and is pushed into the syringe 20. As illustrated in FIG. 36, the pushing is stopped when the protrusion 45 provided in the arm 43 contacts the elastic region E (the connecting piece 123 in the present embodiment) of the finger rest cover 120 to be locked. As illustrated in FIG. 36, the contact causes the elastic region elastic E to undergo elastic deformation. Thus, the piston holding member 40 is capable of ejecting a metered quantity of the content C through the ejection orifice A1 until the protrusion 45 provided in the arm 43 is hooked in the elastic region E to be locked.

When the protrusion 45 provided in the arm 43 comes into contact with the elastic region E, the plunger holding member 50 may not be pushed in anymore. Then, the first ejection is completed while the content C still remains in the room R. The volume of the room R at this time may be appropriately determined in accordance with intended use and may be half the volume of the room R prior to the start of the ejection, for example.

Figure 37:
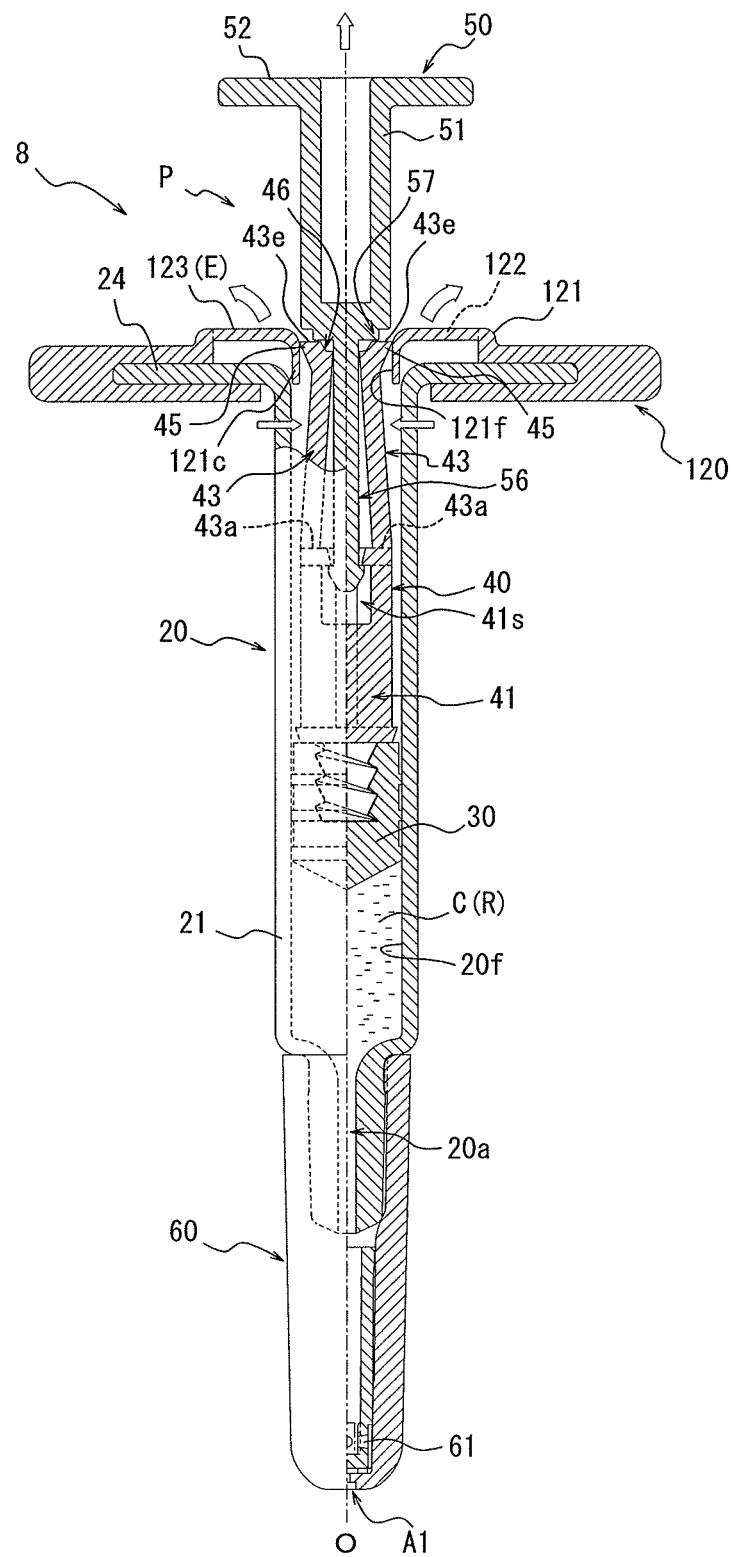
FIG. 37 is a side view taken along a partial section illustrating a state where the pushing of a plunger is released for starting a second ejection in the nasal spray dispenser of FIG. 34.

Subsequently, when the pushing of the plunger operation member 50 is released, pressure to the free end 43e of the arm 43 is released. Consequently, the deformation of the elastic region E is instantly restored. At this time, due to the instant restoration of the elastic region E, the protrusion 45 of the arm 43 slips into the tubular body portion 121c and undergoes inward deformation starting from the fixed end 43a while pushing back the plunger operation member 50. As a result, as illustrated in FIG. 37, the locking of the protrusion 45 is released, and the protrusion 45 is hooked on an inner side of the elastic region E (e.g. an inner side of the curved portion 121b or the tubular body portion 121c) to be held on the inner side of the elastic region E. With the above structure, after the pushing of the plunger operation member 50 is released, by pushing the plunger operation member 50 further with force that is greater than the holding force resulting from the inner side of the elastic region E being hooked by the protrusion 45, the protrusion 45 held on the inner side of the elastic region E slides inside the tubular body portion 121c against the holding force of the elastic region E, and accordingly, the piston holding member 40 may be pushed in again.

Figure 38:
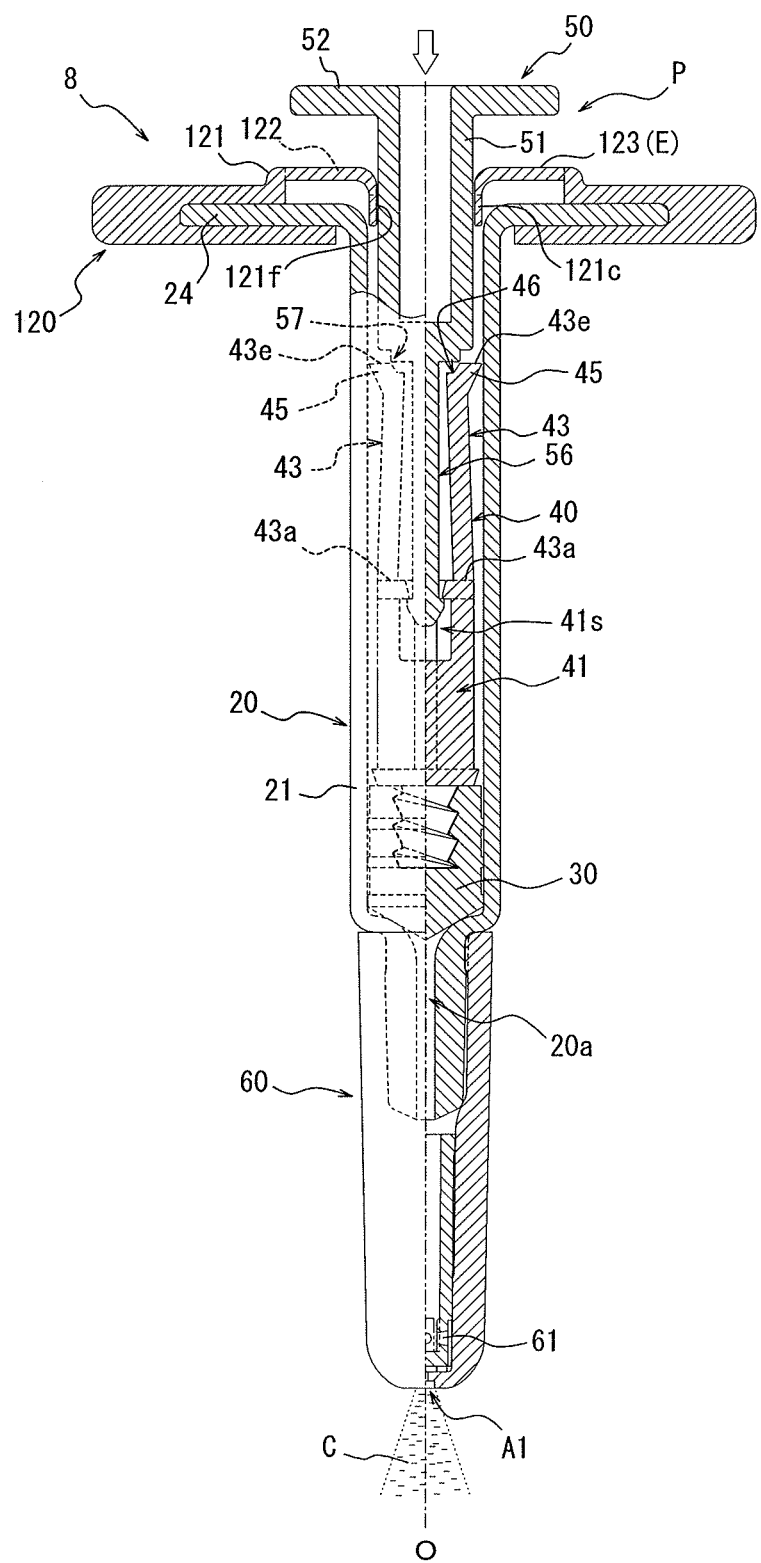
FIG. 38 is a side view taken along a partial section illustrating a state where the second ejection is completed in the nasal spray dispenser of FIG. 34.

Accordingly, after the pushing of the plunger operation member 50 is released, by pushing in the plunger operation member 50 again, as illustrated in FIG. 38, the content C remaining in the room R is ejected through the ejection orifice A1.

Meanwhile, although the elastic region E may be made of an elastic material or the like, by configuring the elastic region E by the plurality of connecting pieces 123 each provided between adjacent slits 122 as in the present embodiment, a large amount of restoration is instantly achieved even when a relatively hard material is adopted in the elastic region E. In the above circumstance, when the pushing of the plunger operation member 50 is released, the state where the protrusion 45 is locked as illustrated in FIG. 36 transitions to the state where the protrusion 45 is held on the inner side of the elastic region E as illustrated in FIG. 37, while the plunger operation member 50 is easily pushed back. Accordingly, the locking state of the protrusion 45 provided in the arm 43 and the inner side of the elastic region E is quickly released.

Furthermore, as in the present embodiment, by forming the step side surface 46b provided in the arm 43 of the piston holding member 40 as the tapered surface and by forming the convex portion 57 provided in the main body 51 of the plunger operation member 50 in the cylindrical shape, the inward deformation of the arm 43 is easily achieved.

Meanwhile, among syringe-type dispensers, there is the one that includes: a first piston that is arranged on a side of a front end of a syringe, a first agent C1 being filled between the side of the front end of the syringe and the first piston; a second piston provided in a plunger, a second agent C2 being filled between the first piston and the second piston, wherein the first piston is displaced in response to pushing of the second piston so as to form a bypass (a detour) between a concave portion and the first piston, the concave portion being provided on an inner circumferential surface of the syringe, and the first agent C1 is mixed with the second agent C2 to be withdrawn as a content.

However, in the conventional syringe-type dispenser, the plunger may be arbitrarily pushed in to reach the side of the front end of the syringe. Accordingly, when the piston arranged in the syringe passes the concave portion in a short period of time, the bypass does not function effectively, and as a result, the first agent C1 might be ejected without being fully permeated with the second agent C2. In view of the above, a user is required to carefully operate the plunger, and there is room for improvement in terms of operability.

Figure 39:
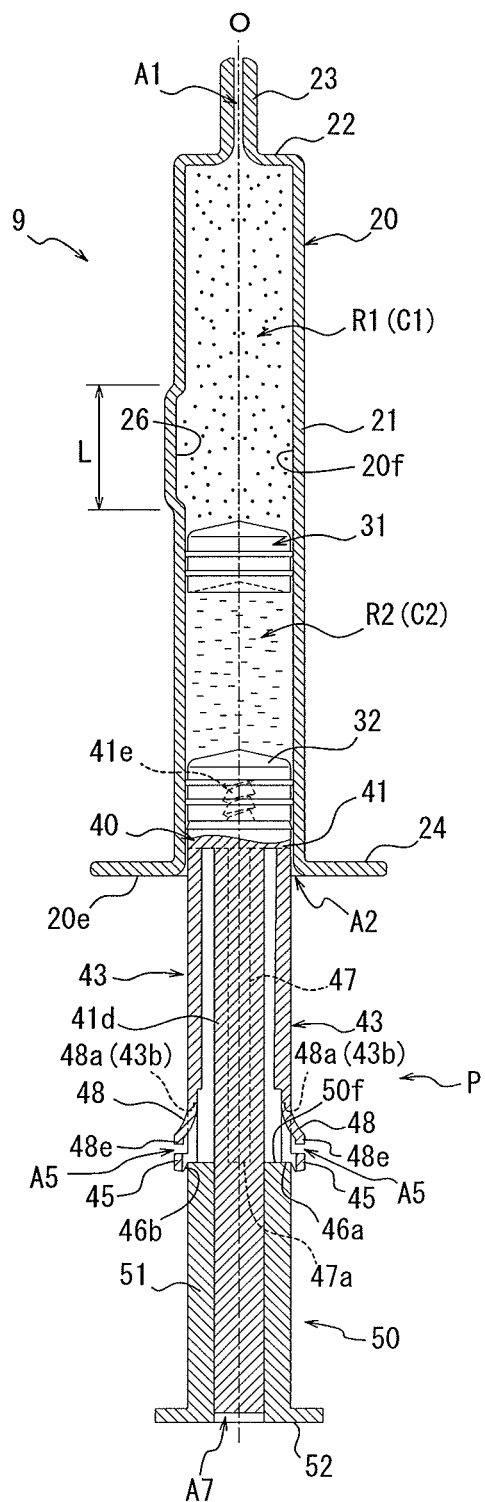
FIG. 39 is a side view taken along a partial section illustrating a syringe-type dispenser that is in an initial state prior to an operation thereof, according to Embodiment 9 of the present invention.

FIGS. 39-43 illustrate a nasal spray dispenser according to Embodiment 9 of the present invention. In the following, configurations substantially the same as those of other embodiments are denoted by the same reference numerals. In FIG. 39, reference numeral 9 refers to a syringe-type dispenser according to Embodiment 9 of the present invention. In the present embodiment, a first piston 31 is arranged in the syringe 20 in advance through the opening A2 provided in the rear end of the syringe 20. The first piston 31 is made of an elastic material such as rubber or the like and is slidably held on the inner circumferential surface 20f of the trunk portion 21 of the syringe. Accordingly, on the side of the front end of the syringe 20, there is formed the front end side filling room R1 that is sealed by the first piston 31. In the filling room R1, the first agent C1 is filled as the content. Examples of the first agent C1 include freeze-dried powder medicine.

Reference numeral P refers to a synthetic resin plunger accommodated in the syringe 20. The plunger 80 includes the piston holding member 40. The piston holding member 40 includes the main body 41 configured to hold a second piston 32. The main body 41 is provided, in the front end thereof, with the screw portion 41e. In the present embodiment, the second piston 32 is fitted by the screw portion 41e. Similarly to the first piston 31, the second piston 32 is made of an elastic material such as rubber or the like and is slidably held on the inner circumferential surface 21f of the trunk portion 21 of the syringe. Accordingly, on the side of the rear end of the syringe 20, there is formed filling room R2 that is sealed by the first piston 31 and the second piston 32. In the filling room R2, the second agent C2 is filled as the content. Examples of the second agent C2 include a solution that dissolves freeze-dried powder medicine.

The main body 41 of the piston holding member 40 includes the shaft portion 41d extending rearward. In the present embodiment, the shaft portion 41d is in the form of a round bar. However, according to the present invention, the shaft portion 41d may have any cross sectional shape such as a rectangular shape. The main body 41 is provided with the two arms 43 integrally formed therewith. The arms 43 are positioned in a manner such that the arms 43 oppose to each other across the shaft portion 41d. As illustrated in FIG. 14 according to Embodiment 4, the arms 43 each have a shape along an outer circumferential surface of the main body 41 and extend rearward from the main body 41 along the axis line O. Each arm 43 may be deformed inward in the radial direction (the direction perpendicular to the axis line O) from the fixed end 43a, when loaded with external force. The arm 43 may also be restored to the initial position (the position illustrated in FIG. 39) when the load is released. With the above structure, the free end 43e of the arm 43 may be displaced inward in the radial direction and may be restored to the initial position.

The arms 43 are also each provided with an elastic tongue piece 48. As illustrated in FIG. 14 according to Embodiment 4, the elastic tongue piece 48 is arranged in the opening A5 formed in the arm 73. The elastic tongue piece 48 has the fixed end 48a formed in an integrated manner with respect to, among edge portions constituting the opening A5, the opening edge portion 43b that is on the side of the front end (the fixed end 43a of the arm 43). The fixed end 48a of the elastic tongue piece 48 constitutes the same surface as the outer surface of the arm 43. In the present embodiment, the arm 43 is formed in a small thickness and therefore, is easily deformed and restored. The elastic tongue piece 48 is formed in a smaller thickness than the arm 43.

The elastic tongue piece 48 is curved outward in the radial direction as the elastic tongue piece 48 advances toward the free end 43e of the arm 43. Accordingly, the end 48e of the elastic tongue piece 43 is oriented outward in the radial direction. Furthermore, as illustrated in FIG. 39, the two ends 48e opposing to each other about the axis line O have an interval between outermost diameters thereof in the radial direction that is greater than the inner diameter of the syringe 20 (which is the same as the diameter of the opening A2 provided in the rear end of the syringe 20 in the present embodiment). With the above structure, when the elastic tongue piece 48 comes into contact with the opening A2 provided in the rear end of the syringe 20, a portion of the elastic tongue piece 48 that is on the side of the end 48e serving as the free end undergoes flexure deformation starting from the fixed end 48a of the elastic tongue piece 48. As a result, the elastic tongue piece 48 enters the syringe 20. In the present embodiment, since the elastic tongue piece 48 is curved outward, the elastic tongue piece 48 may easily enter the syringe 20 though the opening A2 provided in the rear end of the syringe 20. Furthermore, with the end 48e, the elastic tongue piece 48 is allowed to slide on the inner circumferential surface 20f of the syringe.

The arms 43 are also each provided with a protrusion 45 in an integrated manner. In the present embodiment, the protrusion 45 is formed at the free end 43e of the arm 43 in an integrated manner. Accordingly, in the present embodiment, the rear end surface of the protrusion 45 constitutes the free end 43e of the arm 43. In the present embodiment, the free end 43e of the arm 43 is configured by a taper inclined outward (i.e. inclined inward as the free end 43e advances rearward) at an angle θ with respect to the horizontal line perpendicular to the axis line O. (Refer to the enlarged view of FIG. 1.) Value of θ may be appropriately changed depending on the size of the syringe-type dispenser or the like. However, according to the present invention, the free end 43e of the arm 43 may be configured by forming the rear end surface of the protrusion 45 to be a flat surface parallel with the horizontal line when the arm 43 is in the initial state.

Moreover, in the present embodiment, as illustrated in FIG. 39, the end 48e of the elastic tongue piece 48 (a portion of the elastic tongue piece 48 that is on the side of the free end) is positioned closest to the protrusion 45. Furthermore, in the present embodiment, the protrusion 45 is provided with the step 46 as illustrated in FIG. 14 according to Embodiment 4. The step 46 is formed on an inner side of the arm 43 and includes the flat step bottom surface 46a and the step side surface 46b connected to the step bottom surface 46a. The step bottom surface 46a constitutes a pressed surface. The step side surface 46b is also formed as the tapered surface that is inclined rearward and outward.

The main body 41 is also provided in an integrated manner with the two support portions 47 extending along the axis line O. (Refer to FIG. 14.) The support portions 77 are positioned in a manner such that the support portions 77 oppose to each other across the shaft portion 41d. Each support portion end surface 47a constitutes a flat surface whose length measured from the main body 41 corresponds to the step bottom surface 46a provided in the arm 43. With the above structure, in the present embodiment, the support portion end surface 47a, together with the step bottom surface 46a, constitutes the pressed surface.

On the other hand, in FIG. 39, reference numeral 50 refers to the plunger operation member. The plunger operation member 50 includes the cylindrical main body 51 and the plunger operation portion 52. The main body 51 includes, inside thereof, the through hole A7. The through hole A7 lets the shaft portion 41d slidably penetrate therethrough. The plunger operation member 50 is positioned relative to the piston holding member 40 in the direction of the axis line O by the end surface 50f of the plunger operation member 50 that is on the side of the main body coming into contact with the step bottom surface 46a and the support portion end surface 47a of the piston holding member 40. In the present embodiment, the plunger operation member 50 is press-fitted in a slidable manner with respect to the shaft portion 41d of the piston holding member 40. As illustrated in FIG. 39, the plunger operation member 50 is provided, at the rear end thereof, with the plunger operation portion 52. The plunger operation portion 52 is formed as an operation portion for the user to push in the plunger P. As a result, the piston holding member 50 is capable of pushing the plunger operation member 40 into the syringe 20. That is to say, as long as the first piston 31 maintains a liquid tight state with respect to the syringe 20, the second agent C2 filled in the filling room R2 presses the first piston 31 toward the front end portion 23 in response to pushing of the plunger P.

Figure 40:
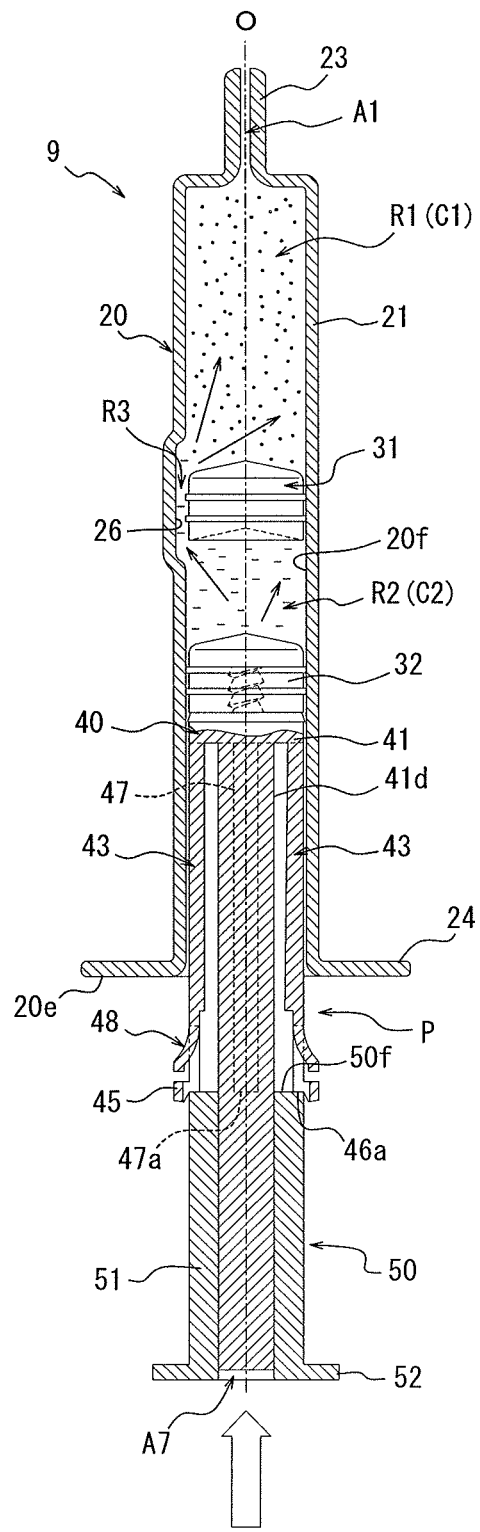
FIG. 40 is a side view taken along a partial section illustrating a state where a bypass is formed in the syringe-type dispenser of FIG. 39.

Moreover, the trunk portion 21 of the syringe 20 is provided, on a side of the inner circumferential surface 20f thereof, with a concave portion 26. The concave portion 26 is provided at least in a single position around the axis line O in the filling room R1 provided on the side of the front end of the syringe 20. As illustrated in FIG. 39, the concave portion 26 extends along the axis line O and has a length L that is greater than a total length of the first piston 31 (a total length of a sliding portion). With the above structure, when the first piston 31 is displaced toward the front end of the syringe 20, as illustrated in FIG. 40, a bypass R3 is formed between the concave portion 26 provided in the syringe 20 and the first piston 31. The bypass R3 lets the filling room R1 communicate with the filling room R2.

Here, a description is given of a method of use of the present embodiment. Basic operation of the present embodiment is substantially the same as those in other embodiments. From the state illustrated in FIG. 39, the plunger operation member 50 is pushed in. Then, the second piston 32 is also pushed into the syringe 20, and accordingly, the second agent C2 is ready to be pumped. At this time, the first piston 31 is displaced toward the front end portion 23 in response to urging force received from the second agent C2. Then, when reaching the concave portion 26, as illustrated in FIG. 40, the first piston 31 forms the bypass R3 with the concave portion 26 provided in the syringe 20. The bypass R3 lets the second agent C2 inside the filling room R2 flow into the filling room R1. With the above structure, the second agent C2 inside the filling room R2 is permeated with the first agent C1. At this time, since pressure between the first piston 31 and the second piston 32 is decreased, the first piston 31 stays on the concave portion 26 so as to secure the bypass R3.

Figure 41:
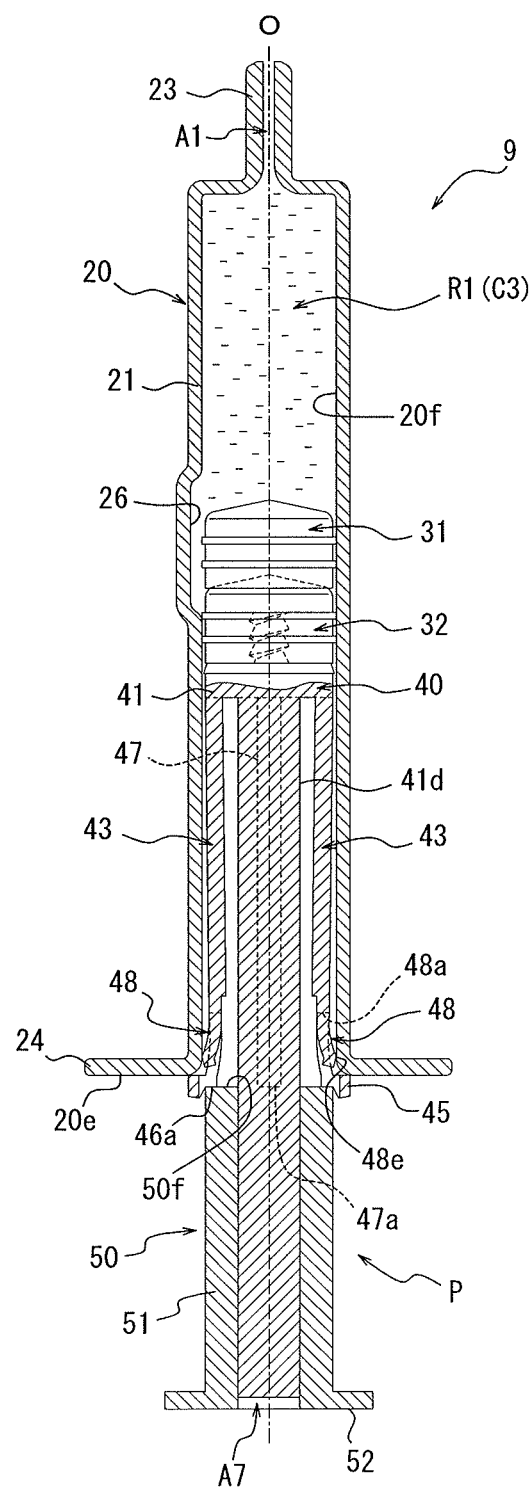
FIG. 41 is a side view taken along a partial section illustrating a state where a plunger is locked.

When the plunger P is pushed further, the elastic tongue piece 48 provided in the arm 43 is curved outward toward the rear end, and the end 48e of the elastic tongue piece 48 is oriented outward. Accordingly, the plunger P is allowed to enter the syringe 20 though the opening A2 provided in the rear end of the syringe 20. Furthermore, when the elastic tongue piece 48 enters the syringe 20, the end surface 50f of the plunger operation member 50 that is on the side of the main body presses the step bottom surface 46a provided in the arm 43 as the pressed surface, and restrains the arm 43. Accordingly, as illustrated in FIG. 41, the elastic tongue piece 48 undergoes flexure deformation starting from the fixed end 48a connected to the arm 43. As a result, the elastic tongue piece 48 is allowed to slide on the inner circumferential surface 20f of the syringe 20. With the above structure, as illustrated in FIG. 41, the second agent C2 may be permeated with the first agent C1 until the protrusion 45, following the elastic tongue piece 48, comes into contact with the rear end 20e of the syringe 20. As illustrated in FIG. 41, when the protrusion 45 comes into contact with the rear end 20e of the syringe 20, the plunger P may not be pushed in anymore. Therefore, for example, as illustrated in FIG. 41, by setting the protrusion 45 to be in contact with the rear end 20e of the syringe in a position where the second piston 32 is in contact with the first piston 31, the second agent C2 is flowed into the filling room R1 completely.

Figure 42:
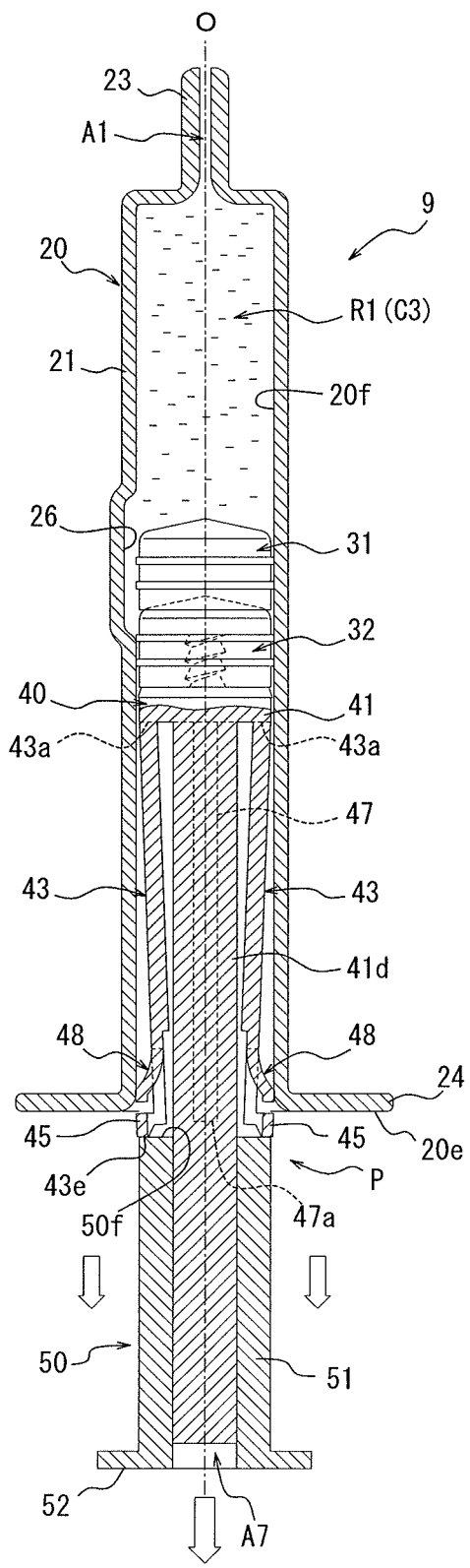
FIG. 42 is a side view taken along a partial section illustrating a state where the pushing of a plunger is released for starting ejection of a mixture in the syringe-type dispenser of FIG. 39.

Once it becomes impossible to push in the plunger P, when the pushing of the plunger P is released, the free end 43e of the arm 43 is released from restraint that is caused by pressing force applied by the plunger operation member 50. At this time, as a reaction, restoring force against the flexure deformation of the elastic tongue piece 48 being in contact with the inner circumferential surface 20f of the syringe 20 acts upon the arm 43. As a result, as illustrated in FIG. 42, the arm 43 undergoes inward deformation starting from the fixed end 43a while pushing back the plunger operation member 50 along the shaft portion 41d. Accordingly, as illustrated in FIG. 42, the locking state of the protrusion 45 and the rear end 20e of the syringe 20 is released.

In the present embodiment in particular, when, from the initial state, the plunger P is pushed in, the end surface 50f of the plunger operation member 50 that is on the side of the main body is guided by the step side surface 46b of the arm 43. As a result, the piston holding member 40 is pushed in stably and effectively. Furthermore, when the pushing of the plunger P is released, the step side surface 46b of the arm 43 serves as a guide for pushing back the end surface 50f (a front end portion) of the plunger operation member 50 that is on the side of the main body. Accordingly, while the plunger operation member 50 is pushed back, the portion of the arm 43 that is on the side of the free end 43e undergoes inward deformation without difficulty.

Figure 43:
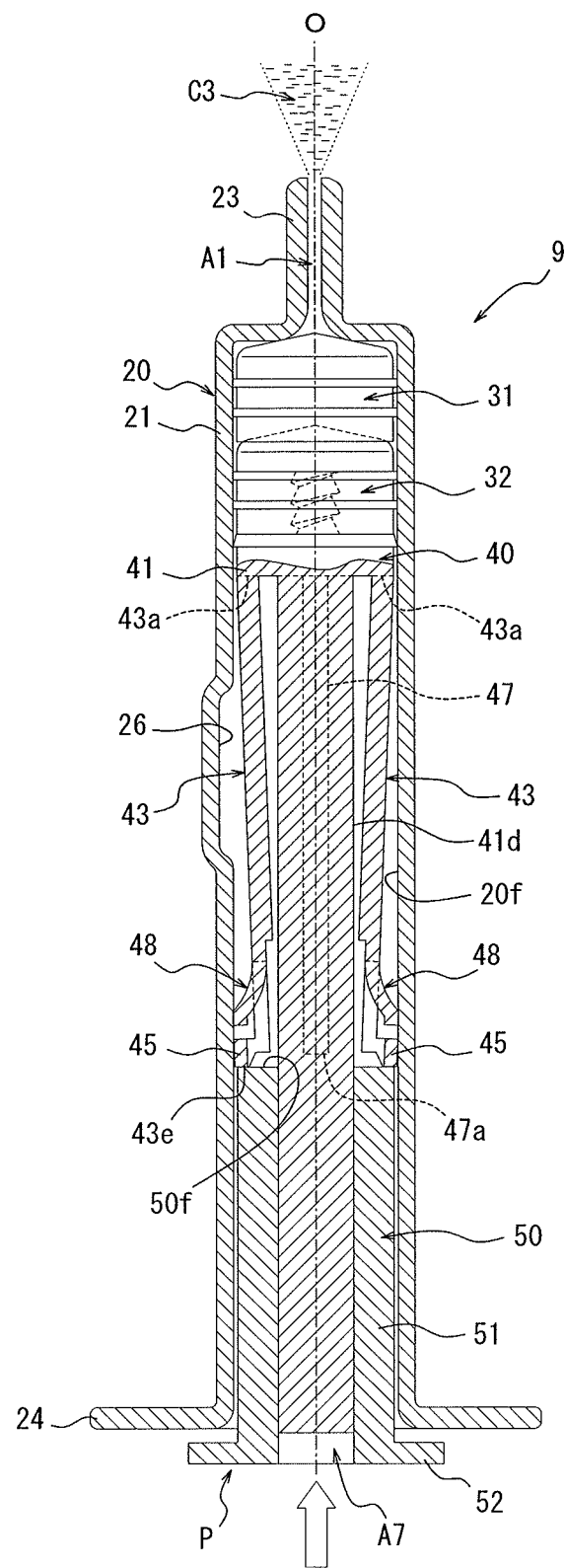
FIG. 43 is a side view taken along a partial section illustrating a state where the ejection of the mixture is completed in the syringe-type dispenser of FIG. 39.

In the present embodiment, after the plunger operation member 50 is pushed back in conjunction with the release of the locking between the protrusion 45 of the arm 43 and the rear end 20e of the syringe 20, as illustrated in FIG. 42, the rear end surface of the protrusion 45 contacts the end surface 50f of the plunger operation member 50 that is on the side of the main body. In the present embodiment in particular, as described above, the rear end surface of the protrusion 45 is formed as the free end 43e of the arm 43 and as the tapered surface inclined at the angle θ. Accordingly, as illustrated in FIG. 42, the free end 43e of the arm 43 forms the flat pressed surface in a state where the arm 43 has undergone inward deformation. Accordingly, when the plunger P is pushed in again, the free end 43e of the arm 43 effectively receives pressing force from the end surface 50f of the plunger operation member 50 that is on the side of the main body. With the above structure, after the pushing of the plunger P is loosened, by pushing in the plunger P again, as illustrated in FIG. 43, a content (a mixture) C3 of the first agent C1 and the second agent C2 is ejected through the bypass R3.

Furthermore, according to the present embodiment, since the locking of the arm 43 with respect to the syringe 20 is released by the restoring force of the elastic tongue piece 48 provided in the arm 43, wherever the elastic tongue piece 48 is positioned with respect to the arm 43, by releasing pressure to the free end 43e of the arm 43, the locking of the arm 43 is released. Therefore, as in the present embodiment, the elastic tongue piece 48 may be arranged in a position closest to the protrusion 45. In the above circumstance, the elastic tongue piece 48 is not deformed until immediately before the arm 43 is locked, and even when the pushing of the plunger P is loosened or released in the middle of mixing of the first agent C1 and the second agent C2, the arm 43 remains capable of being locked with respect to the syringe 20. Therefore, by arranging the elastic tongue piece 48 in the position closest to the protrusion 45, even when the pushing of the plunger P is stopped in the middle of the mixing, the first agent C1 is precisely mixed with the second agent C2 without the protrusion 45 being released in response to the plunger operation member 50 being pushed back.

As described above, according to the present embodiment, even when it is attempted to push in the plunger P at once, the protrusion 45 of the arm 43 is locked by the rear end 20e of the syringe 20. Accordingly, by setting the locked position to be a position where the second piston 32 contacts the first piston 31, the first piston 31 stays put once with the bypass R3 being formed as illustrated in FIG. 40, and then, the first piston 31 may not be pushed directly into the syringe 20 until the second piston 32 contacts the first piston 31 as illustrated in FIG. 41. Accordingly, it is not necessary to push in the plunger P carefully from the initial state. Furthermore, since the first piston 31 stays put while the bypass R3 is maintained, an operation, for example, of shaking the syringe-type dispenser 9 is possible. As a result, the two agents are mixed efficiently and reliably. Furthermore, since the locking of the plunger P is released simply by releasing the pushing of the plunger operation member 50, subsequently, simply by pushing in the plunger P again without passing the syringe-type dispenser 9 from one hand to the other, the mixture C3 may be ejected through the ejection orifice A1. Thus, according to the present embodiment, the two agents are mixed with a simple operation, and the mixture C3 is ejected by a series of operations.

Although the various embodiments of the present invention have been described above, according to the present invention, various modifications are possible. For example, two or more arms may be provided. In particular, as in the embodiments described on the above, providing an even number of arms allows favorable operation since stable balance is achieved around the axis line O. Furthermore, by exchanging the chip 61 of the nozzle 60, ejection in the form of form, instead of spray, is possible. Moreover, according to the present invention, the nozzle 60 may be omitted. Moreover, the components adopted in the above embodiments may be combined for use as appropriate.

INDUSTRIAL APPLICABILITY

The present invention is applicable to various syringe-type dispensers as long as the syringe-type dispensers include a syringe and a plunger configured to be pushed into the syringe. Accordingly, contents are not limited to nasal drops or the like, and various contents may be adopted.

REFERENCE SIGNS

1 nasal spray dispenser (Embodiment 1)
2 nasal spray dispenser (Embodiment 2)
3 nasal spray dispenser (Embodiment 3)
4 nasal spray dispenser (Embodiment 4)
5 nasal spray dispenser (Embodiment 5)
6 nasal spray dispenser (Embodiment 6)
7 nasal spray dispenser (Embodiment 7)
8 nasal spray dispenser (Embodiment 8)
9 nasal spray dispenser (Embodiment 9)
20 syringe
30 piston
31 first piston (piston)
32 second piston (piston)
40 piston holding member
41 main body of piston holding member
41d shaft portion
41s (play) space
43 arm (elastic deforming portion)
43a fixed end of arm
43e free end of arm
44 slide projection
44f inclined surface
45 protrusion (stopper portion)
46 step (restriction portion)
46a step bottom surface
46b step side surface
47 support portion
47a support portion end surface
48 elastic tongue piece
48a fixed end of elastic tongue piece
48e end of elastic tongue piece
50 plunger operation member
51 main body of plunger operation member
51a main body end surface
51b outer edge of main body end surface
51s play space
52 plunger operation portion
57 convex portion of main body
57a convex portion end surface
57b convex portion side surface
70 intermediate member
70f end surface of intermediate member that is on the side of main body
71 main body of intermediate member
71f rear end surface of main body
73 arm (elastic deforming portion)

73a fixed end of arm
73e free end of arm
75 protrusion (stopper portion)
76 step
76a step bottom surface
76b step side surface
77 support portion
77a support portion end surface
78 elastic tongue piece
78a fixed end of elastic tongue piece
78e end of elastic tongue piece
80 plunger
81 main body
82 plunger operation portion
83 arm (elastic deforming portion)
83a front end side arm
83$a_1$ coupling base portion on the side of bent portion
83$a_2$ portion on the side of main body
83b rear end side arm
83$b_1$ coupling base portion on the side of bent portion
83c bent portion
83d groove portion
84 slide projection
84f inclined surface
85 protrusion (stopper portion)
86 elastic portion (elastic deforming portion)
86a contact portion
87 support portion
87a support portion end surface
90 pressed portion
90f pressed surface
93 torsion spring portion (elastic deforming portion)
93a fixed end
93b fixed end
94 protrusion (stopper portion)
100 cartridge
110 sleeve member
110a trunk portion
110b overhanging portion
110c circumferential wall
111 crank
111a torsion passage
111b first push-in passage
111c return passage
111d second push-in passage
111e retreating portion
120 finger rest cover
121 partition wall
121a annular portion
121b cone-shaped curved portion
121c tubular body portion
121f inner circumferential surface of tubular body portion
122 slit (elastic region)
123 connecting piece (elastic region)
A1 ejection orifice
A2 opening provided in rear end of syringe
A4 through hole
A5 opening
A6 through hole
A7 through hole
C content
C1 first agent
C2 second agent
C3 mixture
E elastic region (elastic deforming portion)
M detent means
P plunger R room
R1 filling room (first agent)
R2 filling room (second agent)
R3 bypass
R5 inner room

The invention claimed is:

1. A metered quantity syringe-type dispenser, comprising:
a syringe;
a plunger configured to be pushed into the syringe;
an elastic deforming portion configured to be deformed inside the syringe in response to the pushing of the plunger, a stopper portion extending from the elastic deforming portion configured to be locked with respect to the syringe and to be released from being locked by a restoring force of the elastic deforming portion;
wherein the dispenser is configured such that when the plunger is pushed to eject a content contained in the syringe, the stopper portion is locked by the syringe while the elastic deforming portion undergoes deformation, and pushing movement of the plunger is restricted, and
wherein the dispenser is configured such that when pushing movement of the plunger is released or when the plunger is pulled back, locking of the stopper portion with respect to the syringe is released by the restoring force of the elastic deforming portion, thereby allowing the plunger to be pushed again.

2. The metered quantity syringe-type dispenser of claim 1, wherein
the elastic deforming portion is subject to inwardly urging force when the stopper portion is locked with respect to the syringe and includes a restriction portion by which inward displacement caused by the urging force is restricted, and the locking of the stopper portion is released by releasing the restriction portion.

3. The metered quantity syringe-type dispenser of claim 2, wherein
the plunger includes a piston holding member and a plunger operation member, the piston holding member including a piston and being provided with at least one arm extending rearward from the piston, and the plunger operation member being configured to press a free end of the at least one arm so as to push the piston into the syringe,
the at least one arm includes the restriction portion configured to be pressed by the plunger operation member, thereby the at least one arm constituting the elastic deforming portion, and
the at least one arm is provided with a slide projection configured to enter the syringe through an opening provided in a rear end of the syringe and to deform the at least one arm inward while sliding on an inner circumferential wall of the syringe and with a protrusion configured to be locked by the rear end of the syringe and to be released by the restoring force of the at least one arm starting from the slide projection, thereby the protrusion constituting the stopper portion.

4. The metered quantity syringe-type dispenser of claim 3, wherein
the piston holding member includes a shaft extending rearward from the piston and the at least one arm in an integrated manner, and
the plunger operation member is provided with inner room for accommodating the shaft and with a cutout in which the at least one arm is operatively fitted, the cutout including an abutment end portion that is formed as a pressing surface that presses the free end of the at least one arm.

5. The metered quantity syringe-type dispenser of claim 4, wherein
the slide projection comprises an elastic tongue piece.

6. The metered quantity syringe-type dispenser of claim 3, wherein
the piston holding member is provided with play space that allows the plunger operation member to be pushed back and a locking portion that holds a head provided in a shaft of the plunger operation member by preventing the head from slipping off.

7. The metered quantity syringe-type dispenser of claim 6, wherein
the slide projection comprises an elastic tongue piece.

8. The metered quantity syringe-type dispenser of claim 3, wherein
the plunger operation member and the at least one arm include a stopper releasing portion by which an inside of the at least one arm is brought into contact with the plunger operation member so that inward deformation of the at least one arm is prevented and by which the contact is released by pulling back the plunger operation member from the inside of the at least one arm so that the locking of the stopper portion is released.

9. The metered quantity syringe-type dispenser of claim 8, wherein
the slide projection comprises an elastic tongue piece.

10. The metered quantity syringe-type dispenser of claim 3, wherein
the slide projection comprises an elastic tongue piece.

11. The metered quantity syringe-type dispenser of claim 1, wherein
the plunger includes a piston holding member, a plurality of intermediate members, and a plunger operation member, the piston holding member including a piston and being provided with a shaft extending rearward from the piston, the plurality of intermediate members being assembled through the shaft in a manner such that the plurality of intermediate members are capable of sliding sequentially and the plurality of intermediate members each being provided with at least one arm extending rearward from the piston, and the plunger operation member being configured to press a free end of the at least one arm so as to push the piston into the syringe through the shaft,
the at least one arm includes an elastic tongue piece configured to enter the syringe through an opening provided in a rear end of the syringe and to cause the at least one arm to undergo flexure deformation while sliding on an inner circumferential wall of the syringe, thereby the elastic tongue piece constituting the elastic deforming portion, and
the at least one arm is provided with a protrusion configured to be locked by the rear end of the syringe and to be released by restoring force of the at least one arm caused by deformation of the elastic tongue piece, thereby the protrusion constituting the stopper portion.

12. The metered quantity syringe-type dispenser of claim 1, further comprising:
a piston holding portion including a piston; a plunger operation portion arranged in a rear end of the piston holding portion; and a plurality of arm portions configured to couple the piston holding portion and the plunger operation portion in an integrated manner, wherein
the plurality of arm portions each include a front end side arm connected to the piston holding portion, a rear end side arm connected to the plunger operation portion, and a bent portion coupling the front end side arm with the rear end side arm, the front end side arm being provided with a slide projection configured to enter the syringe through an opening provided in a rear end of the syringe and to cause the front end side arm to undergo flexure deformation while sliding on an inner circumferential wall of the syringe, thereby, the plurality of arm portions constituting the elastic deforming portion in cooperation with an elastic portion configured to couple the piston holding portion and the plunger operation portion in an integrated manner, and
the bent portion includes a portion serving as the stopper portion that is configured to be locked by the rear end of the syringe and to be released by restoring force of the front end side arm starting from the slide projection.

13. The metered quantity syringe-type dispenser of claim 1, wherein
the plunger includes a piston holding member and a plunger operation member, the piston holding member including a piston and being provided with a pressed portion and a torsion spring portion configured to be deformable and restorable around its axis line, the pressed portion being provided in rear of the piston holding member via the torsion spring portion, and the plunger operation member being configured to press the pressed portion of the piston holding member so as to push the piston into the syringe,
the syringe is provided, inside thereof, with a sleeve member configured to slidably accommodate the piston holding member, and
the pressed portion of the piston holding member is provided with a lateral protrusion configured to be locked to the sleeve member and to be released by restoring force of the torsion spring portion, and the sleeve member is provided with a crank configured to guide the lateral protrusion, thereby the torsion spring portion constituting the elastic deforming portion, and the lateral protrusion constituting the stopper portion.

14. The metered quantity syringe-type dispenser of claim 1, wherein
the syringe includes a finger rest to which a finger rest cover is fitted, the finger rest cover including a tubular body portion and an elastic region provided around the tubular body portion, the tubular body portion extending toward an opening provided in a rear end of the syringe, and the elastic region being configured to be deformable and restorable,
the plunger includes a piston holding member and a plunger operation member, the piston holding member including a piston and being provided with at least one arm extending rearward from the piston, and the plunger operation member being configured to press a free end of the at least one arm so as to push the piston into the syringe, and
the at least one arm is provided with a protrusion configured to be hooked in the elastic region and cause the elastic region to undergo elastic deformation and to be released from being hooked by inward deformation of the at least one arm that is caused by restoring force of the elastic region, thereby the elastic region and the protrusion constituting the elastic deforming portion and the stopper portion, respectively.

15. The metered quantity syringe-type dispenser of claim 1, wherein the plunger includes a piston holding member and a plunger operation member, the piston holding member including a piston and being provided with a shaft and at least one arm extending rearward from the piston, and the plunger operation member being configured to press a free end of the at least one arm so as to push the piston into the syringe through the shaft, the at least one arm includes an elastic tongue piece configured to enter the syringe through an opening provided in a rear end of the syringe and to cause the at least one arm to undergo flexure deformation while sliding on an inner circumferential wall of the syringe, thereby the elastic tongue piece constituting the elastic deforming portion, and the at least one arm is provided with a protrusion being configured to be locked by the rear end of the syringe and to be released by restoring force of the at least one arm caused by deformation of the elastic tongue piece, thereby the protrusion constituting the stopper portion.

* * * * *